(12) United States Patent
Rao et al.

(10) Patent No.: US 8,048,864 B1
(45) Date of Patent: Nov. 1, 2011

(54) REGULATORS OF NFAT AND/OR STORE-OPERATED CALCIUM ENTRY

(75) Inventors: Anjana Rao, Cambridge, MA (US); Patrick Hogan, Cambridge, MA (US); Sonia Sharma, Framingham, MA (US)

(73) Assignee: Immune Disease Institute, Inc., Boston, MA (US)

( * ) Notice: Subject to any disclaimer, the term of this patent is extended or adjusted under 35 U.S.C. 154(b) by 0 days.

(21) Appl. No.: 12/575,655

(22) Filed: Oct. 8, 2009

Related U.S. Application Data

(60) Provisional application No. 61/103,628, filed on Oct. 8, 2008.

(51) Int. Cl.
*A61K 31/70* (2006.01)
*C07H 21/04* (2006.01)

(52) U.S. Cl. .......................................... 514/44; 536/24.5

(58) Field of Classification Search .......................... None
See application file for complete search history.

(56) References Cited

OTHER PUBLICATIONS

Kloor et al., Biochemica et Biophysica Acta 2002, vol. 1579, pp. 219-224.*

Ishikawa, J. et al., "A Pyrazole Derivative, YM-58483, Potently Inhibits Store-Operated Sustained CA2+ Influx and IL-2 Production in T Lymphocytes", J. Immunol., 170, pp. 4441-4449, 2003.
Ohga, K. et al., "Characterization of YM-58483/BTP2, A Novel Store-Operated CA2+ Entry Blocker, on T Cell-Mediated Immune Responses in Vivo", International Immunopharamcology 8, pp. 1787-1792, 2008.
Picard, C. et al., "STIM1 Mutation Associated With a Syndrome of Immunodeficiency and Autoimmunity", N. Engl. J. Med. 360(19), pp. 1971-1980, May 7, 2009.
Swanson, S. et al., "Cyclosporin-Mediated Inhibition of Bovine Calcineurin by Cyclophilins A and B", Proc. Natl. Acad. Sci., vol. 89, pp. 3741-3745, May 1992.
Trevillyan, J. et al., "Potent Inhibition of NFAT Activation and T Cell Cytokine Production by Novel Low Molecular Weight Pyrazole Compounds", The Journal of Biological Chemistry, vol. 276, No. 51, pp. 48118-48126, Dec. 21, 2001.
Wittmann, M. et al., "Ciritcal Involvement of IL-12 in IFN-gamma Induction by Calcineurin Antagonists in Activated Human Lymphocytes", Journal of Leukocyte Biology, vol. 80, pp. 75-86, Jul. 2006.
Wulff, H. et al., "Design of a Potent and Selective Inhibitor of the Intermediate-Conductance CA2+-Activated K+ Channel, IKCA1: A Potential Immunosuppressant", PNAS, vol. 97, No. 14, pp. 8151-8156, Jul. 5, 2000.

* cited by examiner

*Primary Examiner* — Tracy Vivlemore
(74) *Attorney, Agent, or Firm* — Nixon Peabody LLP

(57) ABSTRACT

Embodiments of the inventions relates to modulating NFAT activity, modulating store-operated $Ca^{2+}$ entry into a cell and treating and/or preventing hyperactivity or inappropriate immune response by inhibiting the expression or activities of proteins involved in the calcineurin/NFAT axis.

18 Claims, 37 Drawing Sheets

Platewise Analysis (+/- k SD ie Z score)

1) Calculate Plate Average of experimental wells (excludes buffer and empty wells)

2) Calculate Plate SD of experimental wells

3) Calculate Z score for each experimental well
   Z score = (X - $Avg_{plate}$)/$SD_{plate}$ 4) Filter data set to omit data points with a Z score = +/-3 SD (extreme outliers)

5) Recalculate Plate Average (doesn't change much) and Plate SD (does change significantly)

6) Recalculate Z scores for each well
   weak hits: k = 2-3
   moderate hits: k = 3-5
   strong hits: k = >5

*FIG. 10*

Candidates

- all expected candidates: calcineurin, nuclear transport proteins, Stim, Orai
- candidates involved in Golgi-to-plasma membrane trafficking
- candidates associated with mitochondria
- a handful of interesting scaffold proteins (with PDZ domains, etc)
- candidates involved in ubiquitin metabolism
- noncoding RNAs (containing microRNAs?)
- RNA-binding proteins

*FIG. 16*

Secondary Assay I: Cherry Picks for SmartPool Deconvolution 500 cherry picks: (496 S/M + 4 W)

SmartPool deconvolution to individual duplexes:
4 siRNA/gene × 500 genes = 2000 wells i) Primary Readout (NFAT-GFP translocation by TG)
   4 color acquisition:
   -DAPI (stain, nuclear)
   -NFAT-GFP (stable living color, nuclear or cytoplasmic)
   -STIM1-DSRed (stable living color, ER/punctae)
   -Orai-Cy5 (transient FLAG ICC, surface)

ii) Second Readout (NFkB p65 translocation by TNF)
    2 color acquisition:
    -DAPI (stain, nuclear)
    -p65-Cy5 (endogenous p65 ICC, nuclear or cytoplasmic)

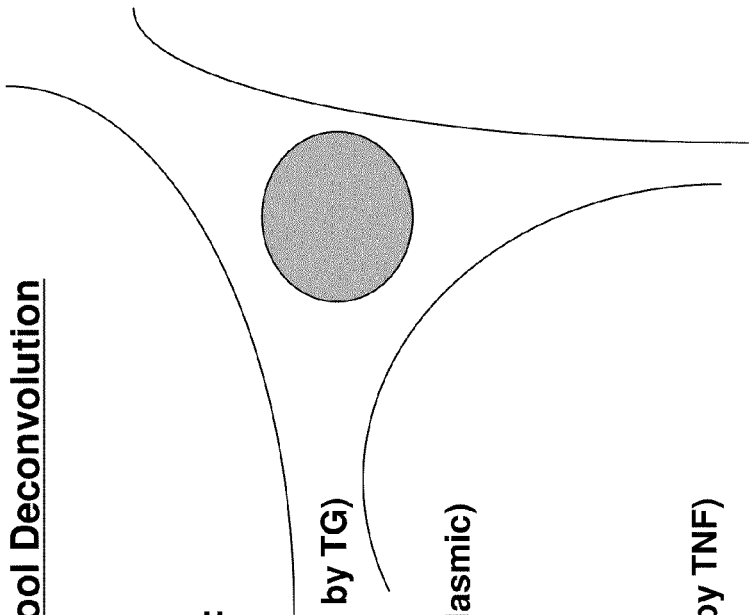

FIG. 17

Secondary Assay I: Cherry Picks for SmartPool Deconvolution

| plate | genes tested | genes (+) | 1 oligo/4 (+) | 2 oligo/4 (+) | 3 oligo/4 (+) | 4 oligo/4 (+) |
|---|---|---|---|---|---|---|
| 1 | 55 | 44 | 21 | 16 | 7 | 0 |
| 2 | 57 | 52 | 31 | 15 | 2 | 4 |
| 3 | 57 | 57 | 7 | 19 | 19 | 12 |
| 4 | 53 | 48 | 23 | 17 | 6 | 2 |
| 5 | 57 | 57 | 19 | 27 | 7 | 4 |
| 6 | 57 | 51 | 31 | 14 | 6 | 0 |
| 7 | 56 | 48 | 31 | 14 | 2 | 1 |
| 8 | 56 | 51 | 17 | 18 | 15 | 1 |
| 9 | 52 | 50 | 15 | 19 | 13 | 3 |
| total | 500 | 458 | 195 | 159 | 77 | 27 |
| total % | 100% | 92% | 39% | 31.8% | 15.4% | 5.40% | total>1/4  263
total %>1/4  52.6%

Tertiary Assay I: intracellular Ca²⁺ measurements
classify hits that affect calcium influx:

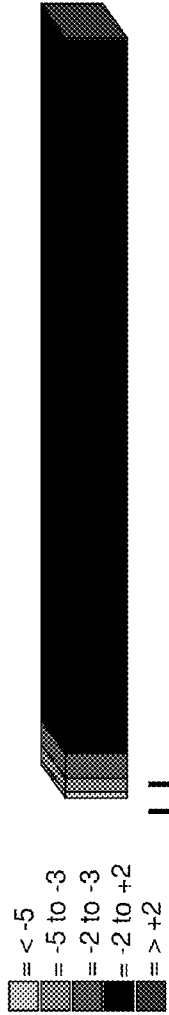

= < -5
= -5 to -3
= -2 to -3
= -2 to +2
= > +2 kinetic imaging in live cells of FURA2/AM fluorescence:

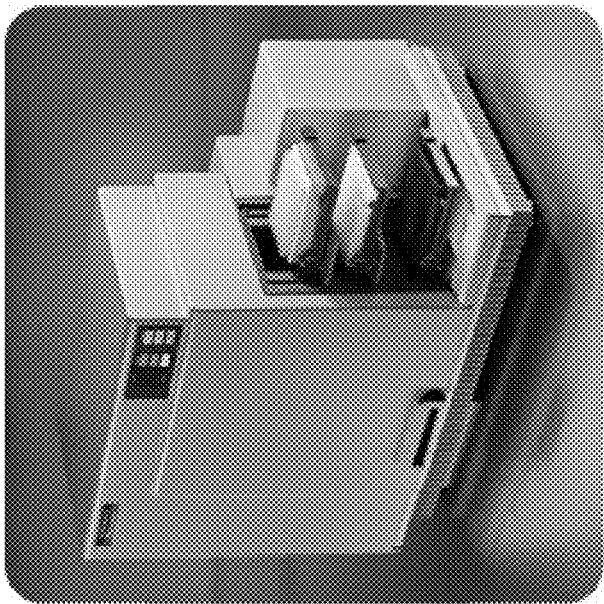

FlexStation III (Molecular Devices)
- kinetic imaging with integrated fluid transfer and simultaneous read of 8 wells/ 10 minutes (ie one column/96 well plate)
- integrated measurement of total fluorescence/well (no single cell measurements)

FIG. 19

Tertiary Assay I: intracellular Ca²⁺ measurements
classify hits that affect calcium influx:
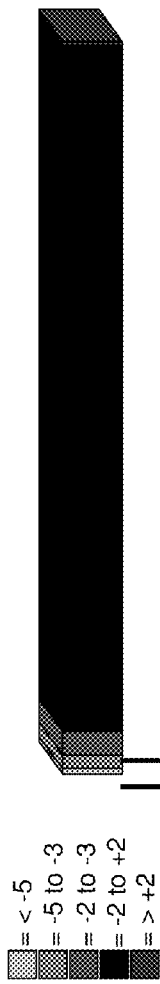
= < -5
= -5 to -3
= -2 to -3
= -2 to +2
= > +2
263 hits from secondary deconvolution
subtract hits with known function for nuclear import/export, transcription and splicing
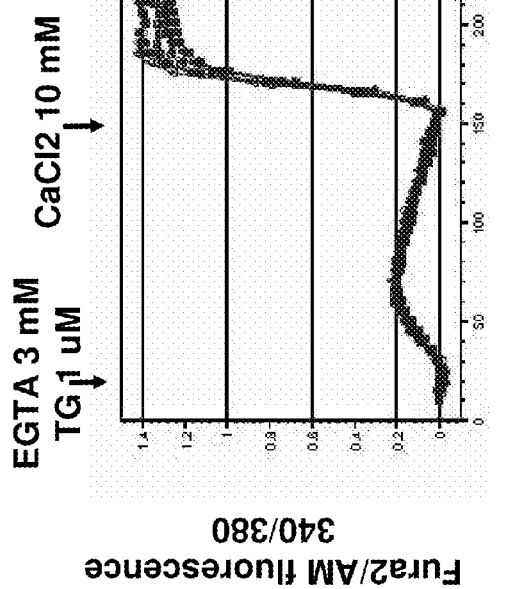
FIG. 20

| Gene | Primary Z score | Secondary Z score | GO/function/rationale |
|---|---|---|---|
| FRMPD1 2/4 | -4.9 | -3.1<br>-11.4 | FERM and PDZ-containing |
| KCNN4 4/4 | -4.5 | -2.8<br>-7.6<br>-5.5<br>-4.8 | $Ca^{2+}$-activated K+ channel;<br>Maintains negative membrane potential as driving force for $Ca^{2+}$ entry;<br>Localized to IS during T cell activation |
| UEV3 2/4 | -5.8 | -18.1<br>-6.6 | UEV and LD domains;<br>paralogue of TSG101;<br>may bind mono-ub proteins in the context of trafficking |
| SYT15 3/4 | -7.2 | -5.2<br>-6.9<br>-5.5 | Atypical $Ca^{2+}$-independent synaptogaminin membrane trafficking? |
| GPD1L 3/4 | -6.0 | -3.0<br>-7.0<br>-4.5 | Glycerol phosphate dehydrogenase 1-like; mitochondrial localization?<br>4 mutations associated with SIDS and/or BS |

*FIG. 25*

*FIG. 31*
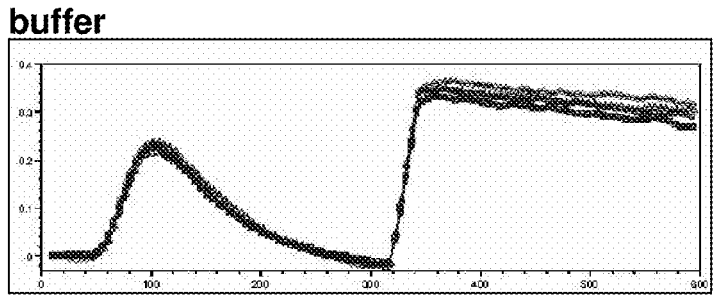
buffer
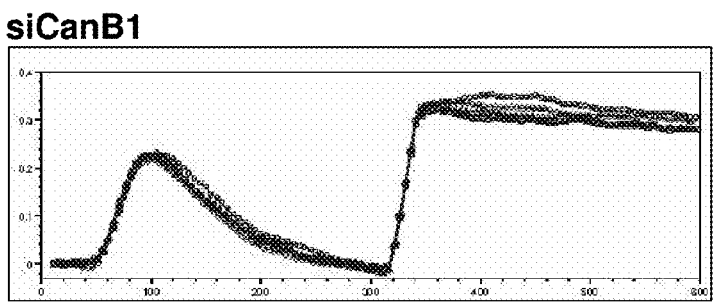
siCanB1
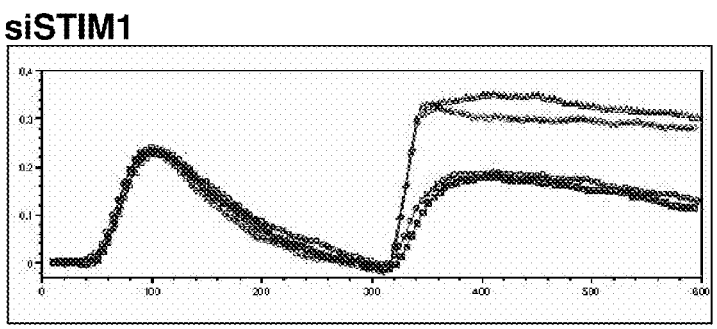
siSTIM1
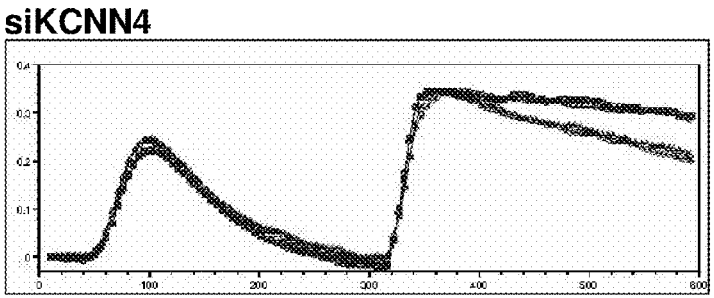
siKCNN4
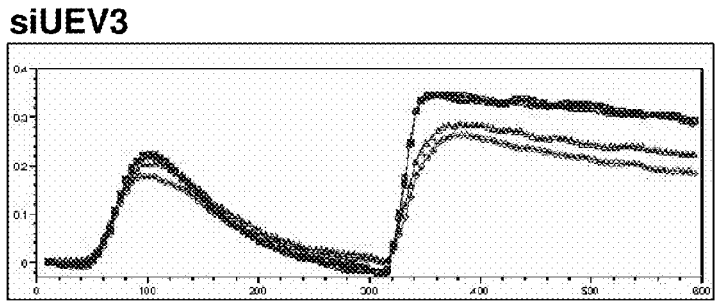
siUEV3

FIG. 32
siFRMPD1
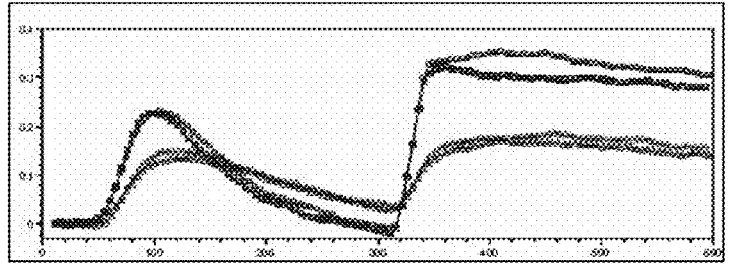
siGPD1L
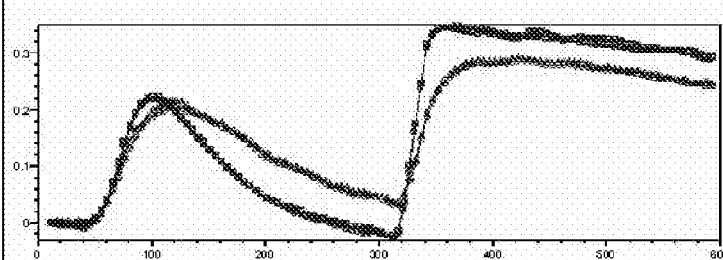
siSYT15
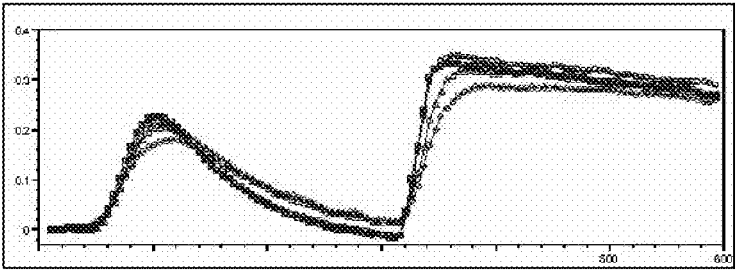
siLOC399959
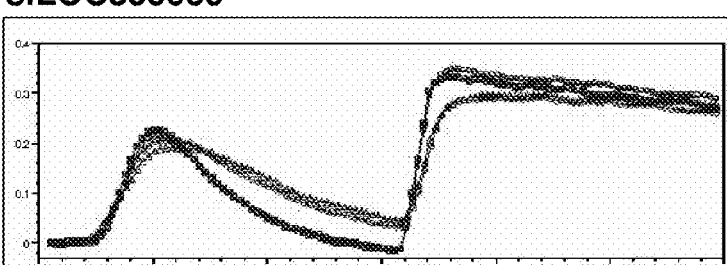
siGAF1
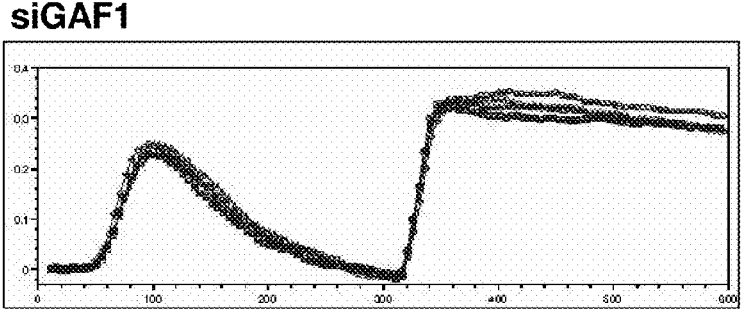

REGULATORS OF NFAT AND/OR STORE-OPERATED CALCIUM ENTRY

CROSS REFERENCE TO RELATED APPLICATIONS

This application claims benefit under 35 U.S.C. §119(e) of U.S. Provisional Application No. 61/103,628 filed on Oct. 8, 2008, the contents of which are incorporated herein by reference in its entirety.

GOVERNMENT SUPPORT

This invention was made with Government support under contract Nos. AI40127 and GM075256, awarded by the National Institutes of Health. The Government has certain rights in the invention.

FIELD OF THE INVENTION

The invention relates to modulating nuclear factors of activated T-cell (NFAT) and/or store operated $Ca^{2+}$ entry (SOCE) in cells, in particular T cells. The invention relates to the regulation of the activation of T cells and the modulation of immune responses.

BACKGROUND OF INVENTION

The calcium/calcineurin-dependent NFAT family is thought to have arisen following the recombination of an ancient precursor with a Rel domain about 500 million years ago, producing a new group of signaling and transcription factors (the NFAT genes) found only in the genomes of vertebrates. The family of NFAT transcription factor consists of five members NFAT1, NFAT2, NFAT3, NFAT4 and NFAT5. The NFAT proteins are activated by an increase in intracellular calcium levels, e.g., by means of store-operated calcium entry (SOCE). Calcium signaling is critical to NFAT activation because calmodulin, a well known calcium sensor protein, activates the serine/threonine phosphatase calcineurin. Activated calcineurin rapidly dephosphorylates the serine rich region (SRR) and SP-repeats in the amino termini of NFAT proteins resulting in a conformational change that exposes a nuclear localization signal resulting in NFAT nuclear import. The activated NFAT proteins, in turn, induce transcription of cytokine genes which are required for an immune response.

Nuclear import of NFAT proteins is opposed by maintenance kinases in the cytoplasm and export kinases in the nucleus. Export kinases, such as PKA and GSK-3β, must be inactivated for NFAT nuclear retention. NFAT proteins have weak DNA binding capacity. Therefore, to effectively bind DNA NFAT proteins must cooperate with other nuclear resident transcription factors. This important feature of NFAT transcription factors enables integration and coincidence detection of calcium signals with other signaling pathways such as ras-MAPK or PKC. In fact, cell biological, genetic and biochemical evidence indicates that the circuitry of this pathway is well suited for intercalation with older pathways, such as MAP kinase, WNT and NOTCH. This recombination enabled $Ca^{2+}$ signals to be redirected to a new transcriptional program, which provides part of the groundwork for vertebrate morphogenesis and organogenesis. Indeed, the calcineurin/NFAT axis is involved in numerous aspects of vertebrate morphogenesis: cell cycle regulation, cell differentiation, cell survival, angiogenesis, tumor cell invasion and metastasis, myogenesis, chondrocytes differentiation and the development of the cardiovascular system, the complex nervous system and the recombinational immune system. Consequently, deregulation of calcineurin/NFAT signaling and/or abnormal expression of its components have been associated with cell proliferation diseases such as cancer, autoimmune diseases, cardiovascular diseases, diabetes, and bone diseases to name a few. Discovery of modulators of $Ca^{2+}$ influxes and/or the calcineurin/NFAT axis can provide therapeutic avenues for these diseases.

SUMMARY OF THE INVENTION

Embodiments of the invention are based on the discovery that several hundred genes in the human and mouse genomes whose gene products directly and/or indirectly modulate nuclear factors of activated T cell (NFAT) activation and/or modulate the store-operated $Ca^{2+}$ entry (SOCE) into a cell. NFAT is a family of transcription factors that normally reside in the cytoplasm when inactive. When activated by dephosphorylation by calcineurin, the NFATs can translocate into the nucleus and "turn on" specific gene transcription. The inventors developed a cell-based reporter system for screening for modulators of (NFAT) and/or store-operated $Ca^{2+}$ entry into a cell, with NFAT nuclear translocation as the readout for scoring a modulator. The cell-based reporter system comprises a mammalian cell co-expressing a NFAT-GFP, a STIM1-RFP, and a Orai1-FLAG. The markers: GFP, RFP and FLAG-tag facilitate the visual localization of the respectively expressed proteins within the cell compartments. Thapsigargin (TG), a tight-binding inhibitor of sarco/endoplasmic reticulum $Ca^{2+}$ ATPase, was used to deplete the $Ca^{2+}$ in the endoplasmic reticulum and initiate SOCE, which in turn leads to NFAT dephosphorylation and NFAT nuclear translocation. The inventors used the cytoplasm-to-nuclear translocation of NFAT-GFP as their assay readout.

The inventors performed a large scale high-throughput siRNA screening of the human and mouse genome for genes that modulate NFAT nuclear translocation and/or SOCE. Genes that modulate the NFAT nuclear translocation and/or SOCE can either up-regulate (i.e. promote) or down-regulate (i.e. inhibit) NFAT nuclear translocation and/or SOCE. NFAT nuclear translocation and/or SOCE are necessary for the activation of T cells, the proliferation of activated T cells, and for maintaining the immune response involving T- and B-cells in the body. In addition, the NFAT translocation is associated with multiple signaling pathways such as the MAP kinase, WNT, and NOTCH signaling pathways. As such, NFATs directly and/or indirectly play important roles in cell proliferation and regeneration, cancer, angiogenesis, cardiovascular diseases, diabetes, neural regeneration, bone diseases and T cell adaptation to name a few. Therefore, identification of the modulator genes of NFAT nuclear translocation and/or SOCE can allow therapeutic regulation of the immune system, immune responses and other disease conditions associated with NFATs.

Inhibition of genes that up-regulate NFAT nuclear translocation and/or SOCE can help inhibit T-cell activation and immune response associated with hyperactivity or inappropriate activity of the immune system. Conversely, inhibition of genes that down-regulate NFAT nuclear translocation and/ or SOCE can help increase T cells activation and immune responses associated with immune deficiency disease or conditions.

Secondary and tertiary screens of the hits from primary screens were conducted. Secondary and tertiary screens comprise $Ca^{2+}$ influx as readout for scoring.

Accordingly, provided herein a method of modulating NFAT activity, the method comprising administering a therapeutically effective amount of a pharmaceutical composition comprising an agent that inhibits the activity a protein and/or the expression of a gene identified in Table 1, 2 or 3.

In one embodiment, provided herein is a method of modulating store-operated $Ca^{2+}$ entry into a cell, the method comprising administering a therapeutically effective amount of a pharmaceutical composition comprising an agent that inhibits the activity a protein expressed from a gene identified in Table 1, 2 or 3, and/or the expression of a gene identified in Table 1, 2 or 3.

In one embodiment, provided herein is a method of treating and/or preventing hyperactivity or inappropriate immune responses in a subject in need thereof, the method comprising administering a therapeutically effective amount of a pharmaceutical composition comprising an agent that inhibits the activity a protein expressed from a gene identified in Table 1, 2 or 3, and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2). In some embodiment, the subject can be one who is at risk of developing hyperactivity or inappropriate immune response, for example, an organ transplant recipient.

In some aspects, the hyperactivity or inappropriate immune response in a subject is associated with acute and chronic immune diseases, e.g., allergic and atopic diseases, e.g., asthma, allergic rhinitis, allergic conjunctivitis and atopic dermatitis, and to autoimmune diseases, e.g., rheumatoid arthritis, insulin-dependent diabetes, inflammatory bowel disease, autoimmune thyroiditis, hemolytic anemia and multiple sclerosis. Hyperactivity or inappropriate activity of the immune system is also involved in transplant graft rejections and graft-versus-host disease. Administering an agent that inhibits a gene identified in Table 1, 2 or 3, can down-regulate NFAT activity and/or store-operated $Ca^{2+}$ entry and thereby reduce chronic T cell activation.

In another embodiment, provided herein is a method of increasing immune response in a subject in need thereof, the method comprising administering a therapeutically effective amount of a pharmaceutical composition comprising an agent that inhibits the activity a protein expressed from a gene identified in Table 1, 2 or 3, and/or the expression of a gene identified in Table 1, 2 or 3.

In an embodiment, provided herein is a method of treating a cell proliferation disease or disorder in a subject in need thereof, the method comprising administering a therapeutically effective amount of a pharmaceutical composition comprising an agent that inhibits the activity of a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2). The cell proliferation disease or disorder is a neoplastic cell proliferation disorder and the neoplastic cell proliferation disorder is a therapy resistant cancer, a metastasis or malignant cancer.

In another embodiment, provided herein is a method of treating a cardiovascular disorder in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2). The cardiovascular disorders is cardiac hypertrophy, restenosis, atherosclerosis, or angiogenesis.

In another embodiment, provided herein is a method of treating an injury to the nervous system in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2).

In another embodiment, provided herein is a method of treating a bone disease in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Mail or dual-specificity tyrosine-(Y)-phosphorylation regulated kinase 2 (DYRK2), wherein excessive osteoclast formation and activity is suppressed.

In another embodiment, provided herein is a method of treating diabetes in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2).

In another embodiment, provided herein is a method of treating an injury to the nervous system in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2).

In another embodiment, provided herein is a method of treating an angiogenic disease or disorder in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2). The angiogenic disease or disorder is associated with VEGF-induced and IL-1 induced gene expression.

In some aspects, the angiogenesis disorder is selected from a group consisting of cancer, age-related macular degeneration, diabetic retinopathy; rheumatoid arthritis; Alzheimer's disease; obesity and endometriosis.

In another embodiment, the methods provided herein comprise a agent that is a nucleic acid inhibitor which inhibits gene expression.

In one aspect, the agent is a nucleic acid inhibitor. In some aspects, the nucleic acid is DNA, RNA, nucleic acid analogue, peptide nucleic acid (PNA), pseudo-complementary PNA (pcPNA), locked nucleic acid (LNA) or analogue thereof. In other aspects, the RNA is a small inhibitory RNA, siRNA, microRNA, shRNA, miRNA and analogues and homologues and variants thereof effective in gene silencing.

BRIEF DESCRIPTION OF THE DRAWINGS

FIG. 10 summarizes the steps for calculating Z scores.

FIG. 16 shows the summary of the identified genes/proteins categorized into groups.

FIG. 17 shows the summary of the secondary screening protocol of the hits from the primary screen.

FIG. 19 shows the instrumentation used in the tertiary screen.

FIG. 20 shows the methology of the tertiary screen.

FIG. 25 shows the summary of z scores obtained during the primary and secondary screen for a few select hits.

FIG. 31 shows some traces of calcium fluxes of cells with siRNA to select hits.

FIG. 32 shows some traces of calcium fluxes of cells with siRNA to select hits.

DETAILED DESCRIPTION OF THE INVENTION

Figure 1:
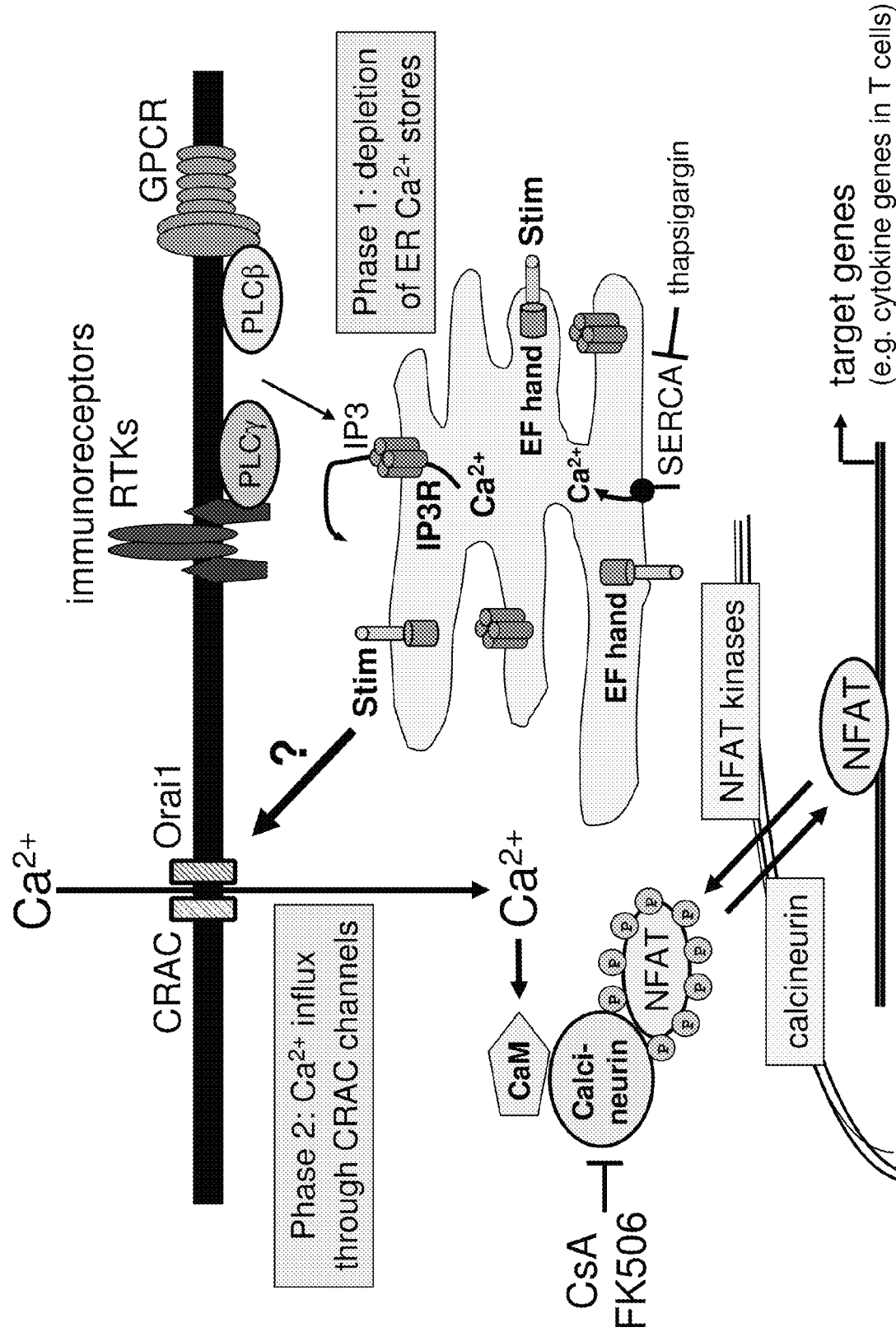
FIG. 1 shows schematic diagram of NFAT translocation and activation.
Figure 2:
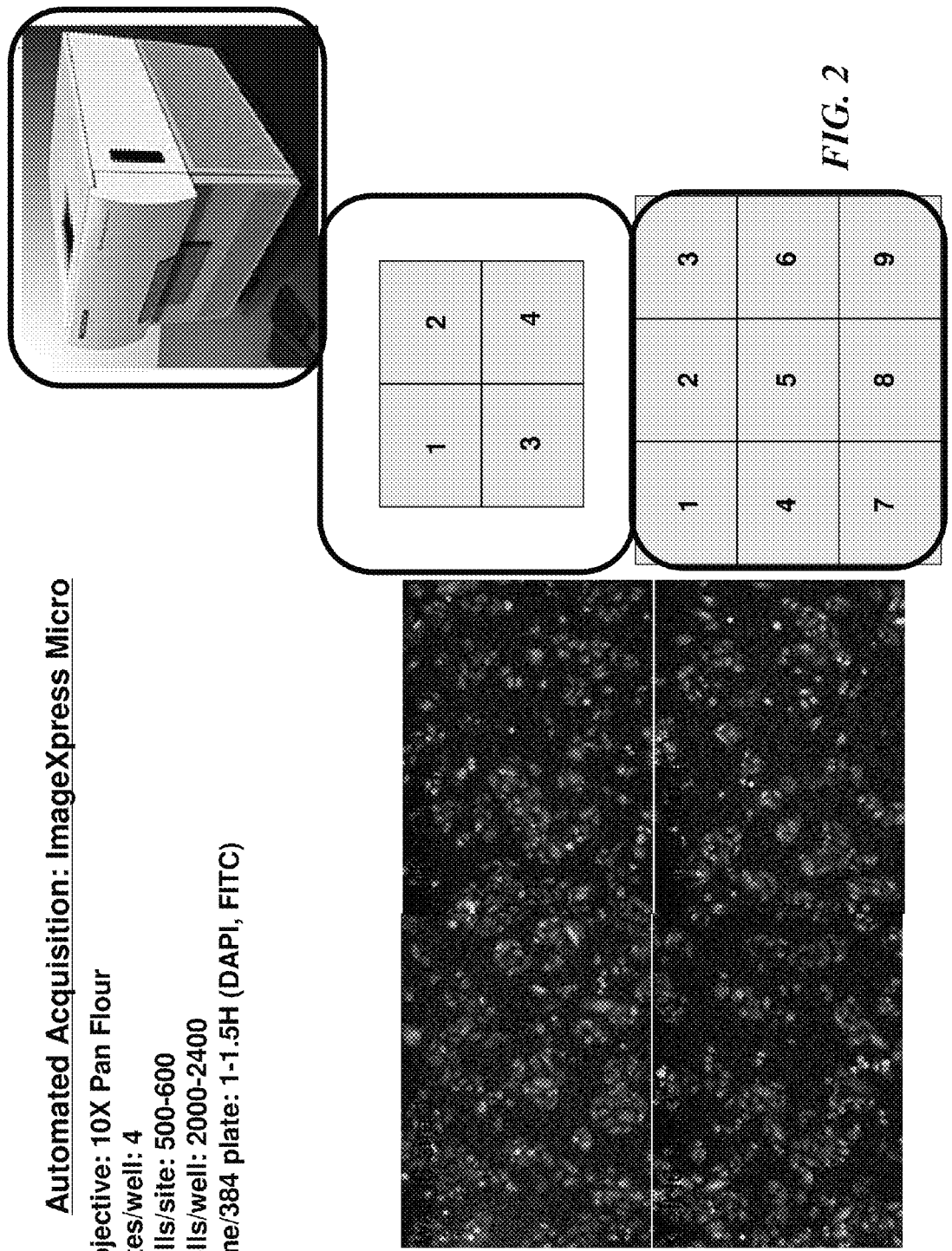
FIG. 2 shows the automated data acquisition by ImageXpress Micro
Figure 3:
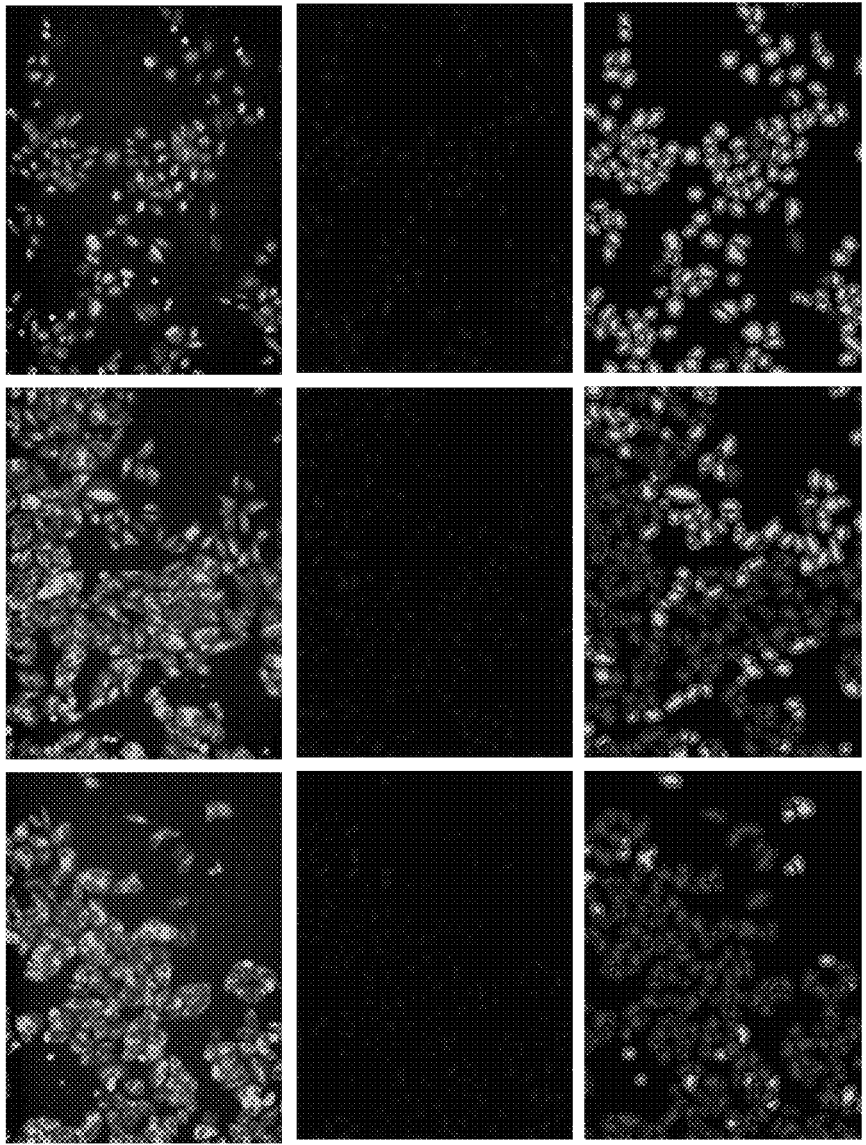
FIG. 3 shows the MetaXpress automated analysis of cell scoring and/or nuclear translocation of NFAT-GFP in thapsigargin treated cells.
Figure 4:
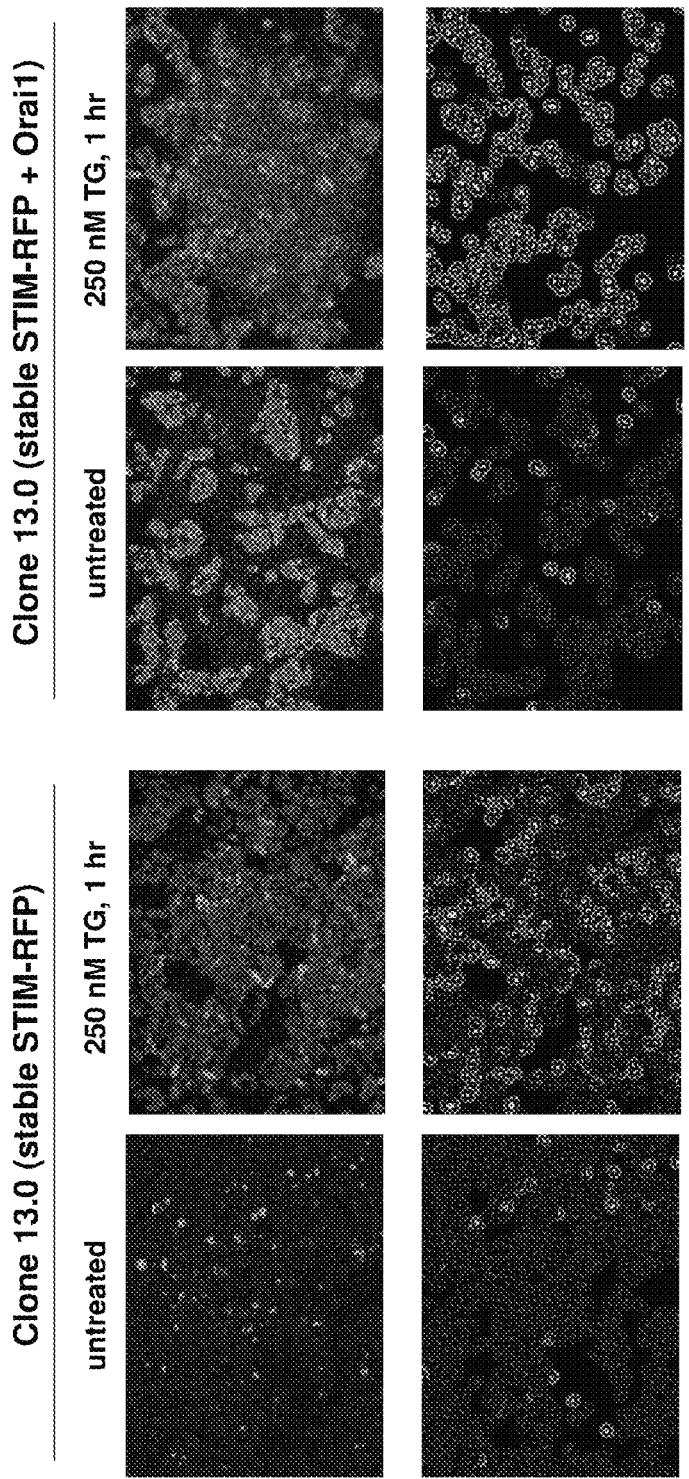
FIG. 4 shows that combined STIM1 and Orai1 expression in Hela cells enhances nuclear translocation of NFAT-GFP.
Figure 5:
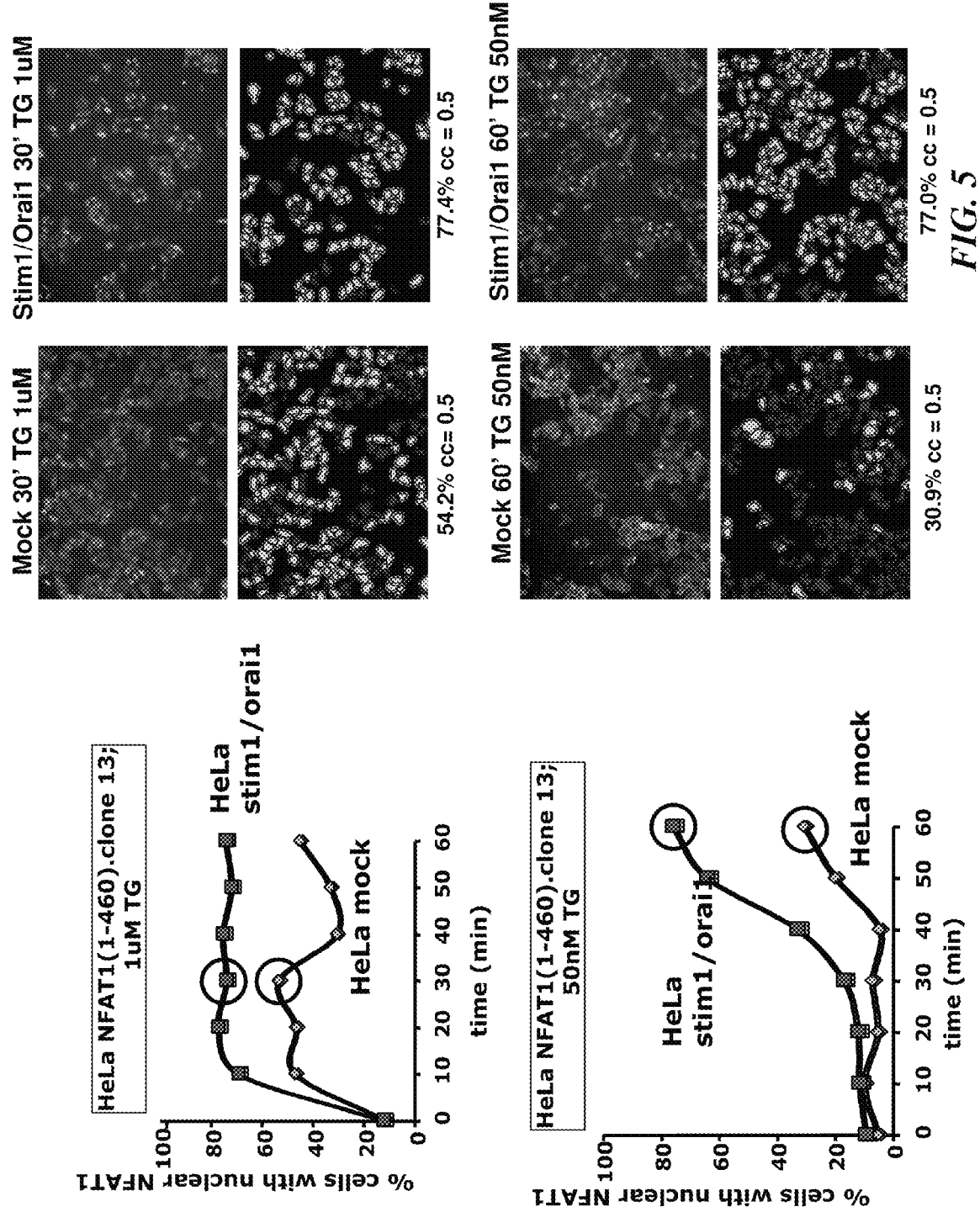
FIG. 5 shows combined STIM1 and Orai1 expression in Hela cells enhances NFAT nuclear translocation.
Figure 6:
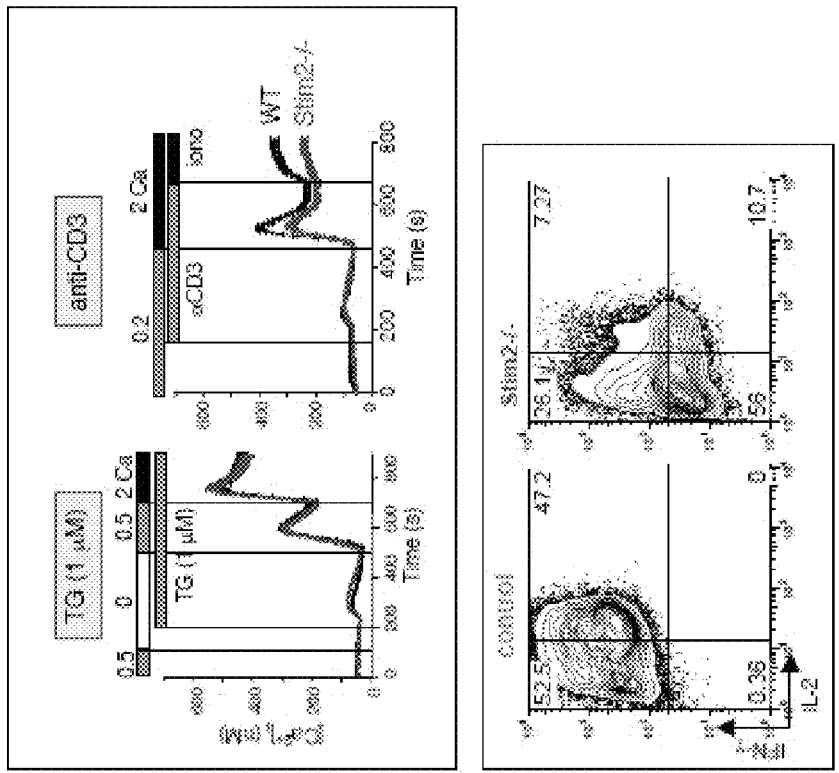
FIG. 6 shows the reason for choosing to use NFAT translocation as an screening assay: $Stim2^{-/-}$ T cells have a very slight defect in acutely measured store operated $Ca^{2+}$ entry (SOCE) but a substantial defect in NFAT nuclear translocation and cytokine production.
Figure 7:
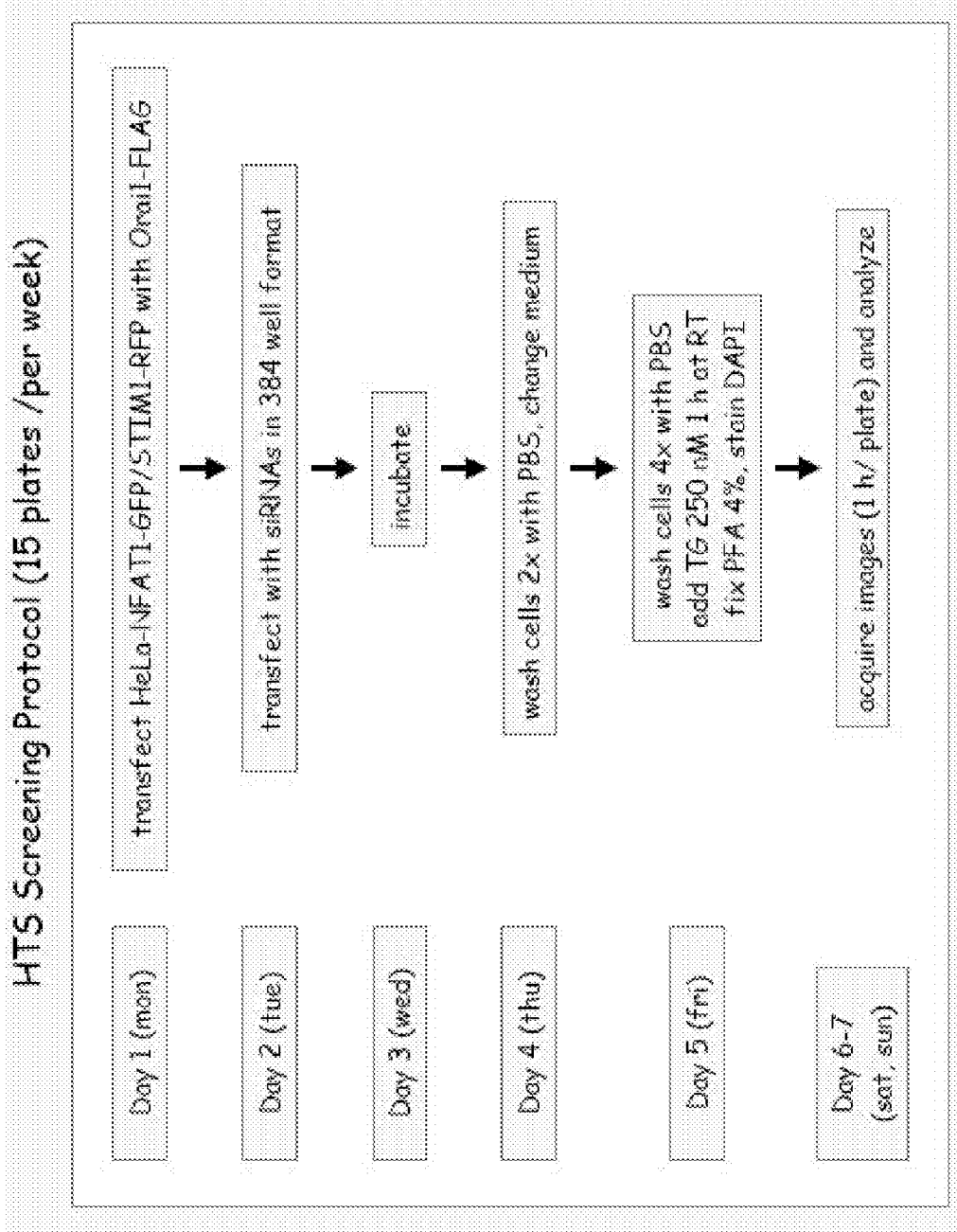
FIG. 7 shows one of the flow diagram of the high-throughput screening protocol.
Figure 8:
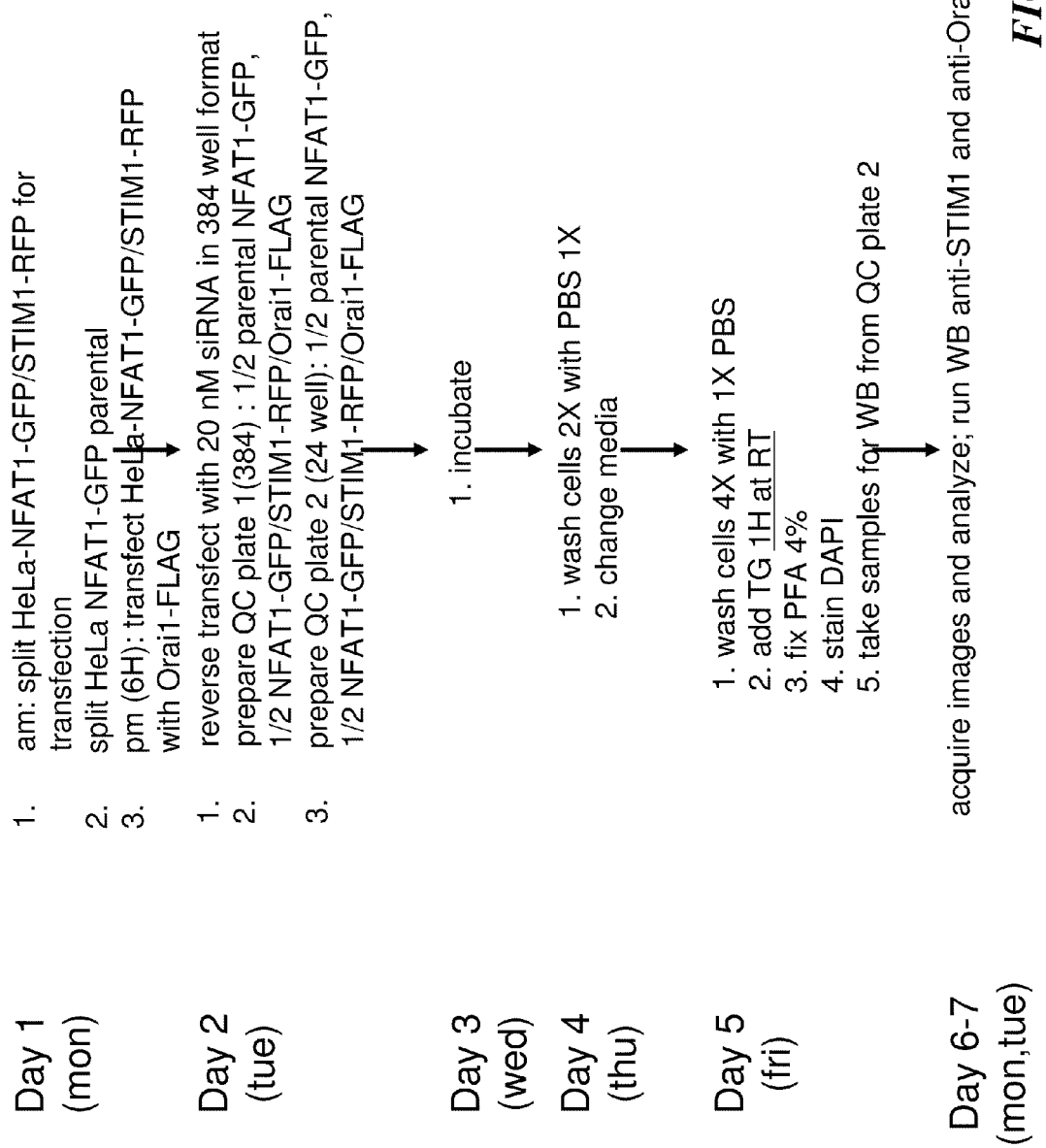
FIG. 8 shows a second flow diagram of the high-throughput screening protocol.
Figure 9:
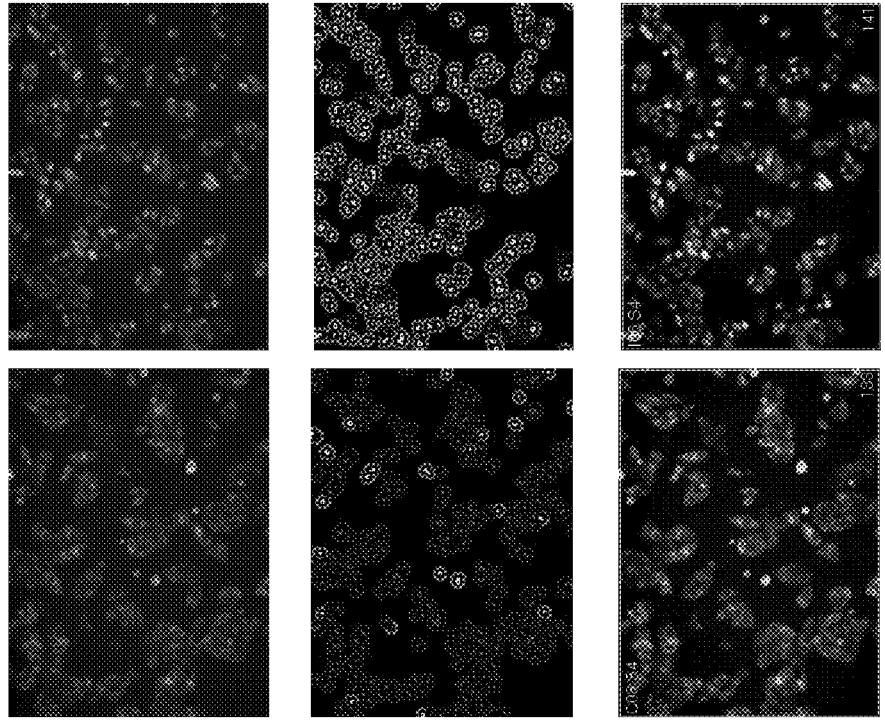
FIG. 9 shows the z score calculation for Hela cells transfected with STIM1 and Orai1.
Figure 11:
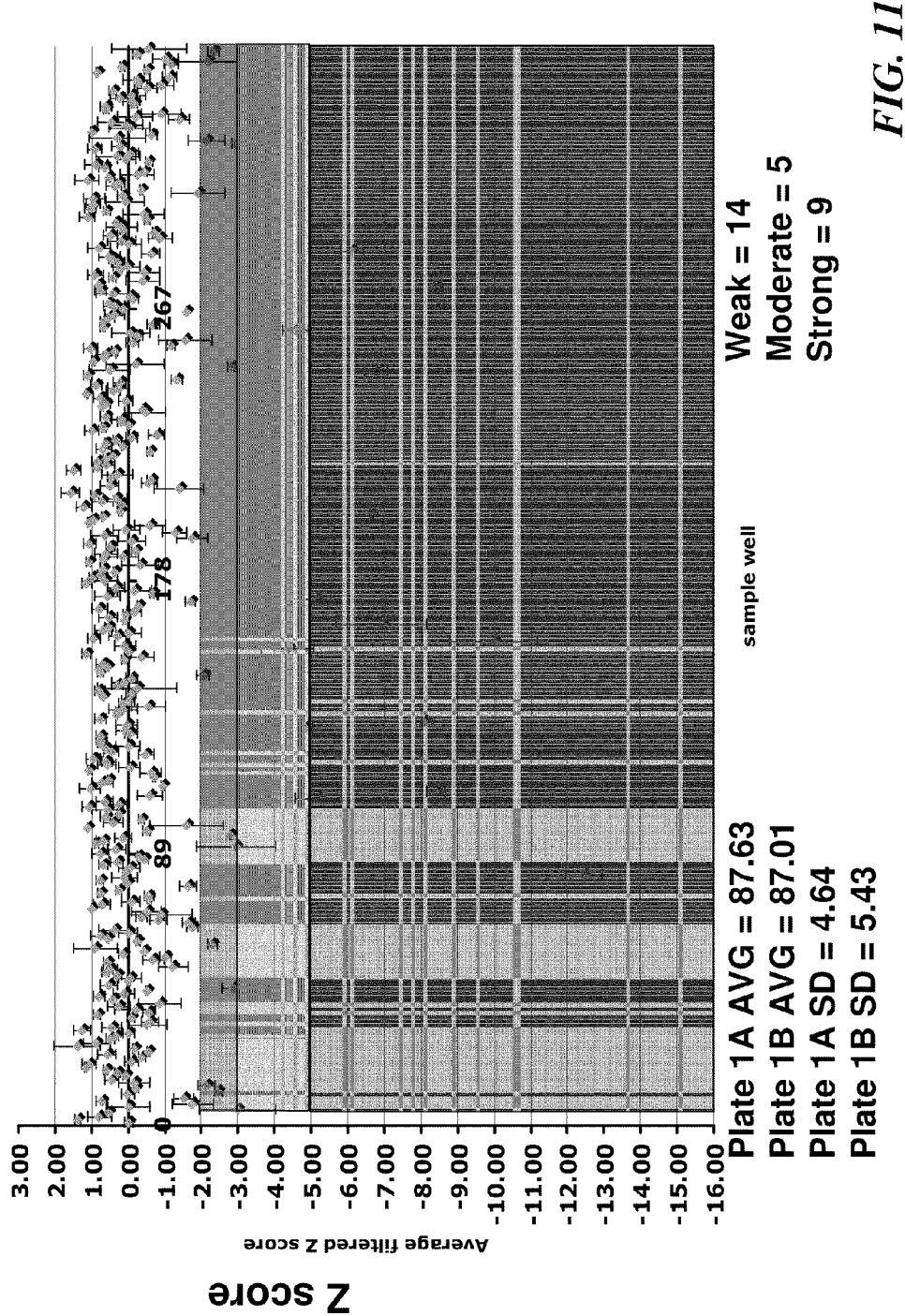
FIG. 11 shows the graph of average Z scores of kinases screened in a sample well of the HTS.
Figure 12:
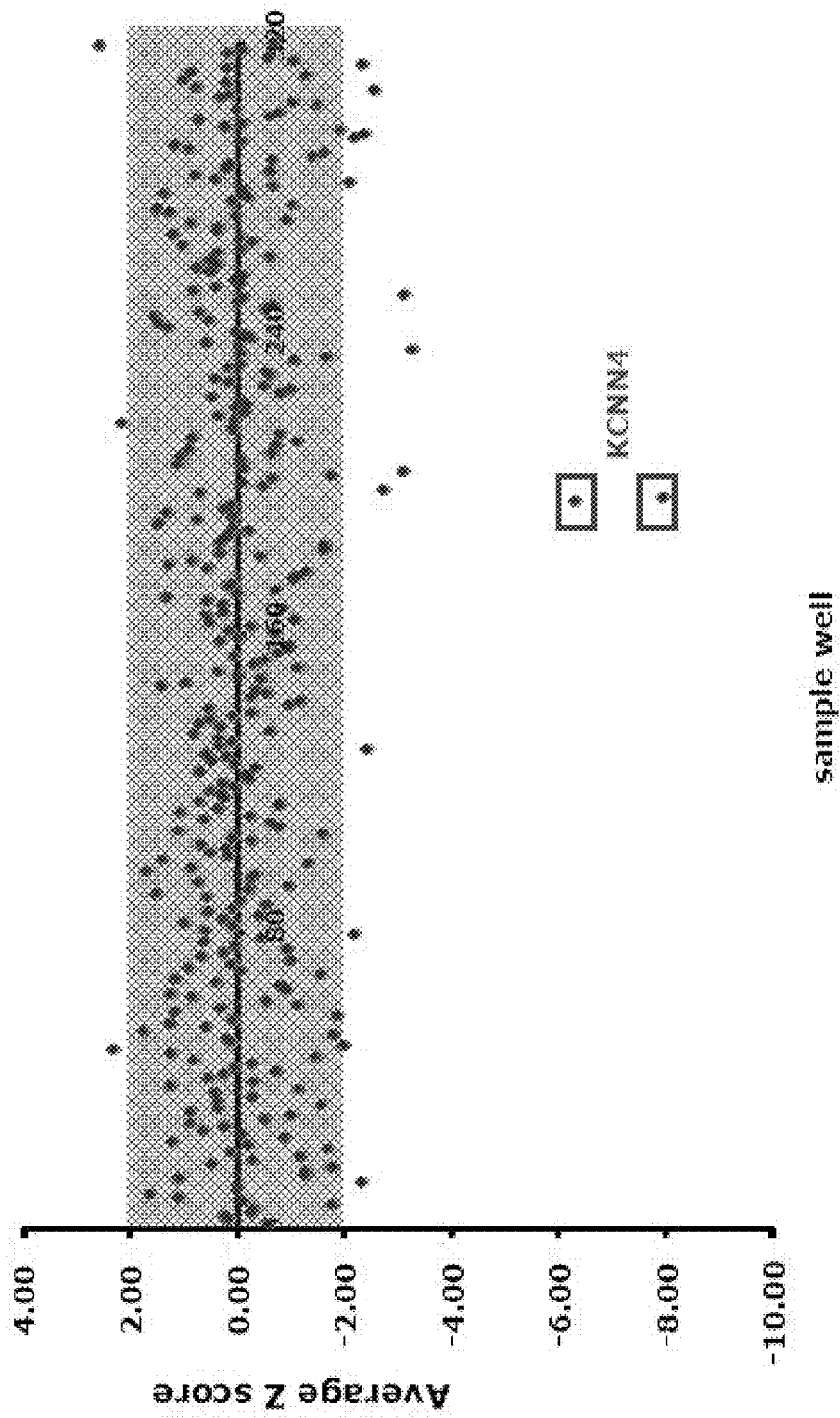
FIG. 12 shows the graph of the average Z scores of genes screened in the sample wells of the HTS plate #50048. Note that the duplicate Z-scores for KCNN4 (from duplicate wells) showing the knockdown of potassium channel KCNN4.
Figure 13:
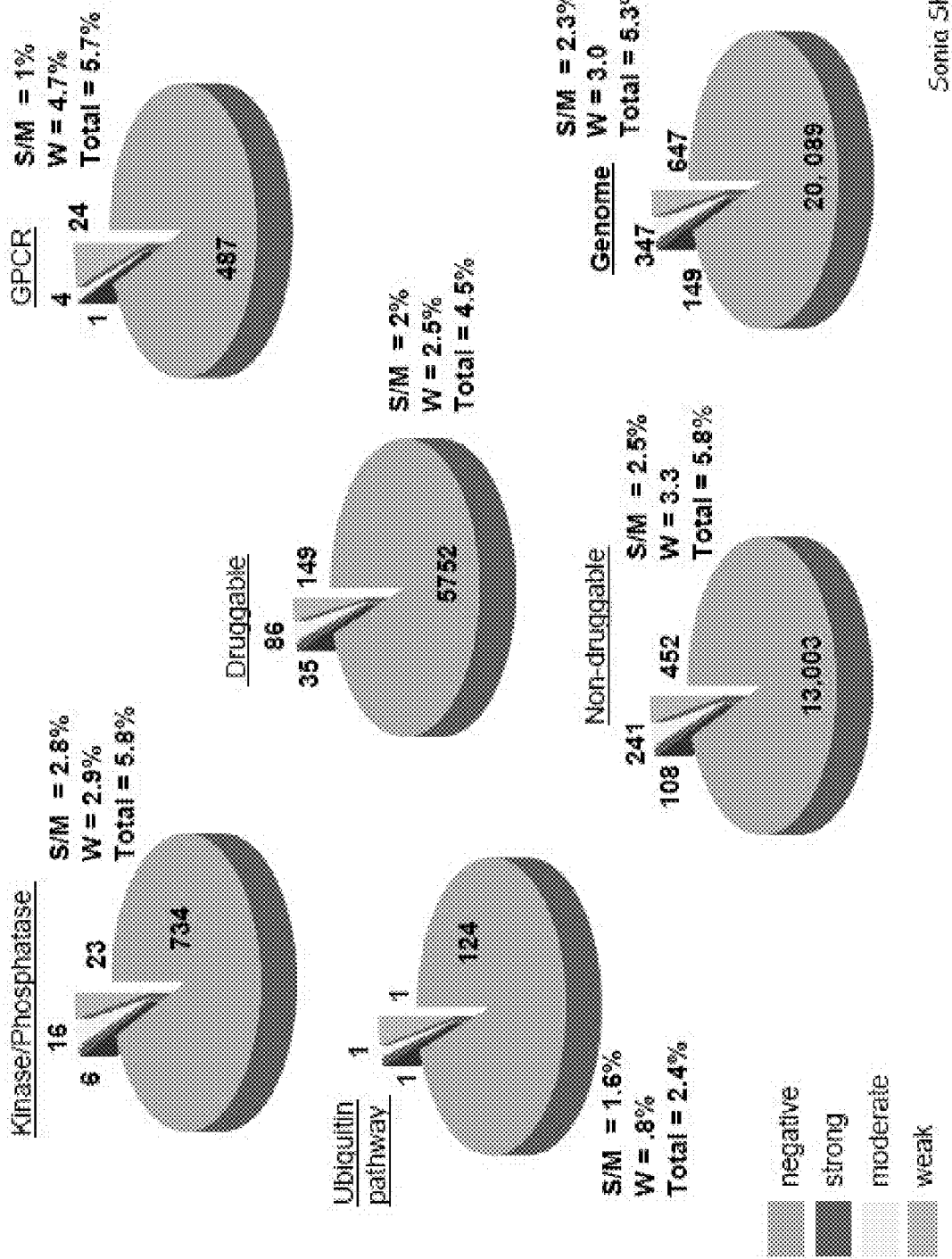
FIG. 13 shows the distribution and classification of the identified genes/proteins that modulate NFAT and/or store operated $Ca^{2+}$ entry (SOCE).
Figure 14:
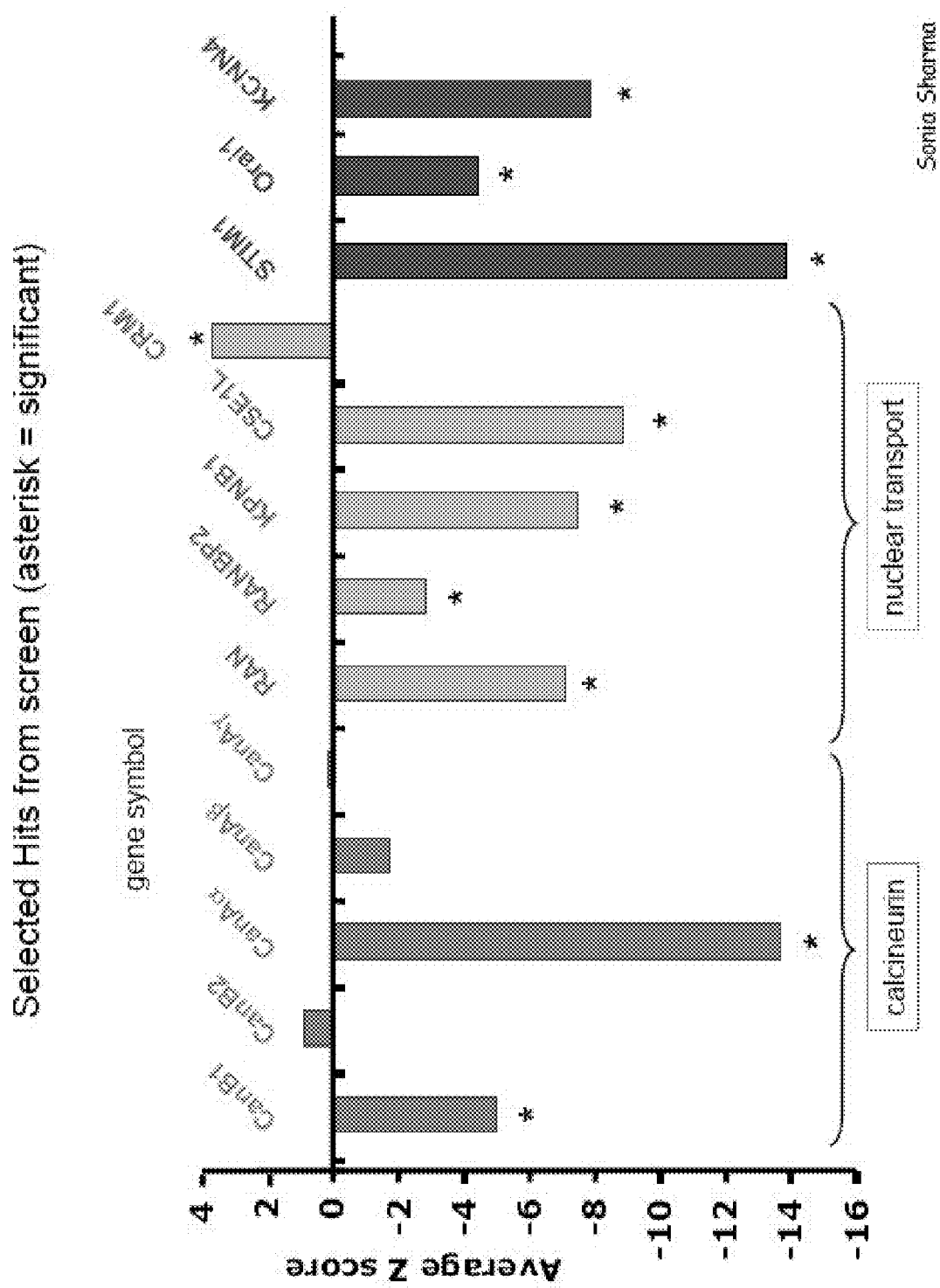
FIG. 14 shows the average Z score histogram of selected identified genes affecting NFAT.
Figure 15:
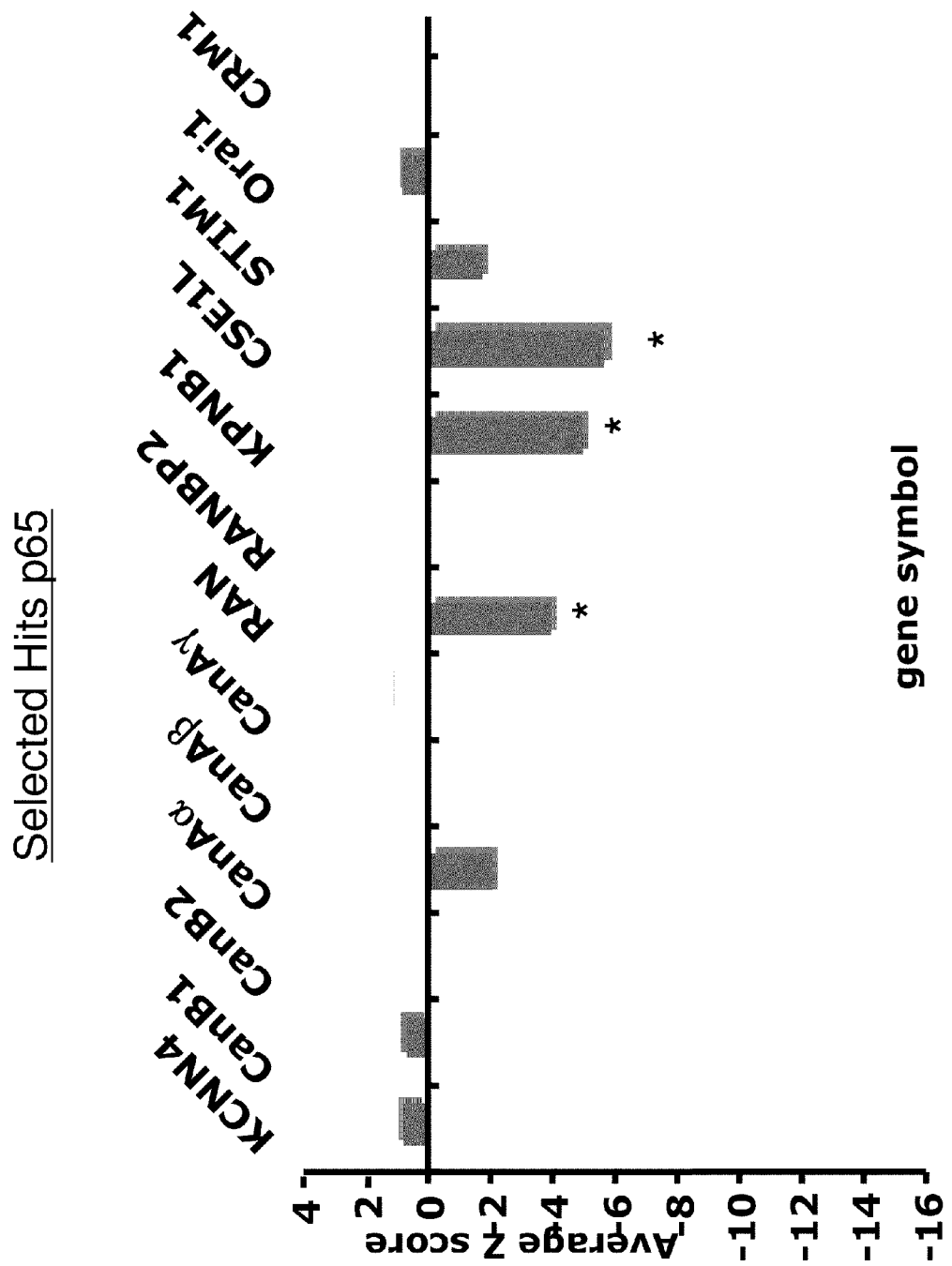
FIG. 15 shows the average Z score histogram of selected identified genes affecting p65.
Figure 18:
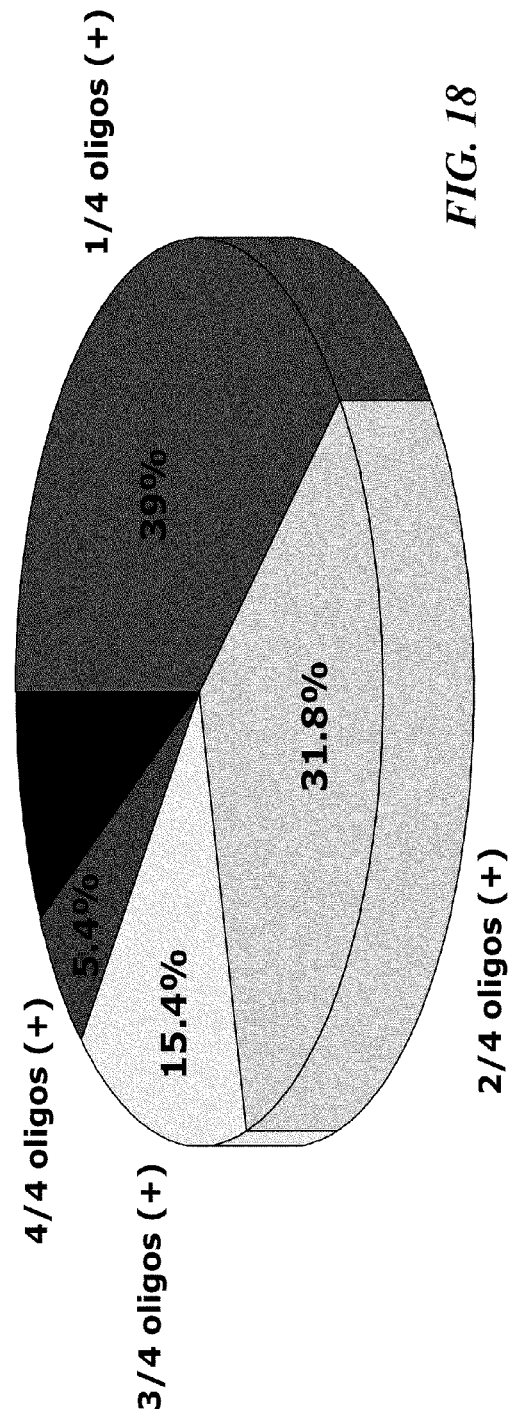
FIG. 18 shows the summary of the genes analyzed in the secondary screen.
Figure 21:
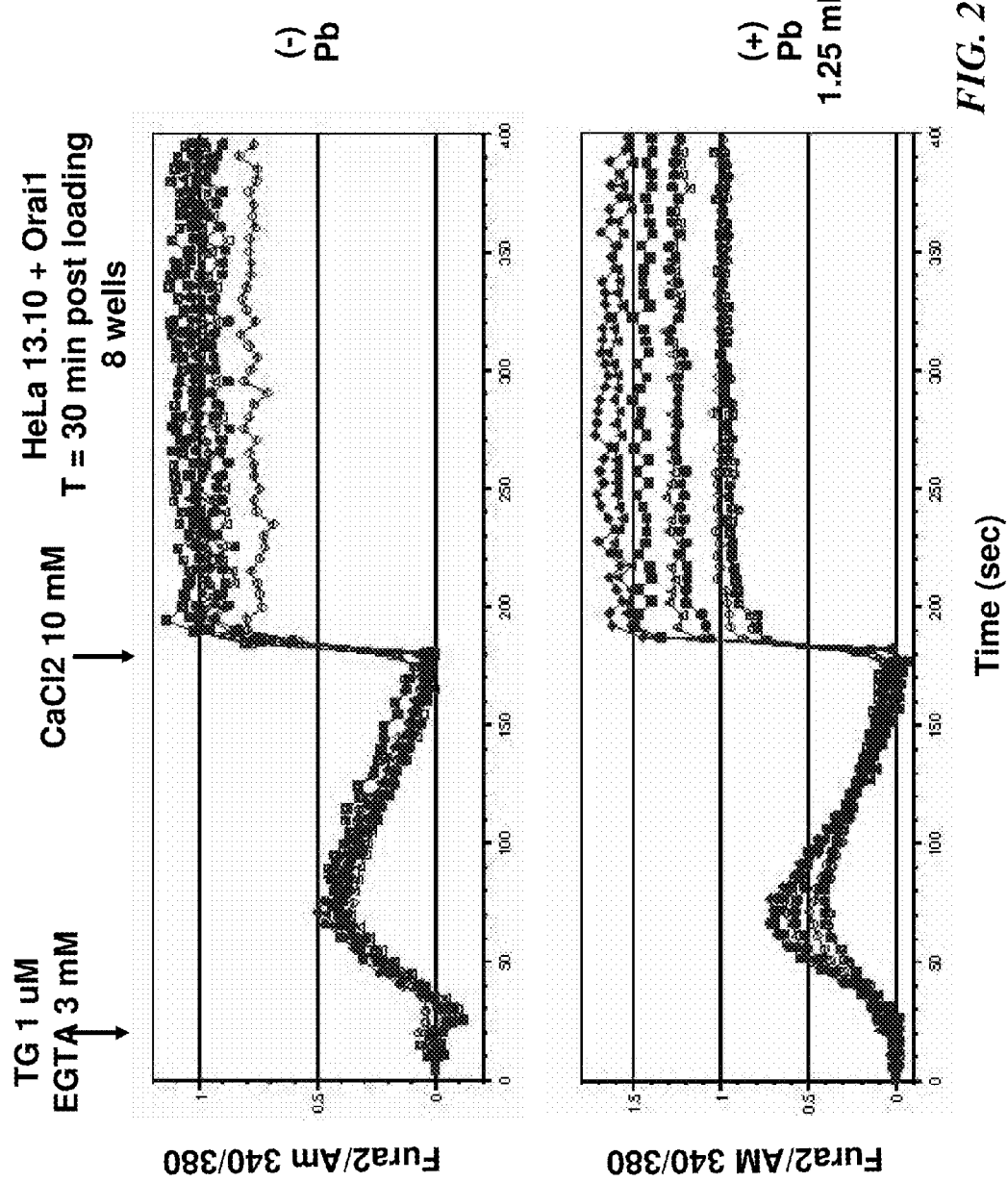
FIG. 21 shows eight reproducible traces of calcium fluxes in a tertiary screen in the presence (1.25 mM) or absence of lead (Pb).
Figure 22:
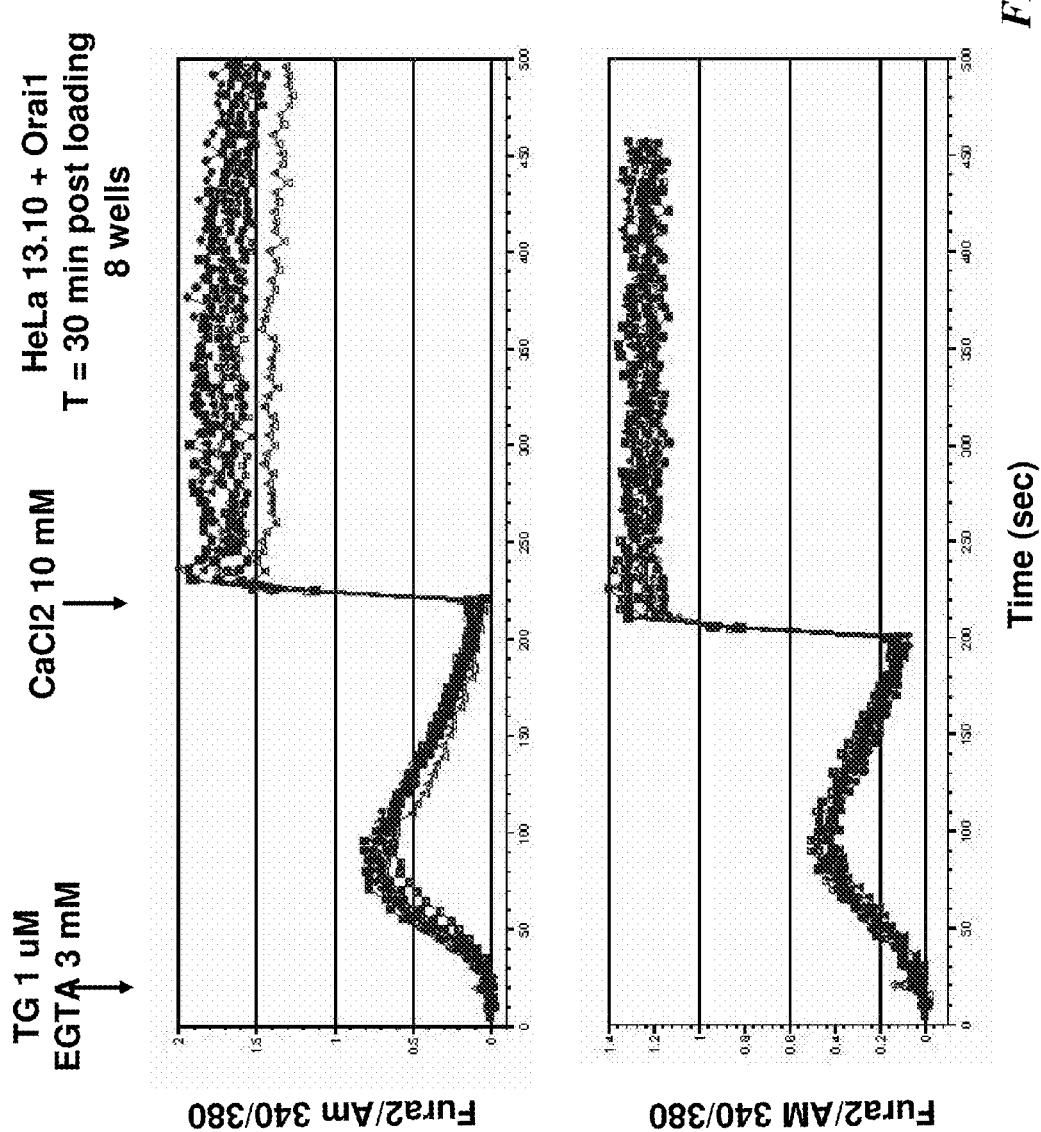
FIG. 22 shows eight reproducible traces of calcium fluxes in a tertiary screen at two different temperatures, at 37° C. and at room temperature (RT) (~25° C.).
Figure 23:
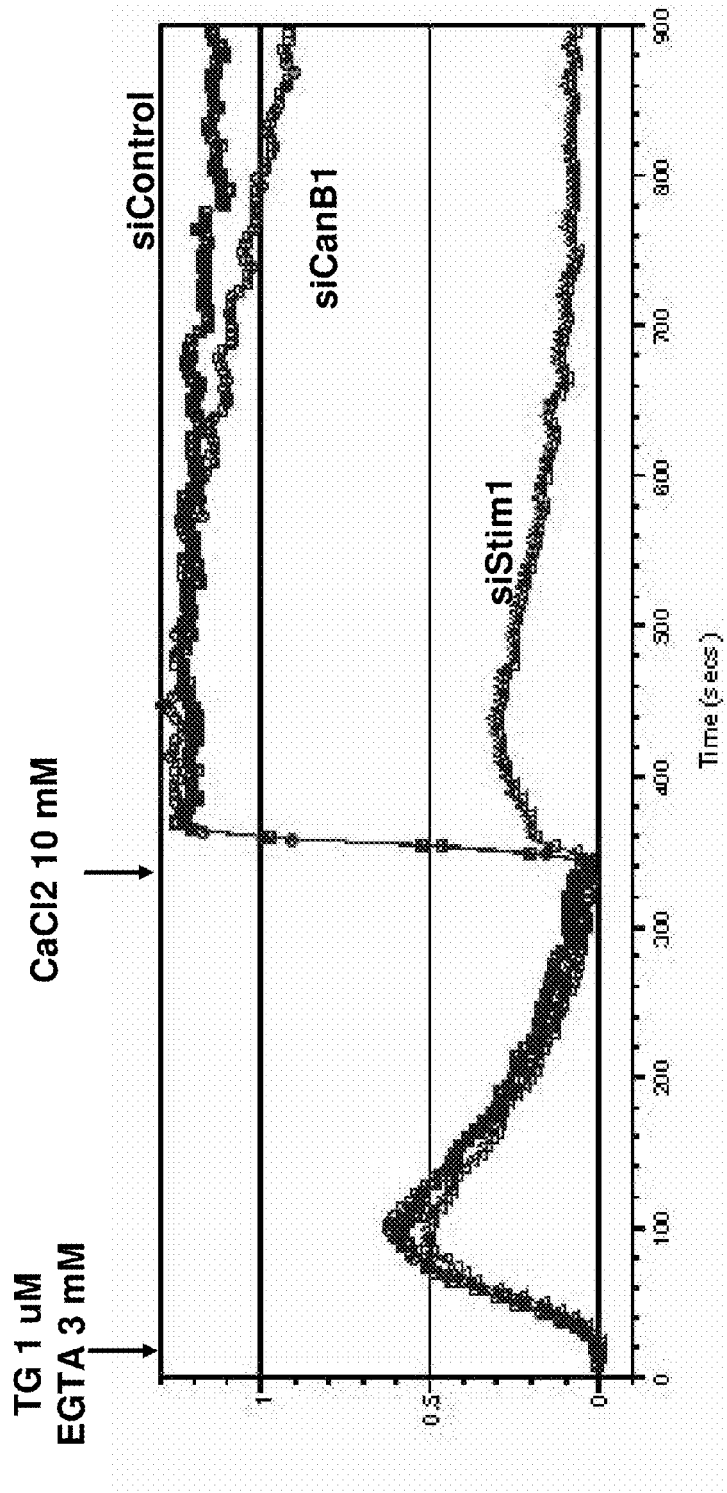
FIG. 23 shows additional traces of calcium fluxes in a tertiary screen at room temperature (RT) (~25° C.).
Figure 24:
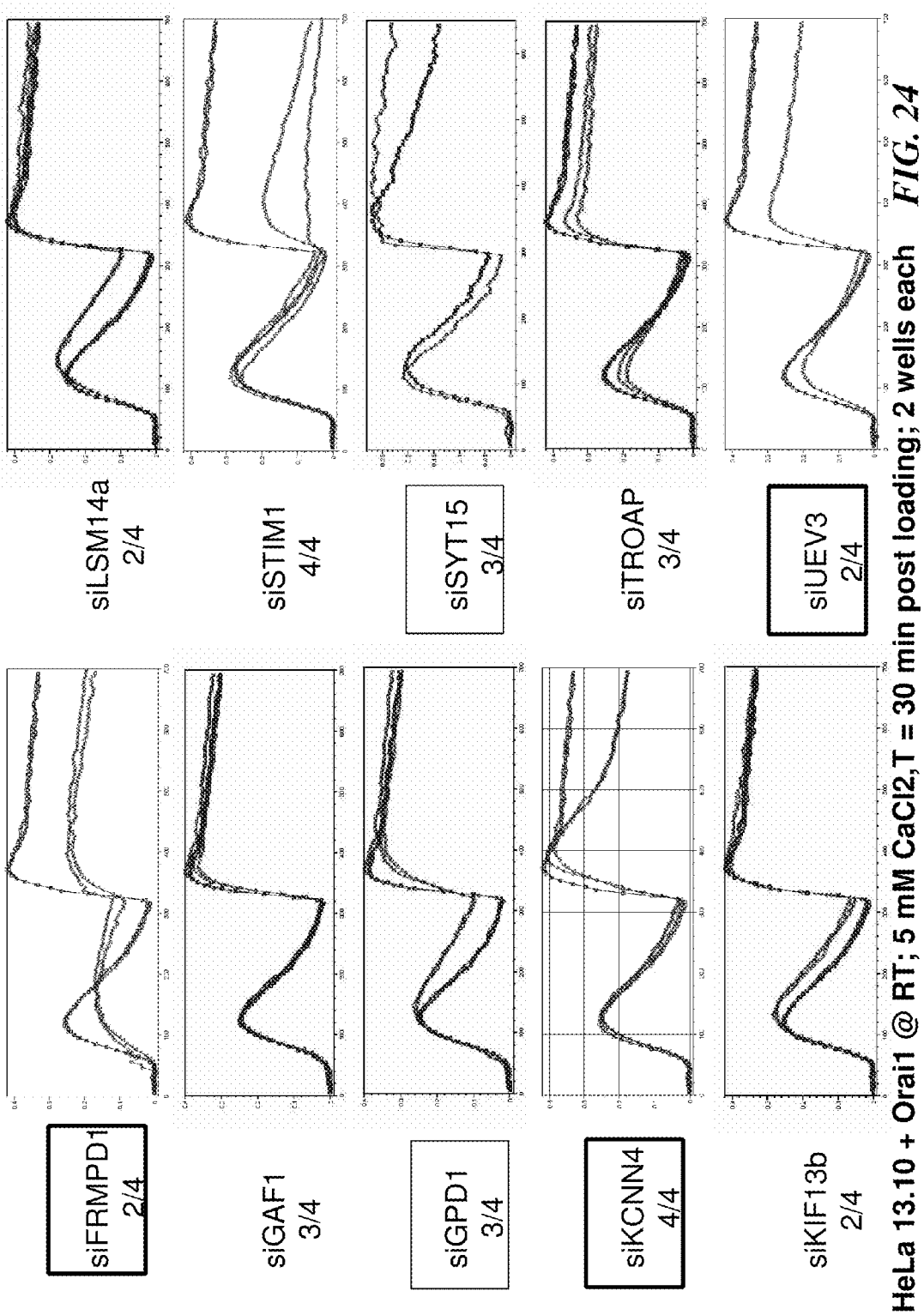
FIG. 24 shows additional traces of calcium fluxes in a tertiary screen.
Figure 26:
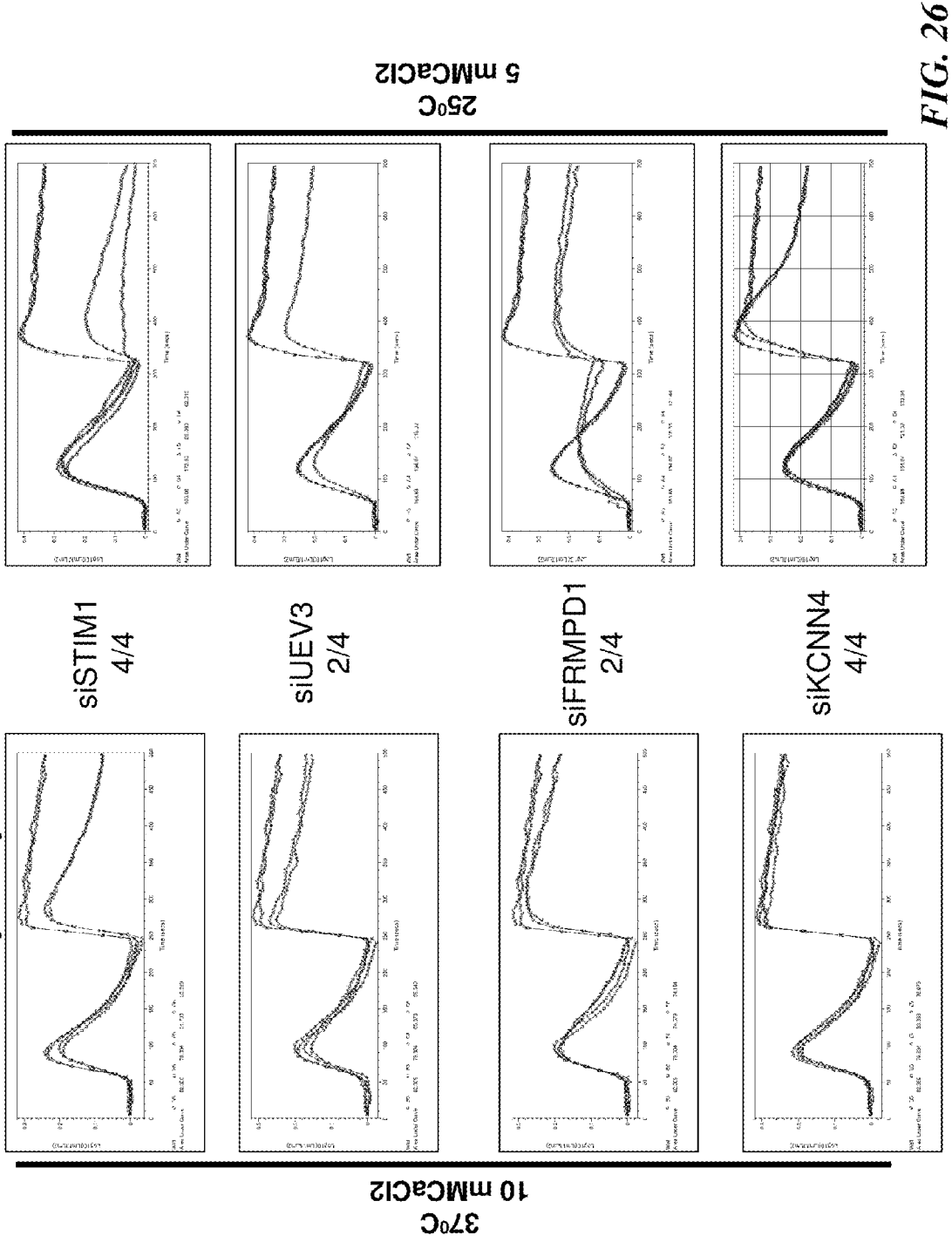
FIG. 26 shows additional traces of calcium fluxes of select hits in a tertiary screen at two different temperatures, at 37° C. and at room temperature (RT) (~25° C.).
Figure 27:
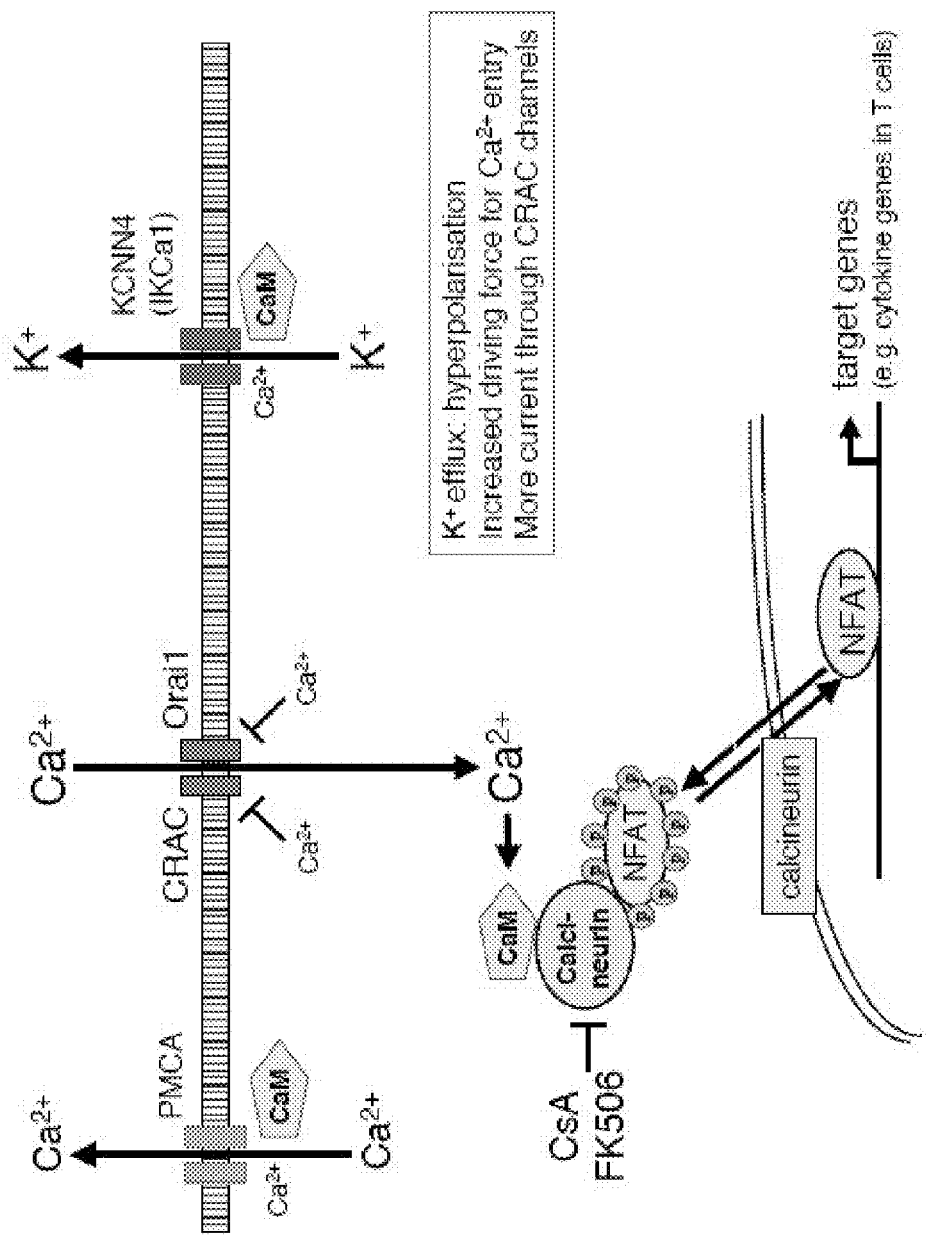
FIG. 27 shows the schematic diagram of mechanism of action of the potassium channel KCNN4 in relation to the intracellular $Ca^{2+}$ concentration and the regulation of NFAT nuclear translocation and cytokine production by intracellular $Ca^{2+}$ concentration.
Figure 28:
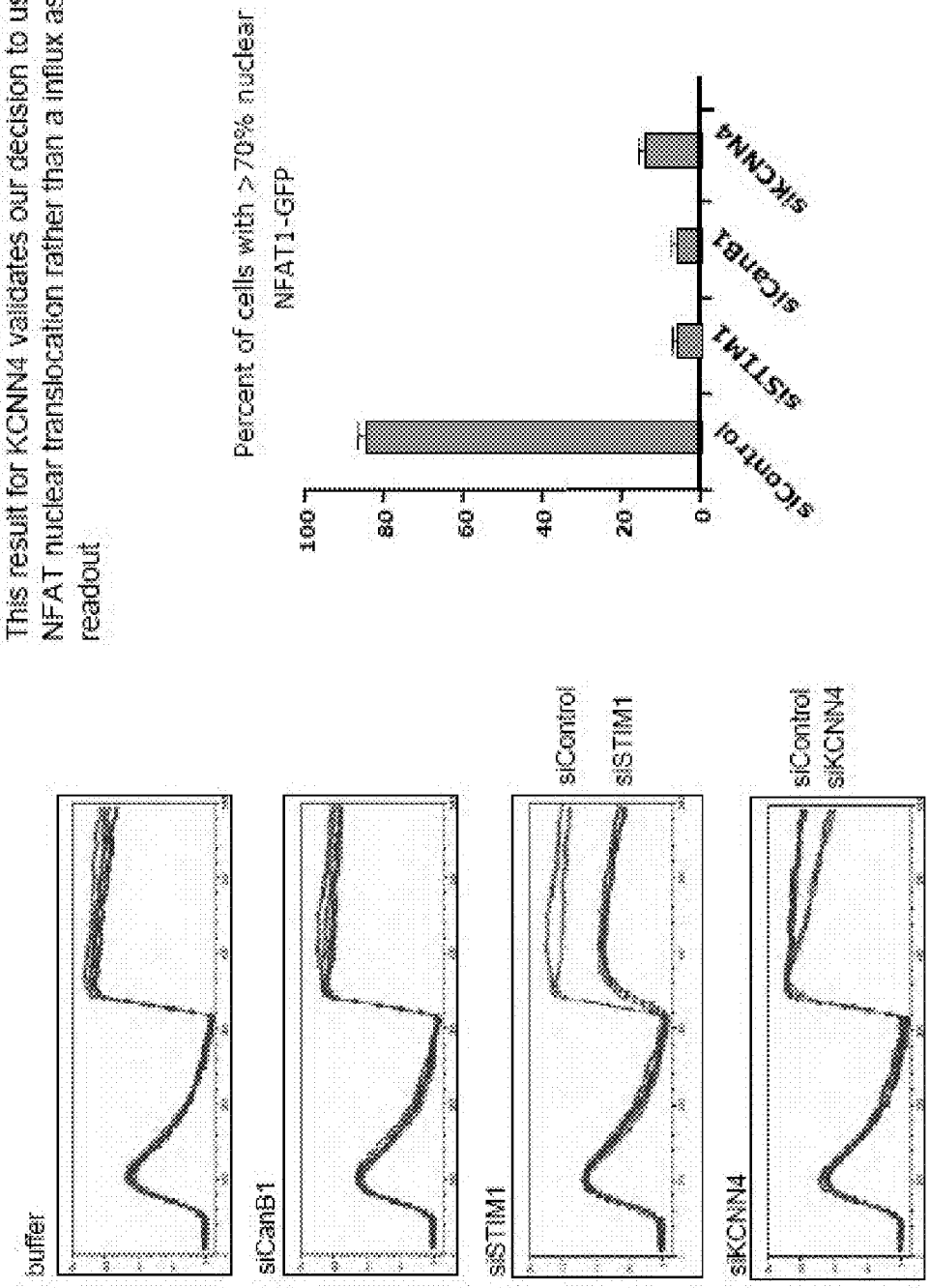
FIG. 28 shows the effects of siRNA of STIM1, CanB1, and KCNN4 on NFAT nuclear translocation. The figure also shows that siRNA CanB1 has not effect on $Ca^{2+}$ influx in contrast to the siRNA of STIM1 and KCNN4.
Figure 29:
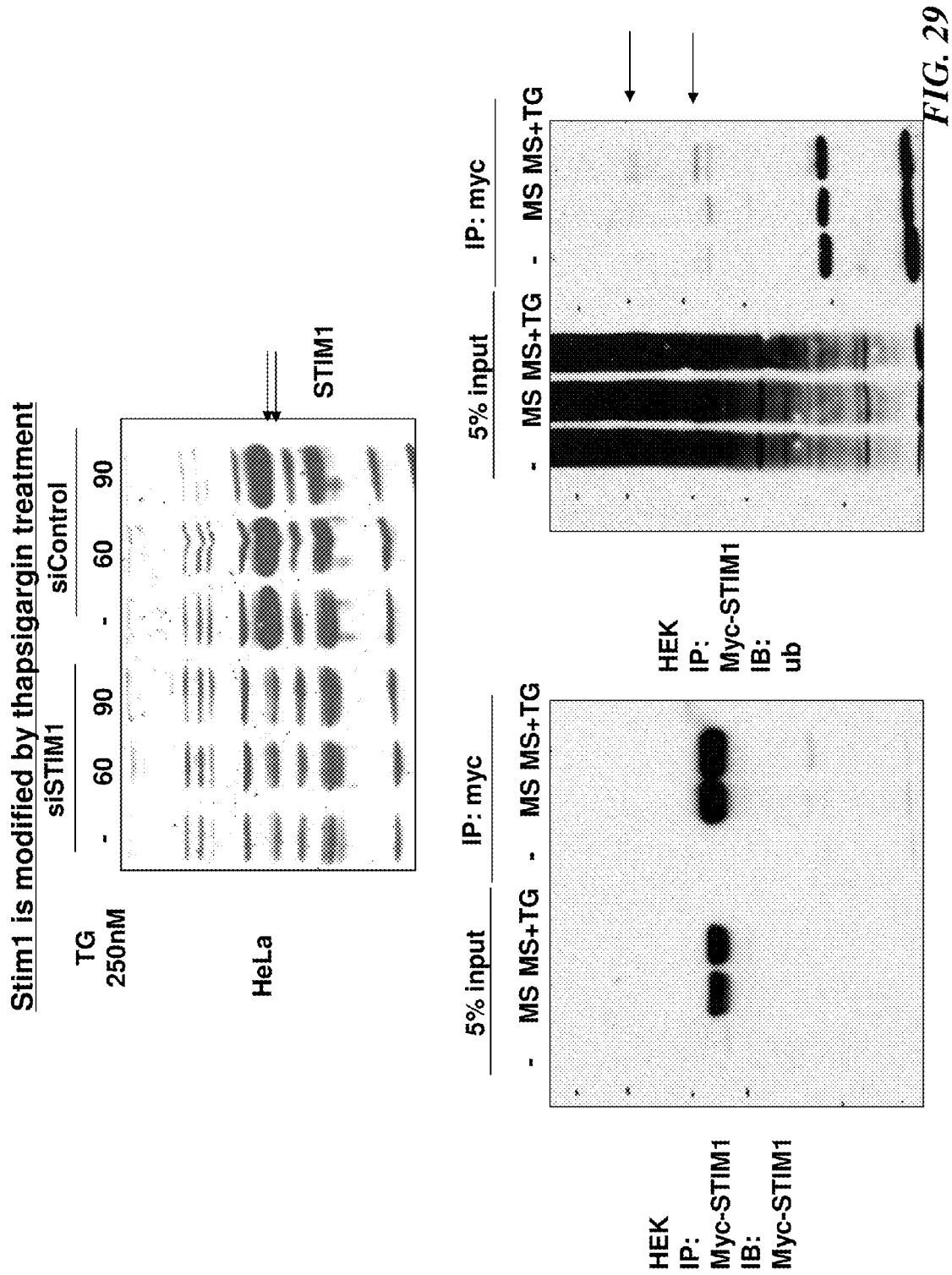
FIG. 29 shows that Stim1 is modified by thapsigargin treatment.
Figure 30:
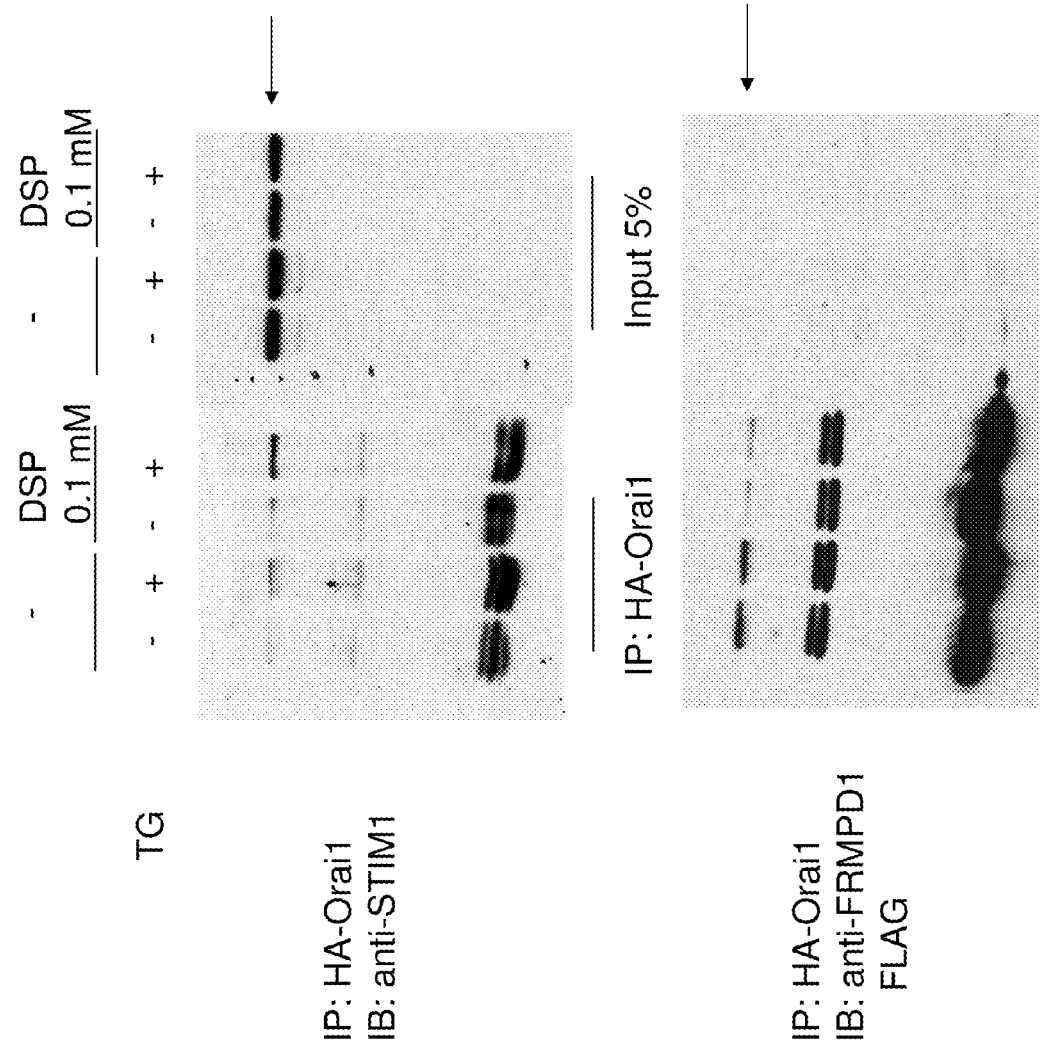
FIG. 30 shows that cross-linking enhances STIM1-Orai1 interaction.
Figure 33:
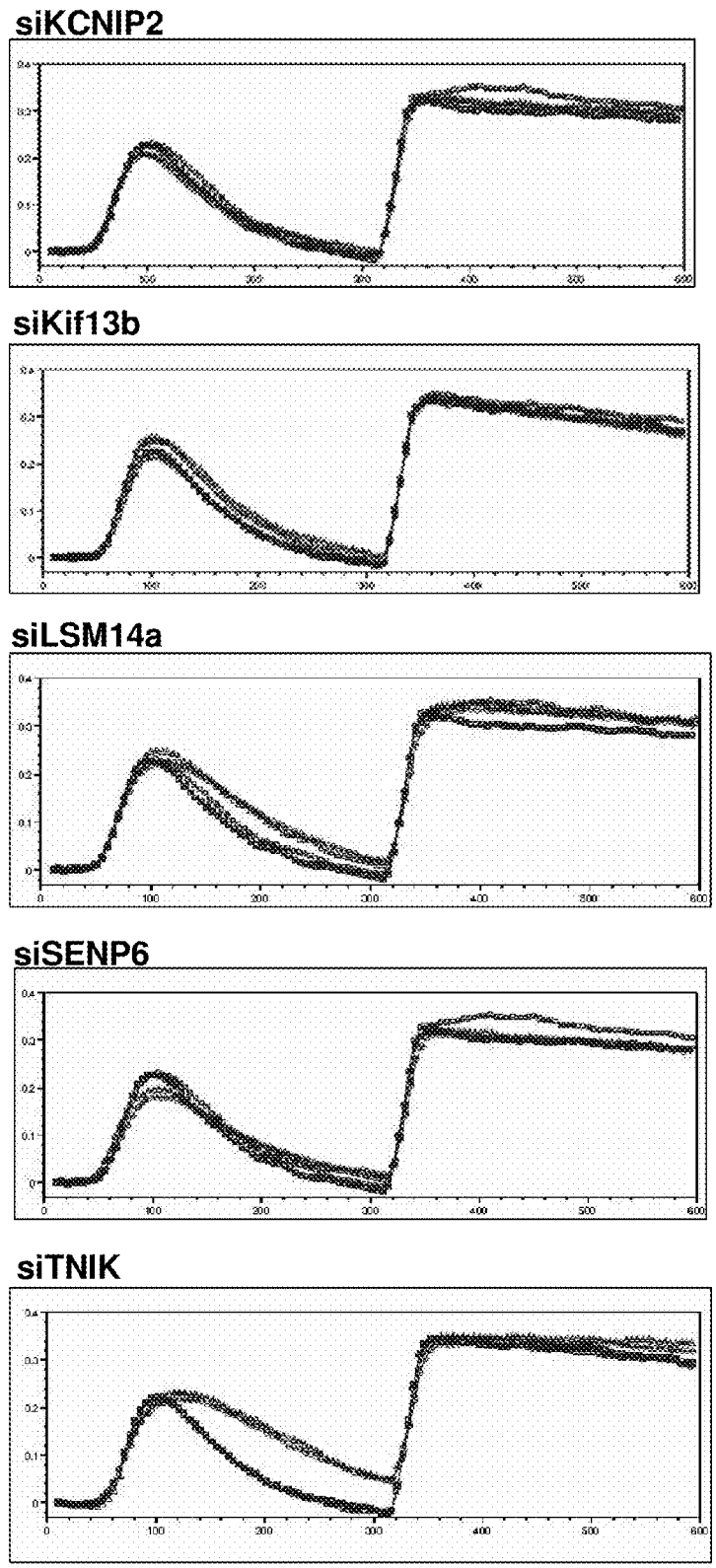
FIG. 33 shows some traces of calcium fluxes of cells with siRNA to select hits.
Figure 34:
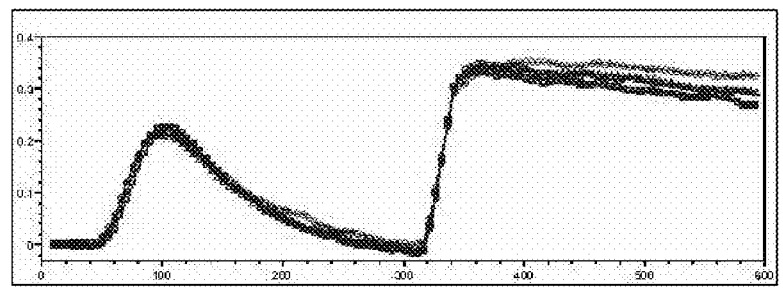
FIG. 34 shows some traces of calcium fluxes of cells with siRNA to TROAP
Figure 35:
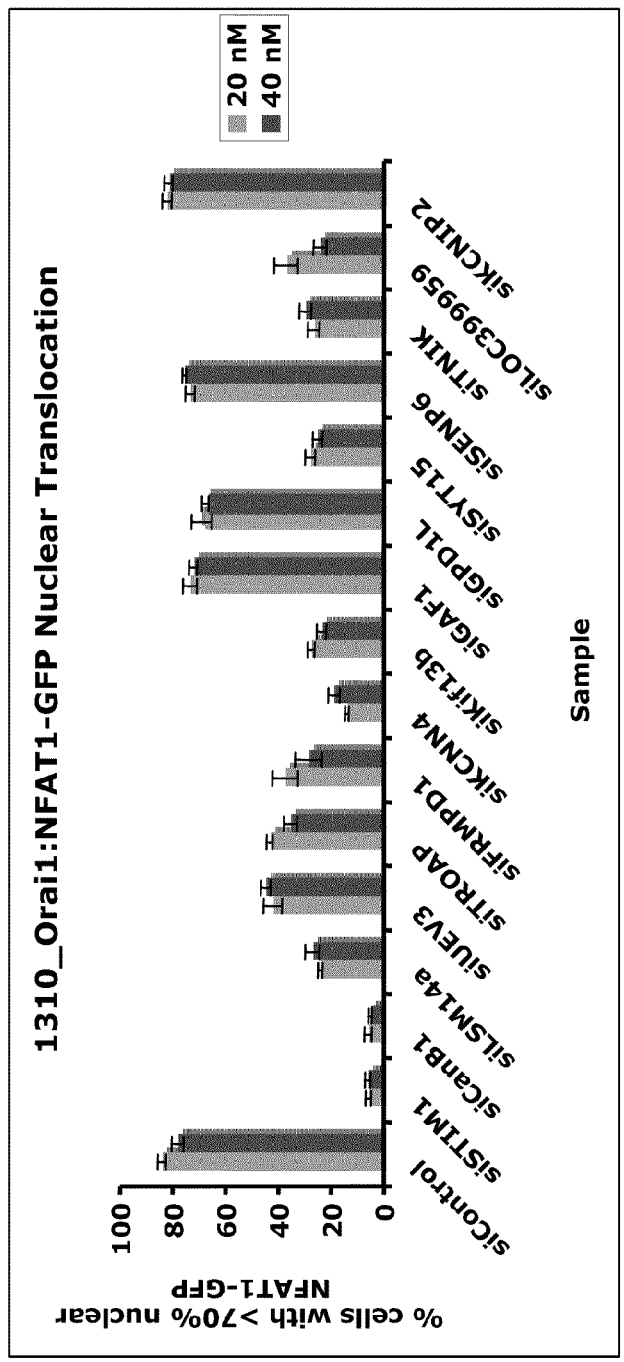
FIG. 35 shows genes that enhances NFAT-GFP nuclear localization.
Figure 36:
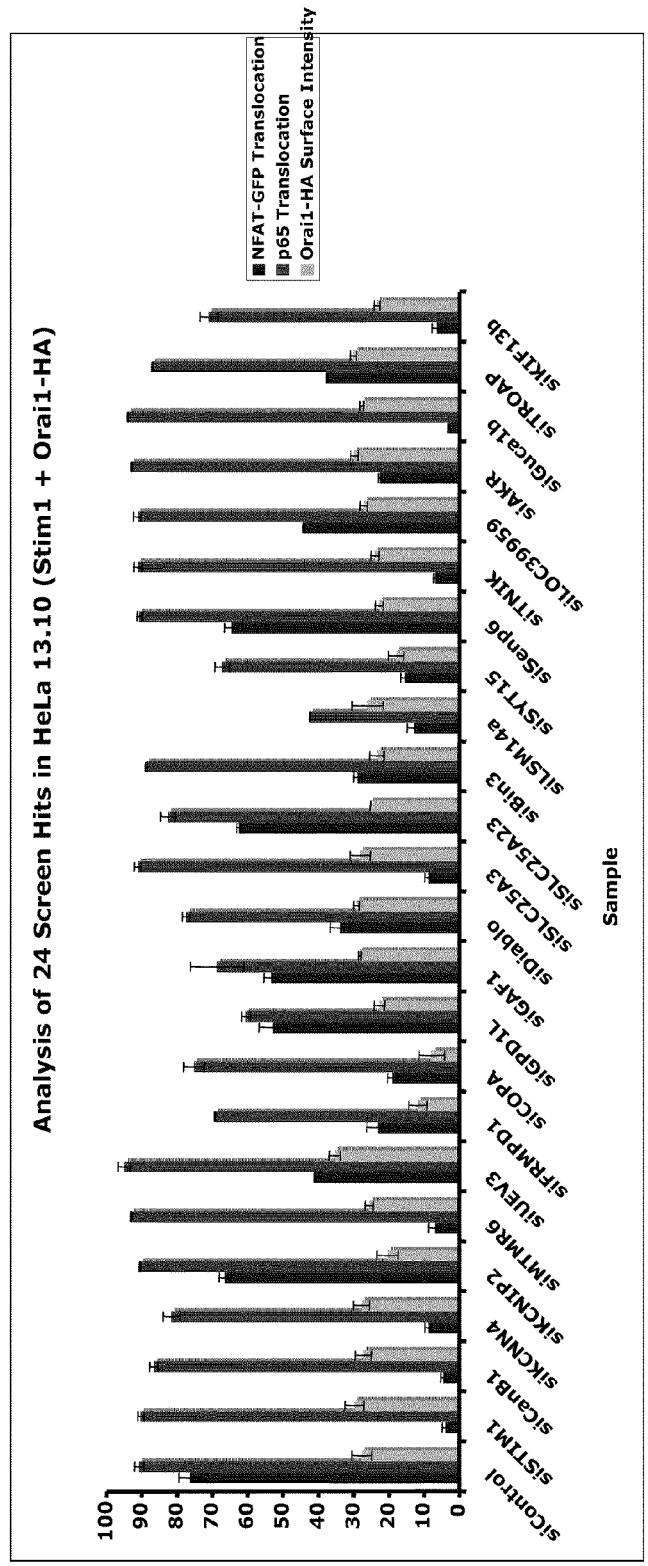
FIG. 36 is a summary of genes that affects NFAT-GFP nuclear localization, p65 translocation and Orai1 cell surface localization.
Figure 37:
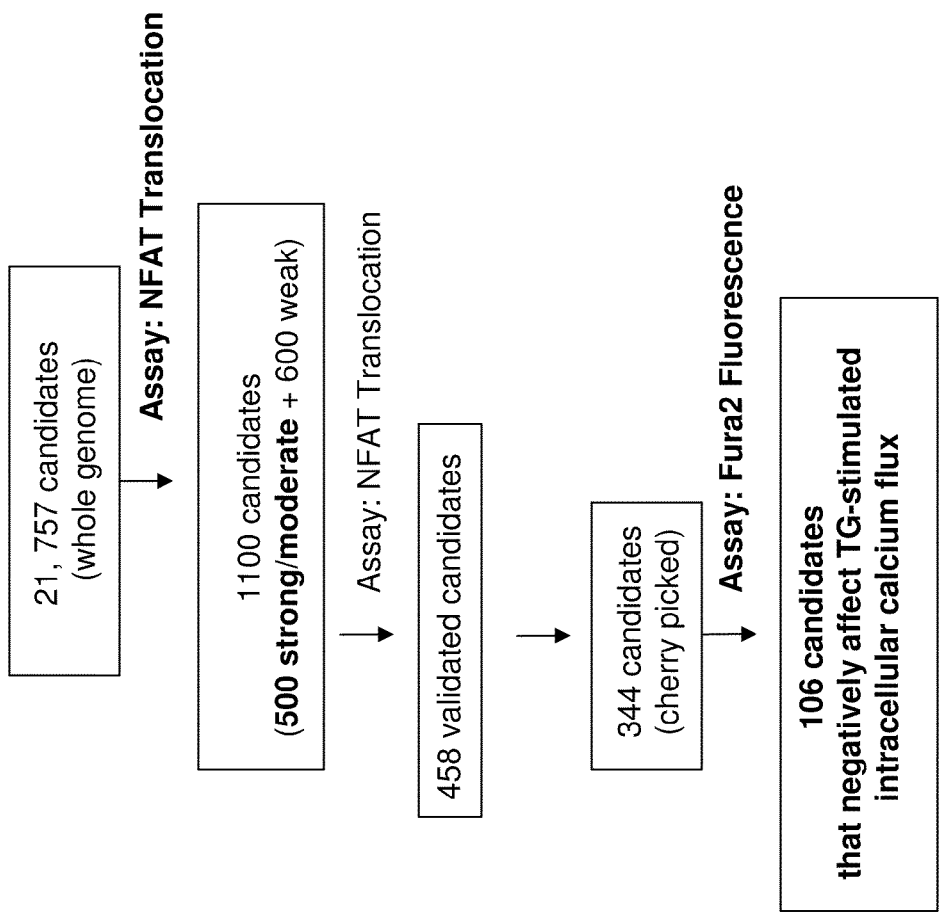
FIG. 37 shows the summary of primary, secondary and tertiary screens.

Unless otherwise explained, all technical and scientific terms used herein have the same meaning as commonly understood by one of ordinary skill in the art to which this disclosure belongs. Definitions of common terms immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise stated, the present invention was performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987), Current Protocols in Molecular Biology (CPMB) (Fred M. Ausubel, et al. ed., John Wiley and Sons, Inc), Current Protocols in Protein Science (CPPS) (John E. Coligan, et. al., ed., John Wiley and Sons, Inc.), Current Protocols in Cell Biology (CPCB) (Juan S. Bonifacino et. al.

ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol 57, Jennie P. Mather and David Barnes editors, Academic Press, 1st edition, 1998) which are all incorporated by reference herein in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

All patents and other publications cited throughout this application are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

DEFINITIONS OF TERMS

The term "NFAT activation" refers to the nuclear translocation of NFAT from the cytoplasm to the nucleus. Nuclear factor of activated T-cells (NFAT) is a general name applied to a family of transcription factors shown to be important in immune response. Cytoplasmic NFAT proteins are phosphorylated. To enter the nucleus, NFAT has to be dephosphorylated. Activated serine/threonine phosphatase calcineurin rapidly dephosphorylates the serine rich region (SRR) and SP-repeats in the amino termini of NFAT proteins resulting in a conformational change that exposes a nuclear localization signal resulting in NFAT nuclear import. The term "NFAT activity" also means the nuclear translocation of NFAT from the cytoplasm to the nucleus.

As used herein, the term "pharmaceutical composition" refers to an active agent in combination with a pharmaceutically acceptable carrier of chemicals and compounds commonly used in the pharmaceutical industry. The term "pharmaceutically acceptable carriers" excludes tissue culture medium.

As used herein, the term "therapeutically effective amount" refers to that amount of active agent that can reduce the activity of a candidate protein by at least 5% or the expression of a gene identified in Table 1, 2 or 3 by at least 5%. The term also means a reduction of at least 5% in NFAT-GFP nuclear localization and/or SOCE and/or cytokine production in the cell-based assay as described herein or other methods that are known to one skilled in the art. The term also means providing "effective" treatment as that term is defined herein. An effective amount as used herein would also include an amount sufficient to prevent or delay the development of a symptom of the disease, alter the course of a symptom disease (for example but not limited to, slow the progression of a symptom of the disease), or reverse a symptom of the disease.

As used herein, the term "treat" or treatment" refers to reducing or alleviating at least one adverse effect or symptom associated with medical conditions that are associated with hyperactive or inappropriately active immune system. These include reducing the amount of cytokine production, suppression of T cell activation and proliferation, suppression of the immune system, and reducing inflammation.

As used herein, the terms "administering," and "introducing" are used interchangeably and refer to the placement of the agents that inhibit gene identified in Table 1, 2 or 3s as disclosed herein into a subject by a method or route which results in at least partial localization of the agents at a desired site. The pharmaceutical compositions of the present invention can be administered by any appropriate route which results in an effective treatment in the subject.

The term "agent" refers to any entity which is normally not present or not present at the levels being administered, in the cell. Agents for use in the invention include, but are not limited to chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc. A protein and/or peptide or fragment thereof can be any protein of interest, for example, but are not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein inhibitor of gene identified in Table 1, 2 or 3 within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The term "inhibiting" as used herein as it pertains to the expression or activity of the protein or polypeptide of genes identified in Table 1, 2 or 3. The term does not necessarily mean complete inhibition of expression and/or activity. Rather, expression or activity of the protein, polypeptide or polynucleotide is inhibited to an extent, and/or for a time, sufficient to produce the desired effect, for example, reduced nuclear translocation of NFAT. In particular, inhibition of expression or activity of a gene from Table 1, 2 or 3 can be determined using an assay such as the bioassay for the protein encoded by the gene, for example, western blot analysis for the detection and quantification of expressed protein. Agents that inhibit the genes of Table 1, 2 or 3 are agents that inhibit the protein function and/or genes expression by at least 5%.

As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" and "RNA interfering" with respect to an agent of the invention, are used interchangeably herein.

As used herein an "siRNA" refers to a nucleic acid that forms a double stranded RNA, which double stranded RNA has the ability to reduce or inhibit expression of a gene or target gene when the siRNA is present or expressed in the same cell as the target gene, for example RANBP2. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et at Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116: 281-297), comprises a dsRNA molecule.

As used herein, the term "complementary base pair" refers to A:T and G:C in DNA and A:U in RNA. Most DNA consists of sequences of nucleotide only four nitrogenous bases: base or base adenine (A), thymine (T), guanine (G), and cytosine (C). Together these bases form the genetic alphabet, and long ordered sequences of them contain, in coded form, much of the information present in genes. Most RNA also consists of sequences of only four bases. However, in RNA, thymine is replaced by uridine (U).

As used herein, the term "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA, ribosomal DNA and cDNA. Other suitable nucleic acid molecules are RNA, including mRNA, rRNA and tRNA. The nucleic acid molecule can be naturally occurring, as in genomic DNA, or it may be synthetic, ie., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

The term "vector", as used herein, refers to a nucleic acid construct designed for delivery to a host cell or transfer between different host cells. As used herein, a vector can be viral or non-viral.

As used herein, the term "expression vector" refers to a vector that has the ability to incorporate and express heterologous nucleic acid fragments in a cell. An expression vector may comprise additional elements, for example, the expression vector may have two replication systems, thus allowing it to be maintained in two organisms, for example in human cells for expression and in a prokaryotic host for cloning and amplification.

As used herein, the term "heterologous nucleic acid fragments" refers to nucleic acid sequences that are not naturally occurring in that cell. For example, when a human RANBP2 gene is inserted into the genome of a bacteria or virus, that human RANBP2 gene is heterologous to that recipient bacteria or virus because the bacteria and viral genome do not naturally have the human RANBP2 gene.

As used herein, the term "viral vector" refers to a nucleic acid vector construct that includes at least one element of viral origin and has the capacity to be packaged into a viral vector particle. The viral vector can contain the shRNA for the human RANBP2 in place of non-essential viral genes. The vector and/or particle may be utilized for the purpose of transferring any nucleic acids into cells either in vitro or in vivo. Numerous forms of viral vectors are known in the art.

The term "replication incompetent" as used herein means the viral vector cannot further replicate and package its genomes. For example, when the cells of a subject are infected with replication incompetent recombinant adeno-associated virus (rAAV) virions, the heterologous (also known as transgene) gene is expressed in the patient's cells, but, the rAAV is replication defective (e.g., lacks accessory genes that encode essential proteins from packaging the virus) and viral particles cannot be formed in the patient's cells.

The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments. The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "subject" as used herein includes, without limitation, a human, mouse, rat, guinea pig, dog, cat, horse, cow, pig, monkey, chimpanzee, baboon, or rhesus. In one embodiment, the subject is a mammal. In another embodiment, the subject is a human.

As used herein, the term "comprising" means that other elements can also be present in addition to the defined elements presented. The use of "comprising" indicates inclusion rather than limitation.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

As used herein, the term "modulate" means the regulation of the cellular activity of a protein. Modulation can mean up regulation of the cellular activity of the protein, whereby its activity is enhances and/or promoted. Modulation can also mean down regulation of the cellular activity of the protein, whereby its activity is reduced, blocked, and/or prevented.

As used herein, the term "a neoplastic cell proliferation disorder" refers to any disorder that is characterized by deregulated or unregulated cell proliferation that arises from a stem cell. A normal stem cell may be transformed into a cancer stem cell through disregulation of the proliferation and differentiation pathways controlling it. Examples include but are not limited to cancer and tumors formation.

As used herein, the term "tumor" refers to a mass of transformed cells that are characterized, at least in part, by containing angiogenic vasculature. The transformed cells are characterized by neoplastic uncontrolled cell multiplication which is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

As used herein, the term "metastases" or "metastatic tumor" refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location. As used herein, a "malignant tumor" is one having the properties of invasion and metastasis and showing a high degree of anaplasia. Anaplasia is the reversion of cells to an immature or a less differentiated form, and it occurs in most malignant tumors.

The term "therapy resistant cancer" as used herein refers to a cancer present in a subject who is resistant to, or refractory to at least two different anti-cancer agents such as chemotherapy agents, which means, typically a subject has been treated with at least two different anti-cancer agents that did not provide effective treatment as that term is defined herein.

Embodiments of the invention are based on the discovery of several hundred genes in the human and mouse genomes whose gene products directly and/or indirectly modulate NFAT activation and/or modulate the store-operated $Ca^{2+}$ entry (SOCE) into the cell. The inventors developed a cell-based reporter system for screening for modulators of nuclear factors of activated T cells (NFAT) and/or store-operated $Ca^{2+}$ entry into a cell. The cell-based reporter system comprises a mammalian cell co-expressing a NFAT-GFP, a STIM1-RFP, and a Orai1-FLAG. The markers: GFP, REP and FLAG-tag facilitate the visual localization of the respectively expressed proteins within the cell compartments. For example, whether NFAT is localized to the cytoplasm under non-$Ca^{2+}$ depletion conditions (in the absence of thapsigargin (TG)) or has translocated to the nucleus upon treatment with TG, and whether STIM1/Orai1 are expressed and properly localized to the membranes. TG is a tight-binding inhibitor of a class of enzymes known by the acronym SERCA, which stands for sarco/endoplasmic reticulum $Ca^{2+}$ ATPase. TG raises cytosolic calcium concentration by blocking the ability of the cell to pump calcium into the sarcoplasmic and endoplasmic reticula which causes these stores to become depleted. Store-depletion can secondarily activate plasma membrane calcium channels, triggering store-operated $Ca^{2+}$ entry into a cell via plasma membrane channels. It was found that the co-expression of STIM1-RFP, and Orai1-FLAG in Hela cells enhanced SOCE in these cells upon TG treatment. The inventors used the cytoplasm-to-nuclear translocation of NFAT-GFP as their assay readout, counting the number of cells that have nuclear GFP fluorescence after TG treatment. For a population of these cells treated with TG, a mean number of cells will have NFAT-GFP nuclear localization after TG treatment for a fixed period of time, e.g. 10 minutes. This is the control population for the high-throughput screen. Within this population data, a standard deviation is also obtained. The data (number of cells having NFAT-GFP nuclear localization after TG treatment) is assumed to have a normal distribution. This data of this control population of cells are normalized to a standard normal distribution, which has a mean of 0 (the mean number of cell with nuclear NFAT-GAT) and standard deviation of 1.

To screen for modulators of NFAT and/or store-operated $Ca^{2+}$ entry into a cell, the inventors performed a high-throughput siRNA screen of 23-mer siRNAs that target all human or mouse genes. For each gene, at least four different siRNAs were used. In such a cell-based assay, the inventors seek to discover genes that can modulate the cytoplasm-to-nuclear translocation of NFAT-GFP and/or store-operated $Ca^{2+}$ entry into a cell. The siRNAs to such a gene result in either a decrease or an increase in the nuclear GFP fluorescence after TG treatment. The decrease or increase is at least two fold of the standard deviation for the control population of cells treated with TG but conducted in the absence of any siRNA, i.e. at least an average Z score of -2.0 or +2.0. The number of standard deviations from the mean is called the Z-score and can be found by the formula:

$$z = \frac{x - \mu}{\sigma}$$

where x is the mean number of cells having NFAT-GFP localization for the population of cells treated with siRNA, $\mu$ is mean number of cells having NFAT-GFP localization for the control population, and $\sigma$ is the standard deviation for the control population of cells. The control population of cells is assayed in parallel with the siRNAs.

From this screen, the inventors uncovered ~500 genes that strongly modulate NFAT and/or store-operated $Ca^{2+}$ entry into a cell, having an average Z-score of $\geq |4|$ and ~650 genes that moderately/weakly at modulate NFAT and/or store-operated $Ca^{2+}$ entry into a cell, having an average z-score of $-4<Z<-2$ or $2<Z<4$. The designation $|4|$ refers to the mathematical symbol for four absolute.

The screen identified known modulator of NFAT: calcineurin (CanB1 and CanA$\alpha$) which are involved in the dephosphorylating NFAT which is necessary for nuclear translocation; known store-operated $Ca^{2+}$ entry sensor proteins: Stim1 and Orai1; and KCNN4 (IKCa1, potassium intermediate/small conductance calcium-activated channel, subfamily N, member 4). Calcineurin (CN) is a protein phosphatase also known as protein phosphatase 2B (PP2B). Protein phosphatase 3 (formerly 2B), catalytic subunit, alpha isoform, also known as PPP3CA. The identification of known modulators of NFAT activity or store-operated $Ca^{2+}$ entry validates the accuracy and utility of the cell-based assay used by the inventors.

In addition to calcineurin, the siRNA screen identified KCNN4 (IKCa1, potassium intermediate/small conductance calcium-activated channel, subfamily N, member 4) that is known to be indirectly involved in NFAT nuclear localization via SOCE. Several reports have demonstrated that Kv1.3 and IKCa1 $K^+$ channels play crucial roles in T-cell activation, inflammation, progression of autoimmune diseases, and of other immunological disorders (Cahalan et al., 2001, Clin Immunol 21:235-252; Wulff et al., 2003, Curr. Opin. Drug Discov. Devel. 6:640-647; Chandy et al., 2004, Trends Pharmacolog Sci 25:280-289; Vicente et al., 2004, FEBS Lett 572:189-194). The use of Kv1.3 and IKCa1 K+ channel-blockers have been shown to ameliorate several types of disorders.

The high-throughput siRNA screen also identified several nuclear transport proteins: RAN (ras-related nuclear protein), RANBP2 (RAN binding protein 2), KPNB1 (karyopherin (importin) beta 1), CSE1L (chromosome segregation 1-like), and CRM1 (exportin 1, XPO1).

The entry and exit of large molecules from the cell nucleus is tightly controlled by the nuclear pore complexes (NPCs). Although small molecules can enter the nucleus without regulation, macromolecules such as RNA and proteins require association with karyopherins called importins to enter the nucleus and exportins to exit. The ability of both importins (KPNB1 and CSE1L) and exportins (CRM1) to transport their cargo is regulated by the small Ras related GTPase, RAN.

In some embodiments, the identified genes are SEQ. ID NOS:1-11 (Genbank Accession No. NM_000944; NM_021132.1; NM_006325; NM_006267.4; NM_002265.4, NM_001316; NM_003400.3; NM_003156.2, NM_020860.2, NM_032790.3, NM_002250.2).

Other examples of modulate genes identified in the cell-base assay as described herein include those that are involved in (1) Golgi-to-plasma membrane trafficking, (2) associated with mitochondria, (3) scaffold proteins (with PDZ domains, etc), (4) ubiquitin metabolism, (5) noncoding RNAs (possibility containing microRNAs), (6) RNA-binding proteins, and (7) potassium channels: KCNN4 (see Table 1, 2 or 3).

Accordingly, the invention provides a method of modulating NFAT activity, the method comprising administering a therapeutically effective amount of a pharmaceutical composition comprising an agent that inhibits the activity a protein and/or the expression of a gene identified in Table 1, 2 or 3.

In one embodiment, provided herein is a method modulating store-operated $Ca^{2+}$ entry into a cell, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3.

In one embodiment, provided herein is a method of treating and/or preventing hyperactivity or inappropriate immune responses in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2). In some embodiment, the subject can be one who is at risk of developing hyperactivity or inappropriate immune response, for example, an organ transplant recipient.

In some aspects, the hyperactivity or inappropriate immune response in a subject is associated with acute and chronic immune diseases, e.g., allergic and atopic diseases, e.g., asthma, allergic rhinitis, allergic conjunctivitis and atopic dermatitis, and to autoimmune diseases, e.g., rheumatoid arthritis, insulin-dependent diabetes, inflammatory bowel disease, autoimmune thyroiditis, hemolytic anemia and multiple sclerosis. Hyperactivity or inappropriate activity of the immune system is also involved in transplant graft rejections and graft-versus-host disease. Administering an agent that inhibits a gene identified in Table 1, 2 or 3 can down-regulate NFAT activity and/or store-operated $Ca^{2+}$ entry and thereby reduce chronic T cell activation.

In some embodiments, the genes identified in Table 1, 2 or 3 involved in down-regulate NFAT activity and/or store-operated $Ca^{2+}$ entry. Agents that inhibit such genes can enhance NFAT activity and/or store-operated $Ca^{2+}$ entry and thereby increase immune response. Accordingly, provided herein is method of increasing immune response in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3.

Subjects having immunodeficiency disorders can benefit from the method described herein of increasing immune response. Immunodeficiency disorders can include or result from but not limited to common variable immunodeficiency, selective antibody deficiency (such as IgA deficiency), transient hypogammaglobulinemia of infancy, X-linked agammaglobulinemia, chronic mucocutaneous candidiasis, DiGeorge anomaly, ataxia-telangiectasia, severe combined immunodeficiency disease, Wiskott-Aldrich syndrome, X-linked lymphoproliferative syndrome, Chédiak-Higashi syndrome, chronic granulomatous disease, hyperimmunoglobulinemia E syndrome, leukocyte adhesion defects, leukocyte glucose-6-phosphate dehydrogenase deficiency, myeloperoxidase deficiency, complement component 1 (C1) inhibitor deficiency (hereditary angioedema), C3 deficiency, C6 deficiency, C7 deficiency, C8 deficiency, chemotherapy and radiation therapy, human immunodeficiency virus (HIV) infection, cancer, blood disorders (such as aplastic anemia, leukemia, and myelofibrosis), kidney failure, diabetes, liver disorders, and spleen disorders.

In some aspects, the subject is a mammal, for example, a human, mouse, rat, guinea pig, dog, cat, horse, cow, pig, monkey, chimpanzee, baboon, or rhesus. The methods provided herein are applicable to any subject that comprises an immune system which comprises NFAT transcription activation factors and the need for sustained $Ca^{2+}$ influx for NFAT activation.

In one embodiment, provided herein is a method of treating a cell proliferation disease or disorder in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2). In some embodiment, the subject can be one who is at risk of developing a cell proliferation disease or disorder.

As used herein, cell proliferation disease or disorder is a neoplastic cell proliferation disorder, such as a therapy resistant cancer, a metastasis or malignant cancer. In one embodiment, the methods described herein are applied to subject who has or is at risk of having a metastasis or malignant cancer. The metastasis or malignant cancer can also be a recurring or relapsed cancer, after the subject has been treated with conventional cancer therapy such as radiation and/or chemotherapy. Accordingly, the neoplastic cell proliferation disorder is a therapy resistant cancer. Other cancers include but are not limited to solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, askocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Kaposi's sarcoma.

Cancers include, but are not limited to, bladder cancer, breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

Cardiovascular disease is the major cause of death in industrialized nations. Targeted intervention in calcineurin, a calmodulin-dependent, calcium-activated phosphatase and its substrate, nuclear factor of activated T cells (NFAT), was demonstrated to be effective in the treatment of cardiovascular diseases. In one embodiment, provided herein is a method of treating a cardiovascular disorder in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2). In some embodiment, the subject can be one who is at risk of developing a cardiovascular disorder. Cardiovascular disorders including cardiac hypertrophy, restenosis, atherosclerosis, and angiogenesis.

Since there is a potential role for NFAT in axon re-growth and regeneration following axonal injury, modulating NFAT activity after such injury can promote axonal re-growth and regeneration. Accordingly, in one embodiment, provided herein is a method of treating an injury to the nervous system in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2).

Excessive osteoclast formation is characteristic of a variety of bone diseases such as rheumatoid arthritis. Hence a strategy for suppressing the excessive osteoclast formation can be novel therapeutic approach for the treatment of bone disease. Accordingly, in one embodiment, provided herein is a method of treating a bone disease in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2). The method comprises suppressing the excessive osteoclast formation and activity.

In one embodiment, provided herein is a method of treating diabetes in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2). In some embodiment, the subject can be one who is at risk of developing diabetes.

In one embodiment, provided herein is a method of treating an angiogenic disease or disorder in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2). In some embodiment, the subject can be one who is at risk of developing an angiogenesis. In some embodiments, the angiogenic disease or disorder is related to VEGF-induced and IL-1 induced gene expression.

In one embodiment, provided herein is a method of promoting or inhibiting T cell anergy in a subject in need thereof, the method comprising administering a therapeutically effective amount of a pharmaceutical composition comprising an agent that inhibits the activity a protein expressed from a gene identified in Table 1, 2 or 3 and/or the expression of a gene identified in Table 1, 2 or 3, wherein the gene is not calcineurin, calmodulin, Stim1, Stim2, Orai1 or dual-specificity tyrosine-(Y)-phosphorylation regulated kinase 2 (DYRK2).

In one embodiment, the agent that inhibits the activity of a protein expressed from a gene identified in Table 1, 2 or 3 and/or the expression of the gene identified in Table 1, 2 or 3 can be administered to the subject together with additional therapeutic agents, cancer therapy, immunosuppressant therapy, immunodeficiency therapy, steroid therapy, and psychotherapy.

In one embodiment, the agent that inhibits the activity of a protein expressed from a gene identified in Table 1, 2 or 3 and/or the expression of the gene identified in Table 1, 2 or 3 is a small molecule, nucleic acid, nucleic acid analogue, protein, antibody, peptide, aptamer or variants or fragments thereof. Such an agent can take the form of any entity which is normally not present or not present at the levels being administered to the cell or organism.

Other forms of inhibitors include a nucleic acid agent which is an RNAi agent such as a siRNA, shRNA, miRNA, dsRNA or ribozyme or variants thereof.

Calcineurin/NFAT Axis in Vertebrates

Calcineurin is a calmodulin-dependent, calcium-activated protein phosphatase composed of catalytic and regulatory subunits. The serine/threonine-specific phosphatase functions within signal transduction pathways that regulate gene expression and biological responses in many developmentally important cell types. Calcineurin signaling was first defined in T lymphocytes as a regulator of nuclear factor of activated T cells (NFAT) transcription factor nuclear translocation and activation.

The NFAT transcription factor family consists of five members NFAT1, NFAT2, NFAT3, NFAT4 and NFAT5. NFAT1-4 are regulated by calcium signaling. All family members contain the rel DNA binding domain, however only NFAT1-4 contains the $Ca^{2+}$ sensor/translocation domain. The activation process of the NFAT transcription factor family is tightly regulated by calcium-dependent phosphatase calcineurin. NFAT activation is dependent upon a rise in intracellular $Ca^{2+}$, which activates the serine/threonine phosphatase, calcineurin. The increase in intracellular calcium levels can occur, e.g., by means of store-operated calcium entry (SOCE). Activated calcineurin rapidly dephosphorylates the serine rich region (SRR) and SP-repeats in the amino termini of NFAT proteins resulting in a conformational change that exposes a nuclear localization signal resulting in NFAT nuclear import.

Opposing this, the nuclear export of NFAT requires the sequential re-phosphorylation of this domain by several kinases including GSK-3β. Other post-translational modifications such as acetylation and sumoylation, as well as phosphorylation events distinct from those in the $Ca^{2+}$/translocation domain, also modulate NFAT transcriptional activity.

As the sole $Ca^{2+}$ entry mechanism in a variety of non-excitable cells, store-operated calcium (SOC) influx is important in Ca$^{2+}$ signaling and many other cellular processes, in particular, for the calcium-release-activated calcium (CRAC) channels in T lymphocytes. The CRAC channels are essential to the immune response, sustained activity of CRAC channels being required for gene expression and proliferation of the activated T cell. STIM1 and Orai 1 function as Ca$^{2+}$ sensors of changes in the intracellular Ca$^{2+}$ stores to activate CRAC channels.

NFAT functions as an integrator of multiple signaling pathways and achieves this through a combinatorial mechanism of transcriptional regulation. Other cellular signaling pathways including MAP kinase, WNT or NOTCH. NFAT, along with other transcription factors and co-activators, integrates signaling pathways by binding to chromatin in a highly specific and concerted fashion only upon receiving the appropriate signaling cues. The composition of the NFAT transcription complexes assembled at the promoter and enhancer elements of target genes is thus dependent upon both signaling and chromatin context, which determines when and where NFAT complexes activate or repress transcription. The NFAT family of transcription factors functions in combination with other transcription factors and co-activators to regulate genes central for many developmental systems. NFAT proteins have been found to be involved in numerous cellular processes, for example, cell cycle regulation, cell differentiation, cell survival, angiogenesis, tumor cell invasion and metastasis, myogenesis, chondrocyte differentiation and the development of the cardiovascular system, the complex nervous system, the recombinational immune system, and the cardiovascular system in a vertebrate (Graef I A et. al., Curr Opin Genet Dev. 2001, 11:505-12; Macian F., Nat Rev Immunol. 2005; 5:472-84; Schulz and Yutzey, Dev Biol. 2004, 266:1-16; Crabtree and Olson, Cell. 2002; 109(Suppl):S67-79).

The development, activation, and maintenance of the immune system is dependent on several factors, of which Ca$^{2+}$ influx and the activation of transcription factors are two of the most important factors. NFAT proteins are expressed in immune cells and play a key role in eliciting immune responses. Ca$^{2+}$/calcineurin/NFAT signaling pathway is essential for lymphocyte activation, for short-term as well as long-term responses by immune-system cells, which include T and B cell proliferation and differentiation.

The activated NFAT proteins, in turn, induce transcription of cytokine genes which are required for an immune response. For example, NFAT1 and NFAT2 are much higher in memory and effector T cells than in naïve T cells, suggesting that they play an important function in memory T cells activation by way of IL-2 cytokine production in the memory T cells.

Calcineurin is indirectly responsible for activating the transcription of interleukin 2 (IL-2), that stimulates the growth and differentiation of T cell response. When an antigen presenting cell interacts with a T cell receptor on T cells, there is an increase in the cytoplasmic level of calcium, (Yamashita M., et. al., J Exp Med. 2000, 191: 1869-1880) which activates calcineurin, by binding a regulatory subunit and activating calmodulin binding. Calcineurin induces different transcription factors such as NFATs that are important in the transcription of IL-2 genes. Calcineurin dephosphorylates the cytoplasmic component of NFATs, transcription factors that can then go into the nucleus and turn on genes involved in IL-2 synthesis. IL-2 activates T-helper lymphocytes and induces the production of other cytokines. In this way, it governs the action of cytotoxic lymphocytes and NK cells. The amount of IL-2 being produced by the T-helper cells is believed to influence the extent of the immune response significantly. In immunosuppressive therapy, calcineurin is inhibited by cyclosporin, pimecrolimus (Elidel) and tacrolimus (FK506)—these drugs are known as calcineurin inhibitors.

Interleukin-21 (IL-21), a potent immunomodulatory four-alpha-helical-bundle type I cytokine, is produced by NKT and CD4(+) T cells and has pleiotropic effects on both innate and adaptive immune responses. These actions include positive effects such as enhanced proliferation of lymphoid cells, increased cytotoxicity of CD8(+) T cells and natural killer (NK) cells, and differentiation of B cells into plasma cells. Conversely, IL-21 also has direct inhibitory effects on the antigen-presenting function of dendritic cells and can be proapoptotic for B cells and NK cells. IL-21 is also produced by Th17 cells and is a critical regulator of Th17 development. The regulatory activity of IL-21 is modulated by the differentiation state of its target cells as well as by other cytokines or costimulatory molecules. IL-21 has potent antitumor activity but is also associated with the development of autoimmune disease. IL-21 transcription is dependent on a calcium signal and NFAT sites, and IL-21 requires Stat3 for its signaling. The key to harnessing the power of IL-21 will depend on better understanding its range of biological actions, its mechanism of action, and the molecular basis of regulation of expression of IL-21 and its receptor (Spolski and Leonard, Annu Rev Immunol. 2008, 26:57-79).

NFAT has also been shown to the crucial sensor of T cell receptor signaling in the interleukin (IL)-17 promoter and expression. IL-17 is a pro-inflammatory cytokine produced by T helper type 17 (Th17) cells, which have critical role in immunity to extracellular bacteria and the pathogenesis of several autoimmune disorders and asthma. There are two NFAT binding sites in the minimal promoter of IL-17. (Liu et. al., J Biol. Chem. 2004, 279:52762-71, Sundrud and Rao, Curr Opin Immunol. 2007 June; 19(3):287-93).

Central tolerance in the thymus is the primary mechanism for deleting autoreactive T cells. Despite this, escape of self-reactive T lymphocytes into the periphery reveals the threat of autoimmunity. To compensate for its imperfection, the thymus also produces a naturally occurring subset of Foxp3+ CD4+ CD25+ regulatory T cells with suppressive function, capable of controlling autoreactive cells. Foxp3 (forkhead box P3), the lineage-specific marker for this subset of cells, is crucial to their thymic development and peripheral function. NFAT, in cooperation with Foxp 3, are crucial for the phenotype, development, maintenance, and function of these regulatory T cells, and the ultimately for maintaining immunological tolerance in an organism (Wu et. al, Cell. 2006, 126: 375-87; Rudensky A Y, et. al., Cell. 2006, 126:253-6; Mays and Chen, Cell Res. 2007, 17:904-18; Oh-Hora M, et. al., 2008, Nat. Immunol. 2008, 9:432-43).

Inhibitory modulation of NFAT function can be a strategy for immunosuppressive therapy, a bottleneck of T cell receptor-dependent activation of T cells and for promoting T-cell anergy.

Recently report show that NFAT is involved in axonal growth and guidance during vertebrate development (Nguyen and Di Giovanni, Int J Dev Neurosci. 2008, 26: 141-145). The extension and organization of sensory axon projection and commissural axon growth are both dependent upon NFAT activity. Triple NFAT2/3/4 mutant mice demonstrate that the extension and organization of sensory axon projection and commissural axon growth are both dependent upon NFAT activity. Neurotrophin and L-type calcium channel signaling modulate intracellular calcium levels to regulate the nuclear import and transcriptional activity of NFAT by activating the phosphatase calcineurin. The rephosphorylation and subsequent export of NFAT from the nucleus is mediated by several kinases, including GSK-3 beta, which contribute to the fine tuning of NFAT transcriptional activity in neurons. Thus there is a potential role for NFAT in axon re-growth and regeneration following axonal injury.

The calcium/calcineurin/NFAT signaling is also involved in cardiovascular and skeletal muscle development in vertebrates. Inhibition, mutation, or forced expression of calcineurin pathway genes result in defects or alterations in cardiomyocyte maturation, heart valve formation, vascular development, skeletal muscle differentiation and fiber-type switching, and cardiac and skeletal muscle hypertrophy (Schulz and Yutzey, Dev Biol. 2004, 266:1-16). Inhibition of calcineurin-NFAT is a negative regulator of cardiac myocyte (CM) hypertrophy (Fiedler et. al., Proc Natl Acad Sci USA. 2002, 99:11363-8). Since cardiovascular disease is the major cause of death in industrialized nations. Targeted intervention in calcineurin, a calmodulin-dependent, calcium-activated phosphatase and its substrate, nuclear factor of activated T cells (NFAT), can be effective in the treatment of cardiovascular diseases. Calcineurin/NFAT signaling pathway inhibition can be a therapeutic strategy in cardiovascular disorders including cardiac hypertrophy, restenosis, atherosclerosis, and angiogenesis.

Osteoclasts are multinucleated cells of monocyte/macrophage origin that degrade bone matrix. The differentiation of osteoclasts is dependent on a tumor necrosis factor (TNF) family cytokine, receptor activator of nuclear factor (NF)-kappaB ligand (RANKL), as well as macrophage colony-stimulating factor (M-CSF). Congenital lack of osteoclasts causes osteopetrosis. Among the essential molecules for osteoclastogenesis, including TNF receptor-associated factor (TRAF) 6, NF-kappaB, c-Fos and NFAT2. NFAT2 is activated by calcium signaling and binds to its own promoter, thus switching on an autoregulatory loop. C-Fos, as an activator protein (AP)-1 complex, is required for the autoamplification of NFAT2, enabling the robust induction of NFAT2. NFAT2 cooperates with other transcriptional partners to activate osteoclast-specific genes. Thus, NFAT2, the master transcription factor for osteoclast differentiation (Takayanagi, Ann. N.Y. Acad. Sci. 2007, 1116: 227-237). Excessive osteoclast formation characteristic of a variety of bone diseases. In rheumatoid arthritis, bone destruction is caused by the enhanced activity of osteoclasts. Suppressing the excessive osteoclast formation and/or the enhanced activity of osteoclasts by way of modulating the calcineurin/NFAT axis can be a strategy for the treatment and/or prevention of a variety of bone diseases.

Calcineurin/NFAT signaling axis is also important in the renal regulation of water homeostasis. A new member of the nuclear factor of activated T cells (NFAT) family has recently been discovered, NFAT 5, or Ton EBP. Ton EBP is the only known mammalian transcription factor that regulates gene expression in response to hypertonicity (Tyagi and Nandhakumar, Indian J Exp Biol. 2008, 46:89-93).

Deregulation of calcineurin/NFAT signaling and/or abnormal expression of its components have recently been reported in solid tumors of epithelial origin, lymphoma and lymphoid leukemia. Mouse models of human T-ALL/lymphoma shows that persistent activation of calcineurin/NFAT signaling is pro-oncogenic in vivo (Medyouf and Ghysdael, Cell Cycle. 2008, 7:297-303). Experimental evidence indicate the critical role of NFAT3 in some carcinogen-induced cell transformation and tumorigenicity (Lu and Huan, Curr Cancer Drug Targets. 2007, 7:343-53). There is an emerging role for $Ca^{2+}$/calcineurin/NFAT signaling in cancerogenesis (Buchholz and Ellenrieder, Cell Cycle. 2007, 6(1):16-9). Modulation of NFAT can be suitable for the treatment of neoplastic cell proliferation diseases such as cancers.

Deregulation of calcineurin/NFAT signaling is also reported to be associated with defects in vertebrate development, since NFAT family of transcription factors are major regulators of vertebrate development. In human trisomy 21 or Down's syndrome, there is an human chromosome 21. Anon J R, et. al. (Nature. 2006, 441:595-600) and Gwack Y, et. al., (Nature, 2006, 441:646-50) report of two genes, DSCR1 and DYRK1A, that lie within the critical region of human chromosome 21 and the gene products act synergistically to inhibit the activation of NFATc transcription factors. The increase in expression of DSCR1 and DYRK1A can lead to a decrease in NFAT activation. In the mouse models of Down's syndrome, which are actually Dscr1- and Dyrk1a-overexpressing mice, these mice are found to be calcineurin- and NFAT-deficient. The reduced amount of NFAT can be associated with many of the features of Down's syndrome and also in many human diseases such as autoimmune disease and cancer as described herein.

Pancreatic beta-cells in the islet of Langerhans produce the hormone insulin, which maintains blood glucose homeostasis. Perturbations in beta-cell function may lead to impairment of insulin production and secretion and the onset of diabetes mellitus. Several essential beta-cell factors have been identified that are required for normal beta-cell function, including six genes that when mutated give rise to inherited forms of diabetes known as Maturity Onset Diabetes of the Young (MODY) (Heit, Bioessays. 2007, 29(10):1011-21). mice with a beta-cell-specific deletion of the calcineurin phosphatase regulatory subunit, calcineurin b1 (Cnb1), develop age-dependent diabetes characterized by decreased beta-cell proliferation and mass, reduced pancreatic insulin content and hypoinsulinaemia. Moreover, beta-cells lacking Cnb1 have a reduced expression of established regulators of beta-cell proliferation. Conditional expression of active NFAT1 in Cnb1-deficient beta-cells rescues these defects and prevents diabetes. In normal adult beta-cells, conditional NFAT activation promotes the expression of cell-cycle regulators and increases beta-cell proliferation and mass, resulting in hyperinsulinaemia. Calcineurin/NFAT signaling regulates pancreatic beta-cell growth and function. Conditional NFAT activation also induces the expression of genes critical for beta-cell endocrine function, including all six genes mutated in hereditary forms of monogenic type 2 diabetes (Heit, Nature. 2006, 443(7109):345-9). Modulation of NFAT provides novel therapeutic approaches for the treatment of diabetes and for the prevention of diabetes for those at risk of developing diabetes.

There are evidences that the activation of calcineurin and NFAT and subsequently the PKC and the MEK/ERK MAPK pathways are induced by VEGF-A and IL-1 in endothelial cells. Gene activation via PLC-gamma provides VEGF with the potency to induce a wide spectrum of genes including many also upregulated by IL-1 (Schweighofer, Clin Hemorheol Microcirc. 2007, 37:57-62). Modulate calcineurin/NFAT can reduce VEGF-induced gene expression and reduced sprouting in undesired angiogenesis, such as in cancer, age-related macular degeneration, diabetic retinopathy; rheumatoid arthritis; Alzheimer's disease; obesity and endometriosis.

Nucleic Acid Inhibitors

In some embodiments, agents that inhibit the expression of a Dicer are nucleic acids. Nucleic acid inhibitors of a Dicer gene include, but not are limited to, RNA interference-inducing molecules (RNAi), for example, but not limited to, siRNA, dsRNA, stRNA, shRNA, an anti-sense oligonucleotide and modified versions thereof, where the RNA interference molecule silences the gene expression of the Dicer gene. In some embodiments, the nucleic acid inhibitor of a Dicer gene is an anti-sense oligonucleic acid, or a nucleic acid analogue, for example, but not limited to DNA, RNA, peptide-nucleic acid (PNA), pseudo-complementary PNA (pcPNA), or locked nucleic acid (LNA) and the like. In alternative embodiments, the nucleic acid is DNA or RNA, or nucleic acid analogues, for example, PNA, pcPNA and LNA. A nucleic acid can be single or double stranded, and can be selected from a group comprising nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc. Additional sequences can also be present.

RNA interference (RNAi) is a phenomenon in which double-stranded RNA (dsRNA) specifically suppresses the expression of a gene with its complementary sequence. Small interfering dsRNAs (siRNA) mediate post-transcriptional gene-silencing, and can be used to induce RNAi in mammalian cells. The dsRNA is processed intracellularly to release a short single stranded nucleic acid that can complementary base pair with the gene's primary transcript or mRNA. The resultant a double stranded RNA is susceptible to RNA degradation. Protein translation is thus prevent.

In some embodiments, single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme.

Protein expression from the genes identified in Table 1, 2 or 3 can be reduced by inhibition of the expression of polypeptide (e.g., transcription, translation, post-translational processing) or by "gene silencing" methods commonly known by persons of ordinary skill in the art.

RNA interference (RNAi) provides a powerful approach for inhibiting the expression of selected target polypeptides. RNAi uses small interfering RNA (siRNA) duplexes that target the messenger RNA encoding the target polypeptide for selective degradation. siRNA-dependent post-transcriptional silencing of gene expression involves cutting the target messenger RNA molecule at a site guided by the siRNA.

RNA interference (RNAi) is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76:9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease can be of at least 5%, 10%, 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

Double-stranded RNA (dsRNA) has been shown to trigger one of these posttranscriptional surveillance processes, in which gene silencing involves the degradation of single-stranded RNA (ssRNA) targets complementary to the dsRNA trigger (Fire A, 1999, Trends Genet. 15:358-363). RNA interference (RNAi) effects triggered by dsRNA have been demonstrated in a number of organisms including plants, protozoa, nematodes, and insects (Cogoni C. and Macino G, 2000, Curr Opin Genet Dev 10:638-643).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April, 9(4):493-501, incorporated by reference herein in its entirety).

The target gene or sequence of the RNA interfering agent can be a cellular gene or genomic sequence, e.g. that of calcineurin, Ran-GTPase, or Stim1 sequence. An siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196). Other examples include RNA molecules containing the O-linkage between the sugar and the heterocyclic base of the nucleoside, which confers nuclease resistance and tight complementary strand binding to the oligonucleotides molecules similar to the oligonucleotides containing 2'-O-methyl ribose, arabinose and particularly D-arabinose (U.S. Pat. No. 5,177,196).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

The more preferred siRNA modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

Locked nucleic acids (LNAs), also known as bridged nucleic acids (BNAs), developed by Wengel and co-workers (Koshkin A. A., 1998, Tetrahedron, 54:3607-3630) and Imanishi and co-workers (Obika S., 1998, Tetrahedron Lett., 39:5401-5404). LNA bases are ribonucleotide analogs containing a methylene linkage between the 2' oxygen and the 4' carbon of the ribose ring. The constraint on the sugar moiety results in a locked 3'-endo conformation that preorganizes the base for hybridization and increases melting temperature (Tm) values as much as 10° C. per base (Wengel J., 1999, Acc. Chem. Res., 32:301-310; Braasch D. A. and Corey, D. R., 2001, Chem. Biol., 8:1-7). LNA bases can be incorporated into oligonucleotides using standard protocols for DNA synthesis. This commonality facilitates the rapid synthesis of chimeric oligonucleotides that contain both DNA and LNA bases and allows chimeric oligomers to be tailored for their binding affinity and ability to activate RNase H. Because oligomers that contain LNA bases have a native phosphate backbone they are readily soluble in water. Introduction of LNA bases also confers resistance to nucleases when incorporated at the 5' and 3' ends of oligomers (Crinelli R., et. al., 2002, Nucleic Acids Res., 30:2435-2443). The ability to use LNAs for in vivo applications is also favored by the finding that LNAs have demonstrated low toxicity when delivered intravenously to animals (Wahlestedt C., et. al., 2000, Proc. Natl. Acad. Sci. USA, 97: 5633-5638).

LNAs and LNA-DNA chimeras have been shown to be potent inhibitors of human telomerase and that a relatively short eight base LNA is a 1000-fold more potent agent than an analogous peptide nucleic acid (PNA) oligomer (Elayadi A. N., et. al., 2002, Biochemistry, 41: 9973-9981). LNAs and LNA-DNA chimeras have also been shown to be useful agents for antisense gene inhibition. Wengel and co-workers have used LNAs to inhibit gene expression in mice (Wahlestedt C., et. al., 2000, Proc. Natl. Acad. Sci. USA, 97:5633-5638), while Erdmann and colleagues have described the design of LNA-containing oligomers that recruit RNase H and have described the rules governing RNase H activation by LNA-DNA chimeras in cell-free systems (Kurreck J., et. al., 2002, Nucleic Acids Res., 30:1911-1918).

The syntheses of LNA-containing oligomers are known in the art, for examples, those described in U.S. Pat. Nos. 6,316, 198, 6,670,461, 6,794,499, 6,977,295, 6,998,484, 7,053,195, and U.S. Patent Publication No. US 2004/0014959, and all of which are hereby incorporated by reference in their entirety.

Another nucleic acid derivative envisioned in the methods described herein is phosphorodiamidate morpholino oligomer (PMO). PMOs are DNA mimics that inhibit expression of specific mRNA in eukaryotic cells (Arora, V., et. al., 2000, J. Pharmacol. Exp. Ther. 292:921-928; Qin, G., et. al., 2000, Antisense Nucleic Acid Drug Dev. 10:11-16; Summerton, J., et. al., 1997, Antisense Nucleic Acid Drug Dev. 7:63-70). They are synthesized by using the four natural bases, with a base sequence that is complementary (antisense) to a region of a specific mRNA. They are different than DNA in the chemical structure that links the bases together. Ribose has been replaced with a morpholine group, and the phosphodiester is replaced with a phosphorodiamidate. These alterations make the antisense molecule resistant to nucleases (Hudziak, R., et. al., 1996 Antisense Nucleic Acid Drug Dev. 6:267-272) and free of charges at physiological pH, yet it retains the molecular architecture required for binding specifically to a complementary strand of nucleic acid (Stein, D., et. al, 1997, Antisense Nucleic Acid Drug Dev. 7:151-157; Summerton, J., et. al., 1997, Antisense Nucleic Acid Drug Dev. 7:63-70; Summerton, J., and D. Weller., 1997, Antisense Nucleic Acid Drug Dev. 7:187-195).

The synthesis, structures, and binding characteristics of morpholine oligomers are detailed in U.S. Pat. Nos. 5,698, 685, 5,127,866, 5,142,047, 5,166,315, 5,521,063, and 5,506, 337, and all of which are hereby hereby incorporated by reference in their entirety. PMOs can be synthesized at AVI BioPharma (Corvallis, Oreg.) in accordance with known methods, as described, for example, in Summerton, J., and D. Weller U.S. Pat. No. 5,185,444; and Summerton, J., and D. Weller. 1997, Antisense Nucleic Acid Drug Dev. 7:187-195.

For example, PMO against calcineurin or KCNN4 transcripts should containing between 12-40 nucleotide bases, and having a targeting sequence of at least 12 subunits complementary to the respective transcript. Methods of making and using PMO for the inhibition of gene expression in vivo are described in U.S. Patent Publication No. US 2003/0171335; US 2003/0224055; US 2005/0261249; US 2006/0148747; S 2007/0274957; US 2007/003776; and US 2007/0129323; and these are hereby incorporated by reference in their entirety.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Other siRNAs useful for targeting the genes identified in Table 1, 2 or 3 can be readily designed and tested. Accordingly, siRNAs useful for the methods described herein include siRNA molecules of about 15 to about 40 or about 15 to about 28 nucleotides in length, which are homologous to an gene identified in Table 1, 2 or 3. Preferably, the siRNA molecules targeting the gene identified in Table 1, 2 or 3 have a length of about 19 to about 25 nucleotides. More preferably, the siRNA molecules have a length of about 19, 20, 21, or 22 nucleotides. The siRNA molecules can also comprise a 3' hydroxyl group. The siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of the RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment, the RNA molecule that targets the gene identified in Table 1, 2 or 3 is double stranded—one strand has a 3' overhang and the other strand can be blunt-ended or have an overhang. In the embodiment in which the gene identified in Table 1, 2 or 3 targeting RNA molecule is double stranded and both strands comprise an overhang, the length of the overhangs can be the same or different for each strand. In a embodiment, the RNA comprises at least 6, 7, 8, 9, 10, 11, 12, 13, 14, 15, 16, 17, 18, 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

In some embodiments, assessment of the expression and/or knock down of gene identified in Table 1, 2 or 3 using gene specific siRNAs can be determined by methods that are well known in the art, such as western blot analysis or enzyme activity assays. Other methods can be readily prepared by those of skill in the art based on the known sequence of the target mRNA.

siRNA sequences are chosen to maximize the uptake of the antisense (guide) strand of the siRNA into RISC and thereby maximize the ability of RISC to target the mRNA of the gene identified in Table 1, 2 or 3 for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the mRNA of the human gene identified in Table 1, 2 or 3.

In a preferred embodiment, the siRNA or modified siRNA is delivered in a pharmaceutically acceptable carrier. Additional carrier agents, such as liposomes, can be added to the pharmaceutically acceptable carrier.

In another embodiment, the siRNA is delivered by delivering a vector encoding small hairpin RNA (shRNA) in a pharmaceutically acceptable carrier to the cells in an organ of an individual. The shRNA is converted by the cells after transcription into a siRNA capable of targeting a specific gene identified in Table 1, 2 or 3. In one embodiment, the vector can be a plasmid, a cosmid, a phagmid, a hybrid thereof, or a virus. In one embodiment, the vector can be a regulatable vector, such as tetracycline inducible vector.

In one embodiment, the RNA interfering agents used in the methods described herein are taken up actively by cells in vivo following intravenous injection, e.g., hydrodynamic injection, without the use of a vector, illustrating efficient in vivo delivery of the RNA interfering agents, e.g., the siRNAs used in the methods of the invention.

Other strategies for delivery of the RNA interfering agents, e.g., the siRNAs or shRNAs used in the methods of the invention, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

As noted, the dsRNA, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

RNA interference molecules and nucleic acid inhibitors useful in the methods as disclosed herein can be produced using any known techniques such as direct chemical synthesis, through processing of longer double stranded RNAs by exposure to recombinant Dicer protein or *Drosophila* embryo lysates, through an in vitro system derived from S2 cells, using phage RNA polymerase, RNA-dependant RNA polymerase, and DNA based vectors. Use of cell lysates or in vitro processing can further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.)

In some embodiments, an agent is protein or polypeptide or RNAi agent that inhibits the expression of genes identified in Table 1, 2 or 3 and/or activity of proteins encoded by gene identified in Table 1, 2 or 3. In such embodiments, cells can be modified (e.g., by homologous recombination) to provide increased expression of such an agent, for example, by replacing, in whole or in part, the naturally occurring promoter with all or part of a heterologous promoter so that the cells express the natural inhibitor agent. For example, a protein or miRNA inhibitor of a gene identified in Table 1, 2 or 3 become expressed at higher levels. The heterologous promoter is inserted in such a manner that it is operatively linked to the desired nucleic acid encoding the agent. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems. Cells also can be engineered to express an endogenous gene comprising the agent under the control of inducible regulatory elements, in which case the regulatory sequences of the endogenous gene can be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al. The agent can be prepared by culturing transformed host cells under culture conditions suitable to express the miRNA. The resulting expressed agent can then be purified from such culture (i.e., from culture medium or cell extracts) using known purification processes, such as gel filtration and ion exchange chromatography. The purification of a peptide or nucleic acid agent inhibitor of the gene identified in Table 1, 2 or 3 can also include an affinity column containing agents which will bind to the protein; one or more column steps over such affinity resins as concanavalin A-agarose, heparin-Toyopearl™ or Cibacrom blue 3GA Sepharose; one or more steps involving hydrophobic interaction chromatography using such resins as phenyl ether, butyl ether, or propyl ether; immunoaffinity chromatography, or complementary cDNA affinity chromatography.

In one embodiment, the nucleic acid inhibitors of the genes identified in Table 1, 2 or 3 can be obtained synthetically, for example, by chemically synthesizing a nucleic acid by any method of synthesis known to the skilled artisan. The synthesized nucleic acid inhibitors of the gene identified in Table 1, 2 or 3 can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In some circumstances, for example, where increased nuclease stability is desired, nucleic acids having nucleic acid analogs and/or modified internucleoside linkages can be preferred. Nucleic acids containing modified internucleoside linkages can also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($—CH_2—S—CH_2$), dimethylene-sulfoxide ($—CH_2—SO—CH_2$), dimethylene-sulfone ($—CH_2—SO_2—CH_2$), 2'-O-alkyl, and 2'-deoxy-2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein). U.S. Pat. No. 5,614,617 and U.S. Pat. No. 5,223,618 to Cook, et al., U.S. Pat. No. 5,714,606 to Acevedo, et al, U.S. Pat. No. 5,378,825 to Cook, et al., U.S. Pat. No. 5,672,697 and U.S. Pat. No. 5,466,786 to Buhr, et al., U.S. Pat. No. 5,777,092 to Cook, et al., U.S. Pat. No. 5,602,240 to De Mesmacker, et al., U.S. Pat. No. 5,610,289 to Cook, et al. and U.S. Pat. No. 5,858,988 to Wang, also describe nucleic acid analogs for enhanced nuclease stability and cellular uptake.

The siRNA molecules of the present invention can be generated by annealing two complementary single-stranded RNA molecules together (one of which matches a portion of the target mRNA) (Fire et al., U.S. Pat. No. 6,506,559) or through the use of a single hairpin RNA molecule that folds back on itself to produce the requisite double-stranded portion (Yu et al. (2002) Proc. Natl. Acad. Sci. USA 99:6047-52). The siRNA molecules can also be chemically synthesized (Elbashir et al. (2001) Nature 411:494-98)

Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but are not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi.

siRNA can also be produced by in vitro transcription using single-stranded DNA templates (Yu et al., supra). Alternatively, the siRNA molecules can be produced biologically, either transiently (Yu et al., supra; Sui et al. (2002) Proc. Natl.

Acad. Sci. USA 99:5515-20) or stably (Paddison et al. (2002) Proc. Natl. Acad. Sci. USA 99:1443-48), using an expression vector(s) containing the sense and antisense siRNA sequences. siRNA can be designed into short hairpin RNA (shRNA) for plasmid- or vector-based approaches for supplying siRNAs to cells to produce stable gene identified in Table 1, 2 or 3 silencing. Examples of vectors for shRNA are #AM5779: -pSilencer™ 4.1-CMV neo; #AM5777: -pSilencer™ 4.1-CMV hygro; #AM5775: -pSilencer™ 4.1-CMV puro; #AM7209: -pSilencer™ 2.0-U6; #AM7210: -pSilencer™ 3.0-H1; #AM5768: -pSilencer™ 3.1-H1 puro; #AM5762: -pSilencer™ 2.1-U6 puro; #AM5770: -pSilencer™ 3.1-H1 neo; #AM5764: -pSilencer™ 2.1-U6 neo; #AM5766: -pSilencer™ 3.1-H1 hygro; #AM5760: -pSilencer™ 2.1-U6 hygro; #AM7207: -pSilencer™ 1.0-U6 (circular) from Ambion®.

Recently, reduction of levels of target mRNA in primary human cells, in an efficient and sequence-specific manner, was demonstrated using adenoviral vectors that express hairpin RNAs, which are further processed into siRNAs (Arts et al. (2003) Genome Res. 13:2325-32). In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell. 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

The targeted region of the siRNA molecule of the present invention can be selected from a given target gene sequence, e.g., the coding sequence of a gene identified in Table 1, 2 or 3, beginning from about 25 to 50 nucleotides, from about 50 to 75 nucleotides, or from about 75 to 100 nucleotides downstream of the start codon. Nucleotide sequences can contain 5' or 3' UTRs and regions nearby the start codon. One method of designing a siRNA molecule of the present invention involves identifying the 23 nucleotide sequence motif AA(N19)TT (where N can be any nucleotide), and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search can be extended using the motif NA(N21), where N can be any nucleotide. In this situation, the 3' end of the sense siRNA can be converted to TT to allow for the generation of a symmetric duplex with respect to the sequence composition of the sense and antisense 3' overhangs. The antisense siRNA molecule can then be synthesized as the complement to nucleotide positions 1 to 21 of the 23 nucleotide sequence motif. The use of symmetric 3' TT overhangs can be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but are not limited to the NCBI, BLAST, Derwent and GenSeq as well as commercially available oligosynthesis software such as Oligoengine®, can also be used to select siRNA sequences against EST libraries to ensure that only one gene is targeted.

Methods of predicting and selecting antisense oligonucleotides and siRNA are known in the art and are also found at www.genscript.com/ssl-bin/app/rnai, www.ambion.com/techlib/misc/siRNAfinder.html, www.dharmacon.com/DesignCenter, www.oligoengine.com, http://sfold.wadsworth.org/sirna.pl, www.genscript.com/ssl-bin/app/rnai, http://jura.wi.mitedu/biodsiRNAext/home.php and described in U.S. Pat. No. 6,060,248.

In some aspects, antisense nucleic acid technology can be used to inhibit the expression of gene identified in Table 1, 2 or 3. It is possible to synthesize a strand of nucleic acid (DNA, RNA or a chemical analogue) that will bind to the messenger RNA (mRNA) produced by that gene and inactivate it, effectively turning that gene "off". This is because mRNA has to be single stranded for it to be translated. This synthesized nucleic acid is termed an "anti-sense" oligonucleotide because its base sequence is complementary to the gene's messenger RNA (mRNA), which is called the "sense" sequence (so that a sense segment of mRNA "5'-AAGGUC-3'" would be blocked by the anti-sense mRNA segment "3'-UUCCAG-5'").

Delivery of RNA Interfering Agents: Methods of delivering RNA interfering agents, e.g., an siRNA, or vectors containing an RNA interfering agent, to the target cells (e.g., cells of the brain or other desired target cells, for cells in the central and peripheral nervous systems), can include, for example (i) injection of a composition containing the RNA interfering agent, e.g., an siRNA, or (ii) directly contacting the cell, e.g., a cell of the brain, with a composition comprising an RNA interfering agent, e.g., an siRNA. In one embodiment, the RNA interfering agent can be targeted to the bone marrow where the lymphocytes expressing the genes identified in Table 1, 2 or 3 are made. In another embodiment, RNA interfering agents, e.g., an siRNA can be injected directly into any blood vessel, such as vein, artery, venule or arteriole, via, e.g., hydrodynamic injection or catheterization. In yet another embodiment, the RNA interfering agent can be injected or applied topically directly to the site of the skin ulcers.

Administration can be by a single injection or by two or more injections. The RNA interfering agent is delivered in a pharmaceutically acceptable carrier. One or more RNA interfering agents can be used simultaneously. The RNA interfering agents, e.g., the siRNAs targeting the mRNA of genes identified in Table 1, 2 or 3, can be delivered singly, or in combination with other RNA interfering agents, e.g., siRNAs, such as, for example siRNAs directed to other cellular genes. siRNAs targeting gene identified in Table 1, 2 or 3 can also be administered in combination with other pharmaceutical agents which are used to treat or prevent immunological diseases or disorders.

In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with an siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein.

A viral-mediated delivery mechanism can also be employed to deliver siRNAs to cells in vitro and in vivo as described in Xia, H. et al. (2002) Nat Biotechnol 20(10): 1006). Plasmid- or viral-mediated delivery mechanisms of shRNA can also be employed to deliver shRNAs to cells in vitro and in vivo as described in Rubinson, D. A., et al. ((2003) Nat. Genet. 33:401-406) and Stewart, S. A., et al. ((2003) RNA 9:493-501).

RNA interfering agents, for e.g., an siRNA, can also be introduced into cells via the vascular or extravascular circulation, the blood or lymph system, and the cerebrospinal fluid.

The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

It is also known that RNAi molecules do not have to match perfectly to their target sequence. Preferably, however, the 5' and middle part of the antisense (guide) strand of the siRNA is perfectly complementary to the target nucleic acid sequence.

Accordingly, the RNAi molecules functioning as nucleic acid inhibitors of the genes identified in Table 1, 2 or 3 disclosed herein are, for example, but not limited to, unmodified and modified double stranded (ds) RNA molecules including short-temporal RNA (stRNA), small interfering RNA (siRNA), short-hairpin RNA (shRNA), microRNA (miRNA), double-stranded RNA (dsRNA), (see, e.g. Baulcombe, Science 297:2002-2003, 2002). The dsRNA molecules, e.g. siRNA, also can contain 3' overhangs, preferably 3'UU or 3'TT overhangs. In one embodiment, the siRNA molecules of the present invention do not include RNA molecules that comprise ssRNA greater than about 30-40 bases, about 40-50 bases, about 50 bases or more. In one embodiment, the siRNA molecules of the present invention are double stranded for more than about 25%, more than about 50%, more than about 60%, more than about 70%, more than about 80%, more than about 90% of their length. In some embodiments, a nucleic acid inhibitor of a gene identified in Table 1, 2 or 3 is any agent which binds to and inhibits the expression of mRNA of that gene identified in Table 1, 2 or 3, where the mRNA or a product of transcription of nucleic acid is encoded by SEQ. ID NOS:1-11 (Genbank Accession No. NM_000944; NM_021132.1; NM_006325; NM_006267.4; NM_002265.4, NM_001316; NM_003400.3; NM_003156.2, NM_020860.2, NM_032790.3, NM_002250.2).

In another embodiment, agents inhibiting the genes identified in Table 1, 2 or 3 are catalytic nucleic acid constructs, such as, for example ribozymes, which are capable of cleaving RNA transcripts and thereby preventing the production of wildtype protein. Ribozymes are targeted to and anneal with a particular sequence by virtue of two regions of sequence complementary to the target flanking the ribozyme catalytic site. After binding, the ribozyme cleaves the target in a site specific manner. The design and testing of ribozymes which specifically recognize and cleave sequences of the gene products described herein, for example, for the cleavage of the genes identified in Table 1, 2 or 3 or homologues or variants thereof can be achieved by techniques well known to those skilled in the art (for example Lieber and Strauss, (1995) Mol Cell Biol 15:540.551, the disclosure of which is incorporated herein by reference).

Pharmaceutical Compositions and Administration

In one embodiment, the invention provides a pharmaceutical composition comprising an agent that inhibits the activity of a protein encoded by a gene identified in Table 1, 2 or 3 and/or the expression of a gene identified in Table 1, 2 or 3 and a pharmaceutically acceptable carrier. The agent can be a small molecule, nucleic acid, nucleic acid analogue, protein, antibody, peptide, aptamer or variants or fragments thereof. Other forms of inhibitors include a nucleic acid agent which is an RNAi agent such as a siRNA, shRNA, miRNA, dsRNA or ribozyme or variants thereof.

In one embodiment, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like.

The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). In one embodiment, other ingredients can be added to pharmaceutical formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In a embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lignocamne to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylaminoethanol, histidine, procaine, to name a few.

Various delivery systems are known in the art and can be used to administer agent that inhibits the activity a candidate protein and/or the expression of a gene identified in Table 1, 2 or 3 of Table 1, 2 or 3, e.g., encapsulation in liposomes, microparticles, and microcapsules (see, e.g., Wu and Wu, J. Biol. Chem., 262:4429-4432 (1987)). The composition can be delivered in a vesicle, in particular a liposome (see, Langer, Science, 249:1527-1533 (1990); Treat et al., in Liposomes in the Therapy of Infectious Disease and Cancer, Lopez-Berestein and Fidler, eds. (Liss, New York 1989), pp. 353-365; Lopez-Berestein, ibid., pp. 317-327; see, generally, ibid.).

Pharmaceutical compositions can be administered by any known route. By way of example, the composition can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of the agents as disclosed herein such that it enters the animal's system and, thus, is subject to metabolism and other like processes, for example, subcutaneous administration.

Administration can be systemic or local. In addition, it can be desirable to introduce the pharmaceutical compositions of the invention into the central nervous system by any suitable route, including intraventricular and intrathecal injection; intraventricular injection can be facilitated by an intraventricular catheter, for example, attached to a reservoir, such as an Omcana reservoir. Pulmonary administration can also be employed, e.g., by use of an inhaler or nebulizer, and formulation with an aerosolizing agent.

In one embodiment, the pharmaceutical formulation to be used for therapeutic administration must be sterile. Sterility is readily accomplished by filtration through sterile filtration membranes (e.g., 0.2 micron membranes). The pH of the pharmaceutical formulation typically should be about from 6 to 8.

In one embodiment, the composition can be delivered in a controlled release system. In one embodiment, a pump can be used (see Langer, supra; Sefton, CRC Crit. Ref. Biomed. Eng., 14:201 (1987); Buchwald et al., Surgery, 88:507 (1980); Saudek et al., N. Engl. J. Med., 321:574 (1989)). In another embodiment, polymeric materials can be used (see, Medical Applications of Controlled Release, Langer and Wise, eds. (CRC Press, Boca Raton, Ha, 1974); Controlled Drug Bioavailability, Drug Product Design and Performance, Smolen and Ball, eds. (Wiley, New York 1984); Ranger and Peppas, Macromol. Sci. Rev. Macromol. Chem., 23:61 (1983); see also Levy et al., Science, 228:190 (1985); During et al., Ann. Neurol., 25:35 1 (1989); Howard et al., J. Neurosurg., 7 1:105 (1989)). Other controlled release systems are discussed in the review by Langer (Science, 249:1527-1533 (1990)). For examples of sustained release compositions, see U.S. Pat. No. 3,773,919, EP 58,481A, U.S. Pat. No. 3,887, 699, EP 158,277A, Canadian Patent No. 1176565, U. Sidman et al., Biopolymers 22:547 (1983) and R. Langer et al., Chem. Tech. 12:98 (1982).

The precise dose to be employed in the formulation will also depend on the route of administration, and the severity of hyperactivity or inappropriate immune response, and should be decided according to the judgment of the practitioner and each patient's circumstances. Effective doses can be extrapolated from dose-response curves derived from in vitro or animal model test systems.

The dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. For gene therapy, viral vector should be in the range of $1 \times 10^6$ to $10^{14}$ viral vector particles per application per patient.

In addition, in vitro or in vivo assays can optionally be employed to help identify optimal dosage ranges. The precise dose to be employed will also depend on the route of administration, and the seriousness of the condition being treated and should be decided according to the judgment of the practitioner and each subject's circumstances in view of, e.g., published clinical studies. Suitable effective dosage amounts, however, range from about 10 micrograms to about 5 grams about every 4 hour, although they are typically about 500 mg or less per every 4 hours. In one embodiment the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, or about 5.0 g, every 4 hours. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered. The compositions comprising agent that inhibits the activity of a protein encoded by a gene identified in Table 1, 2 or 3 and/or the expression of a gene identified in Table 1, 2 or 3, including expression vectors and/or viral vectors are suitably administered to the patient at one time or over a series of treatments. For purposes herein, a "therapeutically effective amount" of a composition comprising an agent that inhibits the activity of a protein encoded by a gene identified in Table 1, 2 or 3 and/or the expression of a gene identified in Table 1, 2 or 3 is an amount that is effective to reduce the amount of NFAT nuclear translocation, $Ca^{2+}$ influx and/or cytokine production by at least 20%, or reduce the symptom associated hyperactive or inappropriate immune response by at least 10%.

In an embodiment, the composition comprising an agent that inhibits the activity of a protein encoded by a gene identified in Table 1, 2 or 3 and/or the expression of a gene identified in Table 1, 2 or 3 is administered in combination with immunosuppressive therapies including, but not limited to, azathioprine, infliximab, omalizumab, daclizumab, adalimumab, eculizumab, efalizumab, natalizumab, and omalizumab. In another embodiment, the composition comprising agent that inhibits the activity of a protein encoded by a gene identified in Table 1, 2 or 3 and/or the expression of a gene identified in Table 1, 2 or 3 is administered in combination with immunosuppressive therapies and cyclophosphamide, chlorambucil, and/or rituximab.

Gene Therapy

In one embodiment, the agent that inhibits the activity of a protein encoded by a gene identified in Table 1, 2 or 3 and/or the expression of a gene identified in Table 1, 2 or 3 is administered to an individual by any one of several gene therapy techniques known to those of skill in the art. In general, gene therapy can be accomplished by either direct transformation of target cells within the mammalian subject (in vivo gene therapy) or transformation of cells in vitro and subsequent implantation of the transformed cells into the mammalian subject (ex vivo gene therapy). A viral vector carries anRNAi agent such as a shRNA or anti-sense oligonucleotide for a gene identified in Table 1, 2 or 3 under a tissue specific regulatory element is administered to an individual. The tissue specific regulatory element allows the expression of the RNAi agent in the target cells, for example, the lymph nodes.

The principles of gene therapy are disclosed by Oldham, R. K. (In: Principles of Biotherapy, Raven Press, N.Y., 1987), and similar texts. Disclosures of the methods and uses for gene therapy are provided by Boggs, S. S. (Int. J. Cell Clon. 8:80-96 (1990)); Karson, E. M. (Biol. Reprod. 42:39-49 (1990)); Ledley, F. D., In: Biotechnology, A Comprehensive Treatise, volume 7B, Gene Technology, VCH Publishers, Inc. NY, pp 399-458 (1989)), all of which references are incorporated herein by reference.

The nucleic acid encoding an RNAi agent such as shRNA can be introduced into the somatic cells of an animal (particularly mammals including humans) in gene therapy. Most preferably, viral or retroviral vectors are employed for as the transfer vehicle this purpose. The gene therapy virus can be in the form of an adenovirus, adeno-associated virus or lentivirus.

Retroviral vectors are a common mode of delivery and in this context are retroviruses from which all viral genes have been removed or altered so that no viral proteins are made in cells infected with the vector. Viral replication functions are provided by the use of retrovirus "packaging" cells that produce all of the viral proteins but that do not produce infectious virus.

Introduction of the retroviral vector DNA into packaging cells results in production of virions that carry vector RNA and can infect target cells, but such that no further virus spread occurs after infection. To distinguish this process from a natural virus infection where the virus continues to replicate and spread, the term transduction rather than infection is often used.

In one embodiment, the method of treating MN described herein provides a recombinant lentivirus for the delivery and expression of an RNAi agent in either dividing or non-dividing mammalian cells. The HIV-1 based lentivirus can effectively transduce a broader host range than the Moloney Leukemia Virus (MoMLV)-base retroviral systems. Preparation of the recombinant lentivirus can be achieved using the pLenti4/V5-DEST™, pLenti6/V5-DEST™ or pLenti vectors together with ViraPower™ Lentiviral Expression systems from Invitrogen.

Examples of use of lentiviral vectors for gene therapy for inherited disorders and various types of cancer, and these references are hereby incorporated by reference (Klein, C. and Baum, C. (2004). Hematol. J., 5, 103-111; Zufferey, R et. al. (1997). Nat. Biotechnol., 15, 871-875; Morizono, K. et. al. (2005). Nat. Med., 11, 346-352; Di Domenico, C. et. al. (2005), Hum. Gene Ther., 16, 81-90; Kim, E. Y., et. al., (2004). Biochem. Biophys. Res. Comm., 318, 381-390).

Non-retroviral vectors also have been used in genetic therapy. One such alternative is the adenovirus (Rosenfeld, M. A., et al., Cell 68:143155 (1992); Jaffe, H. A. et al., Nature Genetics 1:372-378 (1992); Lemarchand, P. et al., Proc. Natl. Acad. Sci. USA 89:6482-6486 (1992)). Major advantages of adenovirus vectors are their potential to carry large segments of DNA (36 Kb genome), a very high titre ($10^{11}$/ml), ability to infect non-replicating cells, and suitability for infecting tissues in situ, especially in the lung. The most striking use of this vector so far is to deliver a human cystic fibrosis transmembrane conductance regulator (CFTR) gene by intratracheal instillation to airway epithelium in cotton rats (Rosenfeld, M. A., et al., Cell 63:143-155 (1992)). Similarly, herpes viruses may also prove valuable for human gene therapy (Wolfe, J. H. et al., Nature Genetics 1:379-384 (1992)). Of course, any other suitable viral vector may be used for genetic therapy with the present invention.

U.S. Pat. No. 6,531,456 provides methods for the successful transfer of a gene into a solid tumor cell using recombinant AAV virions. Generally, the method described in U.S. Pat. No. 6,531,456 allows for the direct, in vivo injection of recombinant AAV virions into tumor cell masses, e.g., by intra-tumoral injection. The invention also provides for the simultaneous delivery of a second gene using the recombinant AAV virions, wherein the second gene is capable of providing an ancillary therapeutic effect when expressed within the transduced cell. U.S. Pat. No. 6,531,456 is hereby incorporated by reference in its entirety.

The viron used for gene therapy can be any viron known in the art including but not limited to those derived from adenovirus, adeno-associated virus (AAV), retrovirus, and lentivirus. Recombinant viruses provide a versatile system for gene expression studies and therapeutic applications.

The recombinant AAV virions described above, including the DNA of interest, can be produced using standard methodology, known to those of skill in the art. The methods generally involve the steps of (1) introducing an AAV vector into a host cell; (2) introducing an AAV helper construct into the host cell, where the helper construct includes AAV coding regions capable of being expressed in the host cell to complement AAV helper functions missing from the AAV vector; (3) introducing one or more helper viruses and/or accessory function vectors into the host cell, wherein the helper virus and/or accessory function vectors provide accessory functions capable of supporting efficient recombinant AAV ("rAAV") virion production in the host cell; and (4) culturing the host cell to produce rAAV virions. The AAV vector, AAV helper construct and the helper virus or accessory function vector(s) can be introduced into the host cell either simultaneously or serially, using standard transfection techniques. Using rAAV vectors, genes can be delivered into a wide range of host cells including many different human and non-human cell lines or tissues. Because AAV is non-pathogenic and does not illicit an immune response, a multitude of pre-clinical studies have reported excellent safety profiles. rAAVs are capable of transducing a broad range of cell types and transduction is not dependent on active host cell division. High titers, >10⁸ viral particle/ml, are easily obtained in the supernatant and $10^{11}$-$10^{12}$ viral particle/ml with further concentration. The transgene is integrated into the host genome so expression is long term and stable.

A simplified system for generating recombinant adenoviruses is presented by He T C. et. al. Proc. Natl. Acad. Sci. USA 95:2509-2514, 1998. The gene of interest is first cloned into a shuttle vector, e.g. pAdTrack-CMV. The resultant plasmid is linearized by digesting with restriction endonuclease Pme I, and subsequently cotransformed into *E. coli*. BJ5183 cells with an adenoviral backbone plasmid, e.g. pAdEasy-1 of Stratagene's AdEasy™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells(E1-transformed human embryonic kidney cells) or 911 (E1-transformed human embryonic retinal cells) (Human Gene Therapy 7:215-222, 1996). Recombinant adenovirus are generated within the HEK 293 cells.

The use of alternative AAV serotypes other than AAV-2 (Davidson et al (2000), Proc. Natl. Acad. Sci. USA 97(7) 3428-32; Passini et al (2003), J. Virol. 77(12):7034-40) has demonstrated different cell tropisms and increased transduction capabilities. With respect to brain cancers, the development of novel injection techniques into the brain, specifically convection enhanced delivery (CED; Bobo et al (1994), Proc. Natl. Acad. Sci. USA 91(6):2076-80; Nguyen et al (2001), Neuroreport 12(9):1961-4), has significantly enhanced the ability to transduce large areas of the brain with an AAV vector.

Large scale preparation of AAV vectors is made by a three-plasmid cotransfection of a packaging cell line: AAV vector carrying a DNA coding sequence for an antisense oligonucleotide to hnRNPLL or an siRNA hnRNPLL nucleic acid molecule, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et. al., 2001, Human Gene therapy 12; 71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsCl gradients.

Pharmaceutical compositions used in the methods described herein can be delivered systemically via in vivo gene therapy. A variety of methods have been developed to accomplish in vivo transformation including mechanical means (e.g, direct injection of nucleic acid into target cells or particle bombardment), recombinant viruses, liposomes, and receptor-mediated endocytosis (RMF) (for reviews, see Chang et al. 1994 Gastroenterol. 106:1076-84; Morsy et al. 1993 JAMA 270:2338-45; and Ledley 1992 J. Pediatr. Gastroenterol. Nutr. 14:328-37).

Another gene transfer method for use in humans is the transfer of plasmid DNA in liposomes directly to human cells in situ (Nabel, E. G., et al., Science 249:1285-1288 (1990)). Plasmid DNA should be easy to certify for use in human gene therapy because, unlike retroviral vectors, it can be purified to homogeneity. In addition to liposome-mediated DNA transfer, several other physical DNA transfer methods, such as those targeting the DNA to receptors on cells by conjugating the plasmid DNA to proteins, have shown promise in human gene therapy (Wu, O. Y., et al., J. Biol. Chem. 266:14338-14342 (1991); Curiel, D. T., et al., Proc. Natl. Acad. Sci. USA, 88:8850-8854 (1991)).

For gene therapy viruses, the dosage ranges from $10^6$ to $10^{14}$ particles per application. Alternatively the biolistic gene gun method of delivery may be used. The gene gun is a device for injecting cells with genetic information, originally designed for plant transformation. The payload is an elemental particle of a heavy metal coated with plasmid DNA. This technique is often simply referred to as biolistics. Another instrument that uses biolistics technology is the PDS-1000/He particle delivery system. The proteins, expression vector, and/or gene therapy virus can be coated on minute gold particles, and these coated particles are "shot" into biological tissues such as hemangiomas and melanoma under high pressure. An example of the gene gun-based method is described for DNA based vaccination of cattle by Loehr B. I. et. al. J. Virol. 2000, 74:6077-86.

Materials and Methods for the construction of the expression vectors NFAT-GFP and Stim1-RFP, and the transfection of expression vectors into Hela cells are well known to one skilled in the art and are also described in Okamura, et. al., Mol. Cell, 2000, 6:539-50; Aramburu, et. al., Science, 1999, 285:2129-33; Gwack Y, et. al., Nature, 2006, 441:646-50, Oh-hora et al, Nature immunology 2008, 9:432-43; US Patent Application Nos. US2007/0031814 and PCT/US2007/000280. These references are hereby incorporated by reference in their entirety.

More specifically, the expression vector Stim1-RFP was constructed by the following method. Full length murine Stim1 cDNA (Oh-hora et al, Nature immunology 2008, 9:432-43) was PCR-amplified and cloned into pDSRed-Monomer-N1 (Clontech) using the Xho1 and BamH1 sites.

The expression vector Orai-FLAG was constructed by the following method and by any molecular methods known to one skilled in the art. Full length human Orai1 cDNA (Feske et al, Nature 2006, 441:179-85) was PCR-amplified and cloned into pFLAG-CMV2 (Sigma) using the Not1 and Xho1 sites.

Hela cell line expressing NFAT1, Stim1, and Orai1: HeLa 13.10. A monoclonal population of HeLa NFAT1(1-460)-GFP cells stably expressing the amino terminal signal responsive domain of NFAT1 fused to GFP (Gwack et al, Nature 2006, 441:646-50) were engineered to stably express full length Stim1-RFP and transiently transfected with full length Orai1-FLAG 1; efficiency of Orai1-FLAG expression was quantitated by anti-FLAG immunocytochemistry at 48 h post transfection (75%±6.7) and 96 h post transfection (42%±8). Cells were maintained at 37° C./10% $CO_2$ in DMEM 10% bovine calf serum (BCS), penicillin/streptomycin, HEPES and β-mercaptoethanol/L-glutamine and 100 µg/mL Hygromycin B. Hygromycin B was removed 16 h before Orai1-FLAG transfection. All experiments were performed with cells kept at a passage number under 6.

HeLa 13.10 cells stably expressing NFAT1-GFP and Stim1-RFP and transiently expressing Orai1-FLAG were reverse transfected with 20 nM siRNA using Hiperfect Transfection Reagent (Qiagen) by robotic transfer of cells to 384-well plates (5000-6000 cells/well) pre-arrayed with siRNA corresponding to the annotated human genome (Dharmacon). 72 h post transfection with siRNA, cells were stimulated with thapsigargin (250 nM for 90 minutes at room temperature) to induce NFAT1-GFP nuclear translocation; cells were fixed with 3% paraformaldehyde, permeablized with 0.2% Triton-X 100, stained with the DNA intercalating dye DAPI and assessed for NFAT1-GFP nuclear translocation by fluorescent microscopy. Images were acquired using the ImageXpress Micro automated imaging system (Molecular Devices) using a 10× objective and analyzed using the Translocation Application module of MetaXpress software version 6.1 (Molecular Devices). Cytoplasmic to nuclear translocation was assessed by calculating a correlation of intensity between NFAT1-GFP fluorescence and DAPI staining: cells were scored as positive for nuclear NFAT1 when >60% of NFAT1-GFP fluorescence coincided with DAPI fluorescence. Each data point represents an average of at least 1200 individual cells per well and averaged for duplicate wells.

The references cited herein and throughout the specification are incorporated herein by reference.

TABLE 1

| Stock_ID | Row | Type | Z score_A | Z score_B | Screen + | Gene Symbol | Entrez Gene ID | Accession # | Catalog # |
|---|---|---|---|---|---|---|---|---|---|
| PL-50049 | L11 | X | −3.09 | −1.83 | W | AB026190 | 27252 | NM_014458 | M-004893-00 |
| PL-50049 | J12 | X | −3.90 | −2.18 | W | ABLIM2 | 84448 | NM_032432 | M-014892-00 |
| PL-50047 | A21 | X | −3.03 | −1.80 | W | ACLY | 47 | NM_001096 | M-004915-00 |
| PL-50049 | F16 | X | −2.11 | −1.83 | W | ACY1L2 | 135293 | XM_072402 | M-024889-00 |
| PL-50049 | F02 | X | −3.49 | −2.11 | W | ADCY4 | 196883 | NM_139247 | M-006800-00 |
| PL-50001 | G15 | X | −3.55 | −2.27 | W | ADK | 132 | NM_001123 | M-004733-02 |
| PL-50004 | C05 | X | −2.16 | −2.22 | W | ADRA2B | 151 | NM_000682 | M-005423-01 |
| PL-50001 | I23 | X | −3.16 | −2.17 | W | AKAP11 | 11215 | NM_016248 | M-009277-01 |
| PL-50049 | D14 | X | −1.58 | −2.77 | W | AKR1CL1 | 340811 | XM_291723 | M-029709-00 |
| PL-50049 | F08 | X | −2.82 | −1.74 | W | ALS2CR13 | 150864 | NM_173511 | M-018538-00 |
| PL-50016 | D02 | X | −2.44 | −2.24 | W | AMH | 268.00 | NM_000479 | M-010991-00 |
| PL-50079 | J04 | X | −2.46 | −2.33 | W | AMIGO2 | 347902 | NM_181847 | M-018701-00 |
| PL-50058 | J08 | X | −2.91 | −1.32 | W | ANKFY1 | 51479 | NM_016376 | M-013161-00 |
| PL-50001 | M17 | X | −1.97 | −3.09 | W | ANKK1 | 255329 | NM_178510 | M-004930-01 |
| PL-50062 | A20 | X | −2.10 | −1.94 | W | ANKMY2 | 57037 | NM_020319 | M-013766-00 |
| PL-50072 | O18 | X | −2.66 | −2.06 | W | AP1S3 | 130340 | NM_178814 | M-018537-00 |
| PL-50051 | D07 | X | −0.16 | −2.82 | W | AP3B2 | 8120 | NM_004644 | M-021444-00 |
| PL-50060 | G04 | X | −1.92 | −2.66 | W | APG16L | 55054 | NM_017974 | M-021033-00 |
| PL-50020 | J11 | X | −2.32 | −3.58 | W | APOBEC1 | 339 | NM_001644 | M-011573-00 |
| PL-50047 | K17 | X | −2.04 | −2.52 | W | APXL | 357 | NM_001649 | M-011577-00 |
| PL-50052 | N16 | X | −2.02 | −2.39 | W | AQR | 9716 | NM_014691 | M-022214-00 |
| PL-50061 | P09 | X | −2.09 | −2.98 | W | ARHGAP15 | 55843 | NM_018460 | M-018019-00 |
| PL-50060 | D05 | X | −1.31 | −4.57 | W | ARHGAPI7 | 55114 | NM_018054 | M-008335-00 |
| PL-50008 | M17 | X | −1.83 | −2.56 | W | ARHGDIA | 396 | NM_004309 | M-016253-00 |
| PL-50060 | P12 | X | −1.85 | −2.81 | W | ARL10C | 55207 | NM_018184 | M-020294-00 |
| PL-50067 | A12 | X | −2.08 | −2.58 | W | ARMC2 | 84071 | NM_032131 | M-018191-00 |
| PL-50054 | E09 | X | −1.82 | −2.26 | W | ARPP-21 | 10777 | NM_016300 | M-016091-00 |
| PL-50059 | A19 | X | −2.87 | −2.80 | W | ARS2 | 51593 | NM_015908 | M-019234-00 |
| PL-50072 | J21 | X | −2.98 | −2.50 | W | ASB10 | 136371 | NM_080871 | M-007725-00 |
| PL-50051 | L06 | X | −2.17 | −1.94 | W | ASMTL | 8623 | NM_004192 | M-012663-00 |
| PL-50089 | G02 | X | −3.39 | −1.60 | W | ASTL | 431659 | NM_001002036 | M-032349-00 |
| PL-50062 | L11 | X | −1.59 | −2.02 | W | ATP10D | 57205 | NM_020453 | M-018004-00 |
| PL-50047 | O19 | X | −3.42 | −1.02 | W | ATP2B4 | 493 | NM_001684 | M-006118-00 |
| PL-50057 | M21 | X | −0.60 | −3.79 | W | ATP5S | 27109 | NM_015684 | M-020544-00 |
| PL-50064 | G11 | X | −2.18 | −4.15 | W | AZ2 | 64343 | NM_022461 | M-014092-00 |
| PL-50062 | E06 | X | −1.54 | −3.01 | W | BBX | 56987 | NM_020235 | M-015289-00 |
| PL-50070 | I20 | X | −2.83 | −2.20 | W | BC002942 | 91289 | NM_033200 | M-015085-00 |
| PL-50057 | K14 | X | −2.54 | −2.67 | W | BC-2 | 27243 | NM_014453 | M-020247-00 |
| PL-50062 | G05 | X | −2.27 | −1.90 | W | BEXL1 | 56271 | XM_043653 | M-024780-00 |
| PL-50047 | K18 | X | −1.40 | −3.63 | W | BFSP1 | 631 | NM_001195 | M-011218-00 |
| PL-50017 | A09 | X | −2.42 | −2.70 | W | BMP15 | 9210 | NM_005448 | M-012018-01 |
| PL-50075 | G08 | X | −2.90 | −2.75 | W | BMPER | 168667 | NM_133468 | M-021489-00 |
| PL-50008 | A06 | X | −2.04 | −2.46 | W | BRD8 | 10902 | NM_006696 | M-006377-00 |
| PL-50063 | P09 | X | −3.57 | −2.70 | W | BRUNOL6 | 60677 | NM_052840 | M-015854-00 |
| PL-50020 | F10 | X | −2.48 | −1.85 | W | BSCL2 | 26580 | NM_032667 | M-016749-00 |
| PL-50053 | H23 | X | −2.62 | −2.25 | W | BTN3A3 | 10384 | NM_006994 | M-021359-00 |
| PL-50061 | A19 | X | −3.13 | −2.11 | W | C10ORF59 | 55328 | NM_018363 | M-021211-00 |
| PL-50070 | J06 | X | −2.62 | −2.52 | W | C10ORF94 | 93426 | NM_130784 | M-015298-00 |
| PL-50062 | K11 | X | −2.68 | −2.65 | W | C11ORF17 | 56672 | NM_020642 | M-015631-00 |
| PL-50063 | H04 | X | −1.74 | −2.73 | W | C13ORF10 | 64062 | NM_022118 | M-019088-00 |
| PL-50069 | D21 | X | −1.91 | −2.80 | W | C14ORF126 | 112487 | NM_080664 | M-021299-00 |
| PL-50075 | F13 | X | −2.34 | −3.25 | W | C14ORF147 | 171546 | NM_138288 | M-017156-00 |
| PL-50070 | A10 | X | −2.77 | −2.54 | W | C14ORF43 | 91748 | NM_194278 | M-031938-00 |
| PL-50070 | B11 | X | −2.37 | −2.86 | W | C14ORF73 | 91828 | XM_040910 | M-022006-00 |
| PL-50071 | G02 | X | −2.58 | −2.56 | W | C14ORF8 | 122664 | NM_173846 | M-017754-00 |
| PL-50053 | G11 | X | −3.12 | −2.14 | W | C14ORF92 | 9878 | XM_375045 | M-021236-00 |
| PL-50064 | P15 | X | −2.47 | −2.41 | W | C16ORF23 | 79006 | NM_024042 | M-014274-00 |
| PL-50004 | G11 | X | −2.61 | −2.46 | W | C17ORF35 | 8834 | NM_003876 | M-005440-01 |
| PL-50080 | M11 | X | −2.47 | −1.66 | W | C18ORF34 | 374864 | NM_198995 | M-032008-00 |
| PL-50060 | K20 | X | −2.53 | −1.97 | W | C19ORF24 | 55009 | NM_017914 | M-020936-00 |
| PL-50020 | B06 | X | −2.95 | −3.27 | W | C21ORF107 | 54014 | NM_018963 | M-010963-00 |
| PL-50059 | K06 | X | −2.50 | −1.66 | W | C21ORF45 | 54069 | NM_018944 | M-020789-00 |
| PL-50053 | K20 | X | −1.98 | −2.27 | W | C21ORF6 | 10069 | NM_016940 | M-013856-00 |
| PL-50069 | P16 | X | −2.84 | −2.91 | W | C21ORF84 | 114038 | NM_153752 | M-016161-00 |
| PL-50051 | L20 | X | −1.99 | −2.78 | W | C4ORF8 | 8603 | NM_003704 | M-019541-00 |
| PL-50075 | K06 | X | −2.03 | −2.45 | W | C5ORF11 | 167410 | NM_153234 | M-018373-00 |
| PL-50061 | G11 | X | −2.72 | −3.09 | W | C6ORF110 | 55362 | XM_371822 | M-025105-00 |

TABLE 1-continued

| Stock_ID | Row | Type | Z score_A | Z score_B | Screen + | Gene Symbol | Entrez Gene ID | Accession # | Catalog # |
|---|---|---|---|---|---|---|---|---|---|
| PL-50069 | D23 | X | −2.08 | −2.05 | W | C6ORF51 | 112495 | NM_138408 | M-015508-00 |
| PL-50072 | F23 | X | −2.27 | −2.07 | W | C6ORF57 | 135154 | NM_145267 | M-015985-00 |
| PL-50065 | B06 | X | −2.19 | −2.05 | W | C6ORF59 | 79992 | NM_024929 | |
| PL-50062 | O17 | X | −1.95 | −2.24 | W | C8ORF4 | 56892 | NM_020130 | M-015557-00 |
| PL-50072 | L10 | X | −2.48 | −2.75 | W | C9ORF115 | 138428 | XM_059972 | M-026208-00 |
| PL-50078 | D16 | X | −2.29 | −1.86 | W | C9ORF150 | 286343 | NM_203403 | M-031930-00 |
| PL-50074 | N18 | X | −2.11 | −3.35 | W | C9ORF84 | 158401 | NM_173521 | M-018530-00 |
| PL-50066 | B20 | X | −2.77 | −1.61 | W | CABLES2 | 81928 | NM_031215 | M-032282-00 |
| PL-50020 | A21 | X | −4.27 | −1.56 | W | CACNA1A | 773 | NM_000068 | M-006121-01 |
| PL-50057 | M05 | X | −2.50 | −1.67 | W | CACNG4 | 27092 | NM_014405 | M-012519-00 |
| PL-50051 | L10 | X | −2.82 | −1.93 | W | CADPS | 8618 | NM_003716 | M-019218-00 |
| PL-50006 | M11 | X | −2.76 | −2.97 | W | CARD12 | 58484 | NM_021209 | M-004396-00 |
| PL-50021 | J17 | X | −2.30 | −3.97 | W | CAV3 | 859 | NM_001234 | M-011229-00 |
| PL-50073 | H05 | X | −2.78 | −2.55 | W | CBLN2 | 147381 | NM_182511 | |
| PL-50006 | O05 | X | −3.04 | −1.72 | W | CBX6 | 23466 | NM_014292 | M-009555-00 |
| PL-50004 | K15 | X | −2.33 | −3.05 | W | CCR6 | 1235 | NM_004367 | M-005453-00 |
| PL-50006 | O19 | X | −2.27 | −2.03 | W | CD151 | 977 | NM_004357 | M-003637-02 |
| PL-50047 | A18 | X | −2.22 | −2.55 | W | CD1E | 913 | NM_030893 | M-014647-00 |
| PL-50017 | I09 | X | −2.00 | −2.04 | W | CD3G | 917 | NM_000073 | M-011005-00 |
| PL-50017 | I15 | X | −1.87 | −3.86 | W | CD5 | 921 | NM_014207 | M-007848-01 |
| PL-50014 | B06 | X | −3.64 | −2.09 | W | CD74 | 972.00 | NM_004355 | M-012667-00 |
| PL-50073 | B10 | X | −2.54 | −1.73 | W | CDC42EP5 | 148170 | NM_145057 | |
| PL-50006 | K08 | X | −2.95 | −2.84 | W | CDH9 | 1007 | NM_016279 | M-013169-00 |
| PL-50071 | E05 | X | −2.66 | −3.17 | W | CENTG1 | 116986 | NM_014770 | M-021010-00 |
| PL-50047 | B13 | X | −3.12 | −1.98 | W | CFL2 | 1073 | NM_021914 | M-019078-00 |
| PL-50067 | N08 | X | −2.59 | −2.83 | W | CHCHD5 | 84269 | NM_032309 | M-014849-00 |
| PL-50015 | G18 | X | −2.23 | −2.61 | W | CHD4 | 1108.00 | NM_001273 | M-009774-00 |
| PL-50053 | L12 | X | −2.50 | −2.99 | W | CHERP | 10523 | NM_006387 | M-016176-00 |
| PL-50015 | G16 | X | −2.93 | −2.08 | W | CHFR | 55743.00 | NM_018223 | M-007018-01 |
| PL-50004 | M21 | X | −2.16 | −1.86 | W | CHRM3 | 1131 | NM_000740 | M-005464-00 |
| PL-50018 | I11 | X | −2.72 | −2.11 | W | CHRNA4 | 1137 | NM_000744 | M-006138-01 |
| PL-50008 | D23 | X | −2.49 | −2.10 | W | CKN1 | 1161 | NM_000082 | M-011008-00 |
| PL-50047 | F05 | X | −0.87 | −3.50 | W | CLCN4 | 1183 | NM_001830 | M-006152-00 |
| PL-50057 | M11 | X | −0.66 | −4.26 | W | CLUL1 | 27098 | NM_014410 | M-017042-00 |
| PL-50054 | P09 | X | −2.07 | −2.02 | W | CMRF-35H | 11314 | NM_007261 | M-012778-00 |
| PL-50012 | P10 | X | −2.55 | −2.13 | W | COMT | 1312 | NM_000754 | M-009520-00 |
| PL-50047 | L05 | X | −2.66 | −1.83 | W | COX8A | 1351 | NM_004074 | M-011819-00 |
| PL-50058 | C06 | X | −1.80 | −2.20 | W | CRBN | 51185 | NM_016302 | M-021086-00 |
| PL-50004 | O11 | X | −3.31 | −1.98 | W | CRHR2 | 1395 | NM_001883 | M-005470-01 |
| PL-50018 | I12 | X | −2.54 | −2.67 | W | CRSP2 | 9282 | NM_004229 | M-011928-00 |
| PL-50021 | K20 | X | −2.15 | −2.49 | W | CRSP3 | 9439 | NM_004830 | M-013220-00 |
| PL-50018 | I10 | X | −2.43 | −2.89 | W | CRSP6 | 9440 | NM_004268 | M-006312-01 |
| PL-50018 | B18 | X | −6.60 | −1.80 | W | CRYBA2 | 1412 | NM_005209 | M-012024-00 |
| PL-50021 | K12 | X | −2.72 | −1.44 | W | CRYBB1 | 1414 | NM_001887 | M-011629-00 |
| PL-50018 | B16 | X | −2.65 | −2.48 | W | CRYBB3 | 1417 | NM_004076 | M-006480-01 |
| PL-50018 | B12 | X | −2.55 | −3.76 | W | CRYGC | 1420 | NM_020989 | M-013142-00 |
| PL-50010 | J07 | X | −2.43 | −2.25 | W | CSAD | 51380 | NM_015989 | M-008314-00 |
| PL-50021 | I10 | X | 2.08 | 2.02 | W | CST7 | 8530 | NM_003650 | M-017236-00 |
| PL-50051 | H11 | X | −2.42 | −2.76 | W | CXORF12 | 8269 | NM_003492 | M-011428-00 |
| PL-50047 | P10 | X | −3.46 | −2.51 | W | CYLC1 | 1538 | XM_1088636 | M-024769-00 |
| PL-50012 | N08 | X | −3.15 | −2.69 | W | CYP1A1 | 1543 | NM_000499 | M-004790-01 |
| PL-50047 | N12 | X | −2.58 | −3.29 | W | CYP3A5 | 1577 | NM_000777 | M-009684-00 |
| PL-50014 | G17 | X | −2.77 | −2.17 | W | D2S448 | 7837.00 | XM_056455 | M-022772-00 |
| PL-50021 | E20 | X | −2.67 | −1.85 | W | DAAM1 | 23002 | NM_014992 | M-012925-00 |
| PL-50017 | O15 | X | −2.15 | −2.16 | W | DBI | 1622 | NM_020548 | M-006488-00 |
| PL-50063 | B23 | X | −2.01 | −1.97 | W | DC2 | 58505 | NM_021227 | M-027193-00 |
| PL-50053 | G13 | X | −3.37 | −2.98 | W | DDX46 | 9879 | NM_014829 | M-021234-00 |
| PL-50047 | H12 | X | −3.31 | −1.94 | W | DHPS | 1725 | NM_001930 | M-006670-00 |
| PL-50070 | K14 | X | −2.81 | −2.09 | W | KFZP434B123 | 91156 | NM_178275 | M-018250-00 |
| PL-50067 | M17 | X | −2.22 | −2.32 | W | KFZP4341211 | 83723 | NM_031478 | M-003996-00 |
| PL-50078 | A08 | X | −3.07 | −2.03 | W | KFZP686P028 | 285190 | NM_182588 | M-018854-00 |
| PL-50067 | P23 | X | −2.28 | −3.62 | W | KFZP761B151 | 84248 | NM_032288 | M-018604-00 |
| PL-50047 | H04 | X | −0.84 | −3.07 | W | DLAT | 1737 | NM_001931 | M-008490-00 |
| PL-50012 | J02 | X | −2.78 | −1.78 | W | DNM1L | 10059 | NM_005690 | M-012092-01 |
| PL-50015 | D06 | X | −2.37 | −2.28 | W | DUSP16 | 80824.00 | NM_030640 | M-007890-00 |
| PL-50015 | D04 | X | −3.96 | −2.15 | W | DUSP18 | 150290.00 | NM_152511 | M-007891-00 |
| PL-50008 | J19 | X | −2.31 | −2.93 | W | DUX1 | 26584 | NM_012146 | M-019955-00 |
| PL-50057 | C13 | X | −3.26 | −2.30 | W | DUX5 | 26581 | NM_012149 | M-019904-00 |
| PL-50014 | G08 | X | −2.02 | −2.27 | W | DVL3 | 1857.00 | NM_004423 | M-004070-00 |
| PL-50062 | K04 | X | −1.79 | −2.87 | W | E(Y)2 | 56943 | NM_020189 | M-018808-00 |
| PL-50058 | J09 | X | −2.00 | −2.33 | W | E2IG2 | 51287 | NM_016565 | M-021148-00 |
| PL-50068 | O21 | X | −2.47 | −3.28 | W | EBPL | 84268 | NM_032565 | M-014920-00 |
| PL-50063 | O20 | X | −2.25 | −1.71 | W | EPB41L5 | 57669 | NM_020909 | M-010729-00 |
| PL-50017 | H14 | X | −2.63 | −3.25 | W | EREG | 2069 | NM_001432 | M-011268-00 |
| PL-50001 | P14 | X | −0.93 | −3.04 | W | ERK8 | 225689 | NM_139021 | M-004807-01 |
| PL-50021 | F20 | X | −2.24 | −3.12 | W | ESRRBL1 | 55081 | NM_018010 | M-015367-00 |
| PL-50064 | D10 | X | −3.04 | −2.71 | W | ET | 79157 | NM_024311 | M-014329-00 |

TABLE 1-continued

| Stock_ID | Row | Type | Z score_A | Z score_B | Screen + | Gene Symbol | Entrez Gene ID | Accession # | Catalog # |
|---|---|---|---|---|---|---|---|---|---|
| PL-50089 | H08 | X | −2.63 | −2.63 | W | EVI5 | 7813 | NM_005665 | M-032510-00 |
| PL-50067 | E18 | X | −2.76 | −2.42 | W | FAM14A | 83982 | NM_032036 | M-014773-00 |
| PL-50052 | F08 | X | −3.64 | −2.59 | W | FAM38A | 9780 | NM_014745 | M-020870-00 |
| PL-50015 | K07 | X | −2.52 | −2.30 | W | FBXL20 | 84961.00 | NM_032875 | M-015029-00 |
| PL-50015 | G02 | X | −2.70 | −3.21 | W | FBXL3P | 26223.00 | NM_012159 | M-012423-00 |
| PL-50015 | E04 | X | −2.37 | −1.84 | W | FBXO22 | 26263.00 | NM_012170 | M-010812-01 |
| PL-50055 | L14 | X | −3.13 | −0.76 | W | FBXO46 | 23403 | XM_371179 | M-023753-00 |
| PL-50021 | B02 | X | −4.26 | −2.10 | W | FCGR3A | 2214 | NM_000569 | M-016308-00 |
| PL-50017 | D20 | X | −2.38 | −3.61 | W | FGF14 | 2259 | NM_004115 | M-011860-00 |
| PL-50017 | B16 | X | −3.45 | −2.97 | W | FGF7 | 2252 | NM_002009 | M-011659-00 |
| PL-50072 | H13 | X | −2.47 | −3.34 | W | FKBP1C | 135521 | XM_059776 | M-028635-00 |
| PL-50060 | C12 | X | −1.71 | −2.56 | W | FLJ10159 | 55084 | NM_018013 | M-021094-00 |
| PL-50060 | D19 | X | −3.09 | −1.32 | W | FLJ10352 | 55125 | NM_018069 | M-032250-00 |
| PL-50059 | J05 | X | −2.99 | −1.80 | W | FLJ10613 | 54552 | NM_019067 | M-015743-00 |
| PL-50001 | N08 | X | −2.62 | −2.33 | W | FLJ10842 | 55750 | NM_018238 | M-007256-00 |
| PL-50060 | B14 | X | −1.94 | −2.52 | W | FLJ11126 | 55308 | NM_018332 | M-015868-00 |
| PL-50061 | A09 | X | −3.15 | −1.98 | W | FLJ11193 | 55322 | NM_018356 | M-021223-00 |
| PL-50064 | F11 | X | −2.54 | −2.12 | W | FLJ12517 | 65094 | NM_023007 | M-014238-00 |
| PL-50059 | C04 | X | −2.27 | −2.61 | W | FLJ20152 | 54463 | NM_019000 | M-016936-00 |
| PL-50059 | P23 | X | −2.32 | −4.10 | W | FLJ20485 | 54517 | NM_019042 | M-015341-00 |
| PL-50060 | M09 | X | −2.74 | −2.48 | W | FLJ20509 | 54956 | NM_017851 | M-020837-01 |
| PL-50060 | M21 | X | −2.62 | −1.68 | W | FLJ20519 | 54964 | NM_017860 | M-016312-00 |
| PL-50066 | G23 | X | −2.48 | −2.37 | W | FLJ20972 | 80098 | NM_025030 | M-014556-00 |
| PL-50066 | O12 | X | −2.65 | −3.61 | W | FLJ22688 | 80199 | NM_025129 | M-016342-00 |
| PL-50065 | P09 | X | −1.79 | −2.78 | W | FLJ23554 | 79864 | NM_024806 | |
| PL-50074 | C18 | X | −2.54 | −2.85 | W | FLJ25286 | 153443 | NM_152546 | M-015445-00 |
| PL-50072 | P23 | X | −2.72 | −2.62 | W | FLJ32356 | 144717 | NM_144671 | M-015976-00 |
| PL-50073 | N18 | X | −1.95 | −2.38 | W | FLJ32421 | 148362 | NM_144695 | |
| PL-50073 | L02 | X | −2.70 | −2.68 | W | FLJ32569 | 148811 | NM_152491 | |
| PL-50076 | B12 | X | −2.68 | −2.73 | W | FLJ32682 | 220081 | NM_182542 | M-018973-00 |
| PL-50073 | B05 | X | −2.02 | −1.72 | W | FLJ32734 | 146849 | NM_144681 | |
| PL-50074 | C09 | X | −2.94 | −2.73 | W | FLJ33814 | 150275 | NM_173510 | M-018556-00 |
| PL-50078 | A05 | X | −2.34 | −2.88 | W | FLJ34690 | 284034 | NM_182567 | M-018978-00 |
| PL-50075 | A23 | X | −1.99 | −2.64 | W | FLJ35757 | 162333 | NM_152598 | M-007150-00 |
| PL-50075 | K07 | X | −2.32 | −2.31 | W | FLJ35838 | 163479 | NM_173532 | M-018510-00 |
| PL-50074 | F04 | X | −3.13 | −1.97 | W | FLJ35843 | 160762 | NM_152591 | M-016858-00 |
| PL-50071 | D02 | X | −2.23 | −3.04 | W | FLJ35961 | 127294 | NM_152372 | M-017014-00 |
| PL-50078 | C15 | X | −1.88 | −3.07 | W | FLJ36878 | 284114 | NM_178518 | M-018245-00 |
| PL-50078 | C14 | X | −1.82 | −4.10 | W | FLJ38379 | 285097 | NM_178530 | M-017660-00 |
| PL-50072 | A13 | X | −2.47 | −1.83 | W | FLJ38984 | 127703 | NM_152374 | M-016893-00 |
| PL-50071 | H12 | X | −2.59 | −2.77 | W | FLJ39117 | 126638 | XM_371312 | M-027449-00 |
| PL-50072 | A04 | X | −2.25 | −2.87 | W | FLJ39155 | 133584 | NM_152403 | M-019235-00 |
| PL-50072 | C21 | X | −2.26 | −2.24 | W | FLJ40160 | 128620 | NM_173484 | M-018431-00 |
| PL-50081 | A23 | X | −2.01 | −1.94 | W | FLJ42953 | 400892 | NM_207474 | M-032163-00 |
| PL-50080 | F18 | X | −3.91 | −2.00 | W | FLJ42957 | 400077 | NM_207436 | M-032113-00 |
| PL-50080 | P17 | X | −1.88 | −2.66 | W | FLJ43965 | 389206 | NM_207406 | M-032079-00 |
| PL-50080 | H12 | X | −2.85 | −2.57 | W | FLJ45803 | 399948 | NM_207429 | M-032104-00 |
| PL-50080 | O14 | X | −2.09 | −2.75 | W | FLJ46354 | 374977 | NM_198547 | M-027321-00 |
| PL-50080 | P11 | X | −1.43 | −2.78 | W | FLJ46481 | 389197 | NM_207405 | M-032082-00 |
| PL-50008 | P08 | X | −2.71 | −3.35 | W | FOXB1 | 27023 | NM_012182 | M-008906-00 |
| PL-50008 | L04 | X | −4.33 | −1.87 | W | FOXP2 | 93986 | NM_014491 | M-010359-01 |
| PL-50070 | I11 | X | −2.12 | −2.27 | W | FOXP4 | 116113 | NM_138457 | M-008255-00 |
| PL-50048 | G11 | X | −2.21 | −2.52 | W | FSHPRH1 | 2491 | NM_006733 | M-005268-00 |
| PL-50006 | J23 | X | −2.04 | −2.38 | W | FTH1 | 2495 | NM_002032 | M-019634-01 |
| PL-50057 | A13 | X | −2.11 | −2.61 | W | FXC1 | 26515 | NM_012192 | M-018242-00 |
| PL-50001 | H18 | X | −3.04 | −1.84 | W | FYN | 2534 | NM_002037 | M-003140-03 |
| PL-50018 | M05 | X | −2.18 | −1.95 | W | GABRB1 | 2560 | NM_000812 | M-006168-00 |
| PL-50011 | A05 | X | −2.25 | −3.32 | W | GART | 2618 | NM_000819 | M-008594-00 |
| PL-50013 | A23 | X | −2.25 | −2.53 | W | GBP1 | 2633 | NM_002053 | M-005153-01 |
| PL-50017 | M08 | X | −3.40 | −1.34 | W | GDNF | 2668 | NM_000514 | M-011040-00 |
| PL-50019 | J09 | X | −3.26 | −2.11 | W | GJB3 | 2707 | NM_024009 | M-019948-00 |
| PL-50062 | I16 | X | −1.91 | −2.17 | W | GL004 | 56947 | NM_020194 | M-018261-00 |
| PL-50001 | F18 | X | −2.66 | −1.52 | W | GMFG | 9535 | NM_004877 | M-019878-01 |
| PL-50004 | A18 | X | −2.43 | −2.90 | W | GNAQ | 2776 | NM_002072 | M-008562-00 |
| PL-50061 | N08 | X | −2.11 | −2.21 | W | GOLGA6 | 55889 | NM_018652 | M-013307-00 |
| PL-50064 | O08 | X | −3.58 | −2.42 | W | GORASP1 | 64689 | NM_031899 | M-013510-00 |
| PL-50048 | O17 | X | −2.13 | −2.49 | W | GOT1 | 2805 | NM_002079 | M-011673-00 |
| PL-50057 | K20 | X | −2.15 | −1.58 | W | GPKOW | 27238 | NM_015698 | M-015129-00 |
| PL-50048 | O16 | X | −2.42 | −1.85 | W | GPM6B | 2824 | NM_005278 | M-018825-00 |
| PL-50004 | D11 | X | −2.86 | −2.53 | W | GPR101 | 83550 | NM_054021 | M-005526-01 |
| PL-50015 | N19 | X | −3.90 | −2.32 | W | GPR114 | 221188.00 | NM_153837 | M-005535-01 |
| PL-50004 | P05 | X | −2.10 | −1.83 | W | GPR50 | 9248 | NM_004224 | M-005578-00 |
| PL-50004 | P15 | X | −3.01 | −2.29 | W | GPR56 | 9289 | NM_005682 | M-004552-00 |
| PL-50004 | PO4 | X | −2.32 | −2.27 | W | GPR73L1 | 128674 | NM_144733 | M-005594-01 |
| PL-50016 | I16 | X | −2.60 | −1.70 | W | GRB7 | 2886.00 | NM_005310 | M-012701-00 |
| PL-50048 | O04 | X | −2.74 | −1.34 | W | GRID1 | 2894 | XM_043613 | M-007917-00 |
| PL-50016 | I06 | X | −2.41 | −2.33 | W | GRID2 | 2895.00 | NM_001510 | M-006188-00 |

TABLE 1-continued

| Stock_ID | Row | Type | Z score_A | Z score_B | Screen + | Gene Symbol | Entrez Gene ID | Accession # | Catalog # |
|---|---|---|---|---|---|---|---|---|---|
| PL-50004 | J16 | X | −2.36 | −1.70 | W | GRK7 | 131890 | NM_139209 | M-004628-00 |
| PL-50052 | F07 | X | −2.09 | −1.79 | W | GTPBP1 | 9567 | NM_004286 | M-017321-00 |
| PL-50006 | P09 | X | −2.87 | −2.40 | W | H2AFZ | 3015 | NM_002106 | M-011683-01 |
| PL-50052 | F05 | X | −2.54 | −2.09 | W | H6PD | 9563 | NM_004285 | 'M-004692-00 |
| PL-50022 | G10 | X | −2.20 | −2.29 | W | HBE1 | 3046 | NM_005330 | M-012069-00 |
| PL-50053 | J16 | X | −2.96 | −1.83 | W | HBXIP | 10542 | NM_006402 | M-012269-00 |
| PL-50008 | F14 | X | −2.40 | −2.43 | W | HCFC1 | 3054 | NM_005334 | M-019953-00 |
| PL-50020 | G12 | X | −2.47 | −2.33 | W | HD | 3064 | NM_002111 | M-003737-00 |
| PL-50013 | C17 | X | −2.51 | −2.37 | W | HDAC3 | 8841 | NM_003883 | M-003496-00 |
| PL-50061 | G13 | X | −2.86 | −3.19 | W | HEMGN | 55363 | NM_018437 | M-021355-00 |
| PL-50073 | B02 | X | −2.57 | −1.95 | W | HERV-FRD | 405754 | NM_207582 | |
| PL-50048 | K06 | X | −2.94 | −3.13 | W | HIST1H1B | 3009 | NM_005322 | M-012049-00 |
| PL-50081 | O18 | X | −3.97 | −1.63 | W | HIST1H2AL | 8332 | NM_003511 | M-011434-00 |
| PL-50051 | L09 | X | −4.54 | −1.37 | W | HIST1H3B | 8358 | NM_003537 | M-006475-00 |
| PL-50051 | L11 | X | −3.15 | −2.10 | W | HIST1H4A | 8359 | NM_003538 | M-011456-00 |
| PL-50008 | B12 | X | −2.39 | −2.71 | W | HOXA7 | 3204 | NM_006896 | M-017573-00 |
| PL-50048 | A18 | X | −0.65 | −2.78 | W | HOXB8 | 3218 | NM_024016 | M-017527-00 |
| PL-50048 | A14 | X | −1.59 | −2.94 | W | HOXC8 | 3224 | NM_022658 | M-012995-00 |
| PL-50060 | O23 | X | −3.65 | −1.92 | W | HRASLS2 | 54979 | NM_017878 | M-020862-00 |
| PL-50056 | O23 | X | −2.46 | −2.58 | W | HS747E2A | 25770 | NM_015370 | M-020284-00 |
| PL-50062 | P14 | X | −2.63 | −2.55 | W | HSCARG | 57407 | NM_020677 | M-020759-00 |
| PL-50070 | D04 | X | −1.86 | −2.59 | W | HSPB9 | 94086 | NM_033194 | M-009005-00 |
| PL-50004 | F18 | X | −3.01 | −2.53 | W | HTR1A | 3350 | NM_000524 | M-005633-00 |
| PL-50001 | B04 | X | −5.47 | −2.28 | W | HUNK | 30811 | NM_014586 | M-004214-01 |
| PL-50051 | H06 | X | −0.80 | −3.81 | W | HYAL2 | 8692 | NM_003773 | M-013689-00 |
| PL-50048 | D21 | X | −1.83 | −2.41 | W | IDH3G | 3421 | NM_004135 | M-009361-00 |
| PL-50064 | A05 | X | −2.30 | −1.52 | W | IFRG15 | 64163 | NM_022347 | M-014044-00 |
| PL-50070 | L06 | X | −1.41 | −2.46 | W | IGSF8 | 93185 | NM_052868 | M-015148-00 |
| PL-50017 | C20 | X | −2.89 | −2.23 | W | IL1ORB | 3588 | NM_000628 | M-007926-01 |
| PL-50017 | C06 | X | −2.44 | −2.31 | W | IL15RA | 3601 | NM_002189 | M-007935-00 |
| PL-50017 | CO2 | X | −2.24 | −3.02 | W | IL17 | 3605 | NM_002190 | M-007937-00 |
| PL-50069 | F15 | X | −2.57 | −1.76 | W | IL17F | 112744 | NM_052872 | M-007942-00 |
| PL-50017 | B13 | X | −2.58 | −1.46 | W | IL1F9 | 56300 | NM_019618 | M-007959-00 |
| PL-50017 | B23 | X | −1.30 | −2.70 | W | IL1RL1 | 9173 | NM_003856 | M-007963-00 |
| PL-50017 | D11 | X | −3.96 | −2.20 | W | IL22 | 50616 | NM_020525 | M-007972-00 |
| PL-50004 | D08 | X | −2.78 | −1.96 | W | IL8RB | 3579 | NM_001557 | M-005647-00 |
| PL-50022 | F07 | X | −2.43 | −2.63 | W | INSIG1 | 3638 | NM_005542 | M-017880-01 |
| PL-50006 | H12 | X | −3.18 | −2.23 | W | INSM1 | 3642 | NM_002196 | M-006535-00 |
| PL-50051 | O18 | X | −1.70 | −2.66 | W | INTERSEX | 55588 | XM:290829 | M-023654-00 |
| PL-50009 | G21 | X | −2.37 | −3.10 | W | IRF7 | 3665 | NM_001572 | M-011810-01 |
| PL-50065 | A23 | X | −3.60 | −1.48 | W | IRX1 | 79192 | XM_380171 | |
| PL-50022 | H13 | X | −2.41 | −3.95 | W | ITSN2 | 50618 | NM_006277 | M-009841-00 |
| PL-50057 | B11 | X | −2.63 | −3.04 | W | JM1 | 28952 | NM_014008 | M-020554-00 |
| PL-50069 | M05 | X | −2.57 | −2.29 | W | JM11 | 90060 | NM_033626 | M-015130-00 |
| PL-50068 | P18 | X | −2.41 | −2.32 | W | JUB | 84962 | NM_198086 | M-021473-00 |
| PL-50014 | H15 | X | −2.07 | −1.96 | W | KALRN | 8997.00 | NM_003947 | M-010019-00 |
| PL-50061 | B06 | X | −2.43 | −2.45 | W | KBTBD7 | 84078 | NM_032138 | M-015708-00 |
| PL-50020 | I17 | X | −0.96 | −3.17 | W | KCNC4 | 3749 | NM_004978 | M-006223-01 |
| PL-50016 | Al2 | X | −2.71 | −2.63 | W | KCNH4 | 23415.00 | NM_012285 | M-006234-01 |
| PL-50004 | B20 | X | −2.62 | −1.67 | W | KCNJ3 | 3760 | NM_002239 | M-006248-00 |
| PL-50064 | J17 | X | −2.90 | −2.72 | W | KCTD14 | 65982 | NM_023930 | M-014252-00 |
| PL-50002 | E19 | X | −2.70 | −2.08 | W | KDR | 3791 | NM_002253 | M-003148-01 |
| PL-50052 | B04 | X | −2.94 | −2.64 | W | KEAP1 | 9817 | NM_012289 | M-012453-00 |
| PL-50013 | E19 | X | −2.38 | −2.39 | W | KIAA0217 | 23185 | XM_040265 | M-026388-00 |
| PL-50052 | B08 | X | −2.95 | −1.93 | W | KIAA0542 | 9814 | XM_038520 | M-024567-00 |
| PL-50055 | A07 | X | −2.32 | −2.25 | W | KIAA0980 | 22981 | NM_025176 | M-018162-00 |
| PL-50055 | N10 | X | −2.87 | −1.91 | W | KIAA1068 | 23386 | NM_015332 | M-014018-00 |
| PL-50062 | L04 | X | −2.17 | −1.97 | W | K1AA1189 | 57471 | XM_371576 | M-027986-00 |
| PL-50062 | LO2 | X | −3.14 | −2.74 | W | KIAA1194 | 57472 | NM_015455 | M-019101-00 |
| PL-50002 | G09 | X | −3.22 | −2.00 | W | KIAA1361 | 57551 | XM_290796 | M-004846-01 |
| PL-50063 | O18 | X | −2.09 | −2.19 | W | KIAA1549 | 57670 | XM_371956 | M-025462-00 |
| PL-50063 | O04 | X | −2.92 | −1.90 | W | KIAA1573 | 57685 | NM_020925 | M-014178-00 |
| PL-50075 | D05 | X | −1.73 | −2.14 | W | KIAA1987 | 170951 | XM_375298 | M-030681-00 |
| PL-50015 | P14 | X | −2.15 | −3.76 | W | K1F11 | 3832.00 | NM_004523 | M-003317-01 |
| PL-50048 | J21 | X | −3.22 | −2.12 | W | KIR2DL4 | 3805 | NM_002255 | M-018983-00 |
| PL-50069 | A02 | X | −2.13 | −2.22 | W | KRTAP9-4 | 85280 | NM_033191 | M-013676-00 |
| PL-50076 | L06 | X | −2.86 | −2.22 | W | LACE1 | 246269 | NM_145315 | M-008222-00 |
| PL-50013 | G09 | X | −3.29 | −2.26 | W | LAP3 | 51056 | NM_015907 | M-005923-03 |
| PL-50048 | P09 | X | −3.03 | −1.97 | W | LASP1 | 3927 | NM_006148 | M-010519-00 |
| PL-50089 | K04 | X | −1.63 | −2.44 | W | LCN10 | 414332 | NM_001001712 | M-032327-00 |
| PL-50064 | A17 | X | −2.69 | −1.83 | W | LEPRE1 | 64175 | NM_022356 | M-004271-00 |
| PL-50060 | P20 | X | −0.80 | −3.39 | W | LGI2 | 55203 | NM_018176 | M-017097-00 |
| PL-50002 | I23 | X | −2.41 | −2.59 | W | LIM | 10611 | NM_006457 | M-006930-00 |
| PL-50015 | O09 | X | −2.25 | −2.78 | W | LMO7 | 4008.00 | NM_005358 | M-019252-00 |
| PL-50002 | G21 | X | −1.85 | −2.25 | W | LMTK3 | 114783 | XM_055866 | M-005338-01 |
| PL-50076 | N21 | X | −2.84 | −1.85 | W | LNX2 | 222484 | NM_153371 | M-007164-00 |
| PL-50069 | P15 | X | −2.49 | −2.56 | W | LOC113828 | 113828 | NM_138435 | M-015492-00 |

TABLE 1-continued

| Stock_ID | Row | Type | Z score_A | Z score_B | Screen + | Gene Symbol | Entrez Gene ID | Accession # | Catalog # |
|---|---|---|---|---|---|---|---|---|---|
| PL-50070 | I05 | X | −2.29 | −3.17 | W | LOC116068 | 116068 | XM_371760 | M-024521-00 |
| PL-50071 | O16 | X | −2.62 | −2.28 | W | LOC120376 | 120376 | XM_071712 | M-026516-00 |
| PL-50071 | F07 | X | −1.59 | −3.04 | W | LOC124402 | 124402 | NM_145253 | M-015987-00 |
| PL-50071 | N23 | X | −2.21 | −2.15 | W | LOC125893 | 125893 | XM_064856 | M-023813-00 |
| PL-50071 | J04 | X | −2.12 | −2.12 | W | LOC126520 | 126520 | XM_059051 | M-023896-00 |
| PL-50072 | B11 | X | −2.71 | −2.54 | W | LOC134145 | 134145 | NM_199133 | M-024274-00 |
| PL-50073 | O11 | X | −2.34 | −2.31 | W | LOC144097 | 144097 | NM_138471 | |
| PL-50081 | J11 | X | −1.54 | −2.58 | W | LOC145414 | 0 | XM_085138 | M-021965-00 |
| PL-50073 | C20 | X | −1.77 | −2.26 | W | LOC146443 | 146443 | XM_378558 | |
| PL-50073 | A14 | X | −2.89 | −2.56 | W | LOC146713 | 146713 | XM_378712 | |
| PL-50081 | A20 | X | −2.17 | −2.43 | W | LOC149643 | 0 | XM_086616 | M-021537-00 |
| PL-50074 | O11 | X | −2.57 | −2.20 | W | LOC151484 | 151484 | XM_379159 | M-028022-00 |
| PL-50082 | F23 | X | −2.31 | −1.98 | W | LOC152877 | 0 | XM_094066 | M-024144-00 |
| PL-50074 | E06 | X | −2.75 | −2.53 | W | LOC153328 | 153328 | NM_145282 | M-007347-00 |
| PL-50074 | D11 | X | −2.07 | −1.79 | W | LOC154222 | 154222 | XM_379456 | M-028649-00 |
| PL-50083 | K09 | X | −2.24 | −2.33 | W | LOC154907 | 0 | XM_088072 | M-025440-00 |
| PL-50081 | C16 | X | −2.08 | −2.30 | W | LOC155036 | 155036 | XM_376722 | M-028875-00 |
| PL-50083 | A21 | X | −1.87 | −2.14 | W | LOC158796 | 0 | XM_088677 | M-025004-00 |
| PL-50074 | J08 | X | −2.30 | −2.90 | W | LOC159090 | 159090 | NM_145284 | M-016085-00 |
| PL-50075 | C11 | X | −2.52 | −2.87 | W | LOC162427 | 162427 | NM_178126 | M-018456-00 |
| PL-50075 | K13 | X | −1.93 | −4.79 | W | LOC163590 | 163590 | NM_145034 | M-016470-00 |
| PL-50082 | A17 | X | −2.23 | −1.70 | W | LOC200493 | 0 | XM_115715 | M-022826-00 |
| PL-50076 | E15 | X | −2.05 | −2.86 | W | LOC202051 | 202051 | XM_114430 | M-024410-00 |
| PL-50076 | M23 | X | −2.49 | −2.58 | W | LOC205251 | 205251 | NM_174925 | M-017831-00 |
| PL-50081 | N05 | X | −3.34 | −1.92 | W | LOC254897 | 0 | XM_170950 | M-022066-00 |
| PL-50077 | F13 | X | −2.72 | −1.86 | W | LOC283152 | 283152 | XM_378314 | |
| PL-50077 | D04 | X | −2.21 | −4.21 | W | LOC283989 | 283989 | NM_207346 | |
| PL-50078 | A11 | X | −2.08 | −3.17 | W | LOC284058 | 284058 | NM_015443 | M-031748-00 |
| PL-50078 | K13 | X | −2.09 | −2.15 | W | LOC284361 | 284361 | NM_175063 | M-018434-00 |
| PL-50078 | M13 | X | −1.80 | −2.88 | W | LOC284390 | 284390 | XM_371138 | M-031229-00 |
| PL-50078 | M04 | X | −2.89 | −1.65 | W | LOC284661 | 284661 | XM_378832 | M-027567-00 |
| PL-50078 | K08 | X | −2.34 | −1.86 | W | LOC284739 | 284739 | NM_207349 | M-031294-00 |
| PL-50078 | I02 | X | −2.15 | −2.35 | W | LOC284825 | 284825 | XM_375935 | M-031369-00 |
| PL-50078 | A12 | X | −1.94 | −3.54 | W | LOC285194 | 285194 | XM_379207 | M-028149-00 |
| PL-50082 | I14 | X | −3.00 | −2.75 | W | LOC285248 | 0 | XM_211816 | M-023664-00 |
| PL-50083' | G10 | X | −2.14 | −2.08 | W | LOC338734 | 0 | XM_290547 | M-026505-00 |
| PL-50083 | F05 | X | −2.20 | −2.58 | W | L0C338756 | 0 | XM_291989 | M-026922-00 |
| PL-50079 | B09 | X | −2.64 | −1.81 | W | LOC340109 | 340109 | XM_379322 | M-028502-00 |
| PL-50083 | I14 | X | −2.28 | −1.93 | W | LOC340843 | 0 | XM_291726 | M-026400-00 |
| PL-50083 | J05 | X | −2.17 | −2.03 | W | LOC341356 | 0 | XM_292023 | M-027076-00 |
| PL-50082 | P12 | X | −5.82 | −2.32 | W | LOC345651 | 0 | XM_293924 | M-024480-00 |
| PL-50080 | M14 | X | −4.93 | −2.81 | W | LOC375133 | 375133 | NM_199345 | M-032119-00 |
| PL-50080 | CO2 | X | −3.73 | −1.73 | W | LOC386597 | 386597 | XM_379073 | M-027974-00 |
| PL-50086 | B14 | X | −3.37 | −2.68 | W | LOC387784 | 0 | XM_373506 | M-029865-00 |
| PL-50086 | H08 | X | −1.81 | −2.55 | W | LOC387810 | 0 | XM_373513 | M-029805-00 |
| PL-50087 | K18 | X | −1.48 | −3.48 | W | LOC387825 | 0 | XM_370668 | |
| PL-50087 | O04 | X | −2.59 | −2.12 | W | LOC387845 | 0 | XM_370684 | |
| PL-50087 | G02 | X | −4.14 | −2.44 | W | LOC387914 | 0 | XM_370718 | |
| PL-50088 | C11 | X | −2.83 | −2.18 | W | LOC388298 | 0 | XM_370992 | |
| PL-50088 | K21 | X | −2.71 | −2.99 | W | LOC388432 | 0 | XM_371086 | |
| PL-50081 | C12 | X | −4.87 | −2.48 | W | LOC388585 | 0 | XM_371215 | M-007769-00 |
| PL-50083 | PO4 | X | −2.40 | −3.20 | W | LOC388697 | 0 | XM_373868 | M-027450-00 |
| PL-50084 | G20 | X | −3.63 | −2.37 | W | LOC389000 | 0 | XM_371534 | M-027916-00 |
| PL-50084 | A14 | X | −2.42 | −1.82 | W | LOC389067 | 0 | XM_374021 | M-028005-00 |
| PL-50084 | A10 | X | −2.39 | −2.59 | W | LOC389070 | 0 | XM_374022 | M-028009-00 |
| PL-50084 | H11 | X | −2.84 | −2.27 | W | LOC389102 | 0 | XM_371623 | M-028089-00 |
| PL-50084 | P13 | X | −2.00 | −2.17 | W | LOC389153 | 0 | XM_374053 | M-028171-00 |
| PL-50085 | A15 | X | −1.85 | −2.10 | W | LOC389273 | 0 | XM_374115 | M-028392-00 |
| PL-50085 | CO2 | X | −2.12 | −3.30 | W | LOC389370 | 0 | XM_374162 | M-028681-00 |
| PL-50085 | B05 | X | −2.03 | −1.53 | W | LOC389386 | 0 | XM_371818 | M-028707-00 |
| PL-50085 | K08 | X | −3.31 | −2.67 | W | LOC389416 | 0 | XM_371837 | M-028580-00 |
| PL-50085 | P10 | X | −1.46 | −2.24 | W | LOC389541 | 0 | XM_371939 | M-028918-00 |
| PL-50086 | C08 | X | −2.54 | −2.06 | W | LOC389727 | 0 | XM_372092 | M-029462-00 |
| PL-50086 | B05 | X | −2.30 | −2.18 | W | LOC389753 | 0 | XM_372112 | M-029491-00 |
| PL-50086 | H18 | X | −3.76 | −1.94 | W | LOC389950 | 0 | XM_372307 | M-029790-00 |
| PL-50087 | CO2 | X | −5.64 | −2.10 | W | LOC390377 | 0 | XM_372486 | |
| PL-50083 | P09 | X | −1.83 | −3.25 | W | LOC391059 | 0 | XM_372784 | M-02741900 |
| PL-50084 | G23 | X | −2.56 | −1.54 | W | LOC391209 | 0 | XM_372840 | M-027739-00 |
| PL-50085 | B20 | X | −3.51 | −1.79 | W | LOC392702 | 0 | XM_374730 | M-029081-00 |
| PL-50085 | B08 | X | −3.38 | −1.62 | W | LOC392726 | 0 | XM_374734 | M-029100-00 |
| PL-50086 | C17 | X | −1.42 | −3.60 | W | LOC392791 | 0 | XM_374752 | M-029140-00 |
| PL-50086 | L06 | X | −2.71 | −2.95 | W | LOC399786 | 0 | XM_378236 | M-029755-00 |
| PL-50087 | A09 | X | −2.48 | −2.14 | W | LOC399920 | 0 | XM_378300 | |
| PL-50087 | O14 | X | −3.77 | −2.10 | W | LOC400092 | 0 | XM_378398 | |
| PL-50088 | G13 | X | −2.71 | −2.21 | W | LOC400479 | 0 | XM_375282 | |
| PL-50088 | I19 | X | −2.45 | −2.29 | W | LOC400619 | 0 | XM_378703 | |
| PL-50083 | P15 | X | −1.94 | −3.99 | W | LOC400740 | 0 | XM_378840 | M-027426-00 |

TABLE 1-continued

| Stock_ID | Row | Type | Z score_A | Z score_B | Screen + | Gene Symbol | Entrez Gene ID | Accession # | Catalog # |
|---|---|---|---|---|---|---|---|---|---|
| PL-50084 | B06 | X | −1.60 | −2.62 | W | LOC401169 | 0 | XM_379306 | M-028377-00 |
| PL-50085 | A17 | X | −2.43 | −1.78 | W | LOC401175 | 0 | XM_379317 | M-028393-00 |
| PL-50085 | E18 | X | −2.43 | −1.56 | W | LOC401286 | 0 | XM_376555 | M-028648-00 |
| PL-50085 | J11 | X | −3.03 | −2.86 | W | LOC401314 | 0 | XM_376586 | M-028821-00 |
| PL-50085 | J13 | X | −2.58 | −2.50 | W | LOC401316 | 0 | XM_376587 | M-028825-00 |
| PL-50085 | J15 | X | −1.74 | −2.76 | W | LOC401317 | 0 | XM_379479 | M-028826-00 |
| PL-50085 | J19 | X | −2.77 | −1.28 | W | LOC401321 | 0 | XM_379483 | M-028830-00 |
| PL-50086 | A16 | X | −2.87 | −1.88 | W | LOC401518 | 0 | XM_379638 | M-029475-00 |
| PL-50086 | J05 | X | −2.03 | −3.09 | W | LOC401548 | 0 | XM_376902 | M-029584-00 |
| PL-50086 | J15 | X | −2.49 | −2.92 | W | LOC401552 | 0 | XM_379668 | M-029594-00 |
| PL-50084 | L20 | X | −3.16 | −2.65 | W | LOC402148 | 0 | XM_377818 | M-028220-00 |
| PL-50085 | J04 | X | −2.32 | −2.36 | W | LOC402477 | 0 | XM_379803 | M-029005-00 |
| PL-50085 | D18 | X | −3.23 | −2.03 | W | LOC402515 | 0 | XM_380112 | M-029067-00 |
| PL-50085 | D12 | X | −1.79 | −4.81 | W | LOC402521 | 0 | XM_379848 | M-029073-00 |
| PL-50085 | B14 | X | −1.49 | −2.07 | W | L0C402537 | 0 | XM_380120 | M-029089-00 |
| PL-50089 | O21 | X | −3.27 | −2.66 | W | L0C402556 | 0 | XM_379877 | M-031795-00 |
| PL-50090 | A07 | X | −2.47 | −1.86 | W | LOC402560 | 0 | XM_380127 | M-031802-00 |
| PL-50086 | A19 | X | −2.56 | −3.08 | W | LOC402586 | 0 | XM_380138 | M-029126-00 |
| PL-50086 | A21 | X | −2.25 | −2.69 | W | LOC402587 | 0 | XM_380139 | M-029127-00 |
| PL-50086 | E21 | X | −1.65 | −3.01 | W | LOC402625 | 0 | XM_379975 | M-029163-00 |
| PL-50085 | F04 | X | −2.78 | −2.23 | W | LOC402641 | 0 | XM_379995 | M-029057-00 |
| PL-50081 | M17 | X | −3.94 | −1.80 | W | LOC404785 | 404785 | NM_207513 | M-032197-00 |
| PL-50058 | M23 | X | −3.15 | −0.63 | W | LOC51054 | 51054 | NM_015899 | M-020941-00 |
| PL-50057 | A16 | X | −2.13 | −1.90 | W | LOC51066 | 51066 | NM_015931 | M-020960-00 |
| PL-50058 | P07 | X | −2.64 | −3.28 | W | LOC51333 | 51333 | NM_016643 | M-006990-00 |
| PL-50059 | K05 | X | −2.62 | −2.50 | W | LOC51693 | 51693 | NM_016209 | M-021254-00 |
| PL-50070 | P05 | X | −2.95 | −2.76 | W | LOC92689 | 92689 | NM_138389 | M-015552-00 |
| PL-50069 | B23 | X | −2.30 | −2.80 | W | LOC96597 | 96597 | XM_378655 | M-023053-00 |
| PL-50019 | G07 | X | −3.09 | −2.93 | W | LOR | 4014 | NM_000427 | M-011077-00 |
| PL-50048 | P16 | X | −3.33 | −1.23 | W | LPO | 4025 | NM_006151 | M-023219-00 |
| PL-50022 | F18 | X | −2.00 | −2.26 | W | LTBP3 | 4054 | NM_021070 | M-014144-00 |
| PL-50016 | D07 | X | −2.46 | −3.34 | W | LU | 4059.00 | NM_005581 | M-010608-00 |
| PL-50017 | PO4 | X | −1.87 | −2.52 | W | LY64 | 4064 | NM_005582 | M-020015-00 |
| PL-50007 | A15 | X | −228 | −2.10 | W | M96 | 22823 | NM_007358 | M-012796-00 |
| PL-50022 | D16 | X | −2.13 | −1.89 | W | MAD2L2 | 10459 | NM_006341 | M-003272-03 |
| PL-50059 | H23 | X | −2.81 | −2.75 | W | MAGEL2 | 54551 | NM_019066 | M-013374-00 |
| PL-50002 | M10 | X | −1.81 | −2.45 | W | MAPK13 | 5603 | NM_002754 | M-003591-02 |
| PL-50007 | C09 | X | −1.94 | −2.22 | W | MAPRE2 | 10982 | NM_014268 | M-012501-00 |
| PL-50049 | B16 | X | −2.58 | −2.31 | W | MASP1 | 5648 | NM_001879 | M-005937-00 |
| PL-50013 | I15 | X | −2.56 | −2.75 | W | MBTPS2 | 51360 | NM_015884 | M-005940-01 |
| PL-50005 | C07 | X | −2.90 | −2.51 | W | MC4R | 4160 | NM_005912 | M-005660-00 |
| PL-50016 | D17 | X | −2.17 | −2.39 | W | MCC | 4163.00 | NM_002387 | M-010523-01 |
| PL-50053 | N17 | X | −2.20 | −2.76 | W | MCRS1 | 10445 | NM_006337 | M-018557-00 |
| PL-50022 | B06 | X | −2.01 | −3.85 | W | MDGA1 | 266727 | NM_153487 | M-016082-00 |
| PL-50072 | M14 | X | −1.50 | −3.11 | W | MDH1B | 130752 | XM_059468 | M-023122-00 |
| PL-50009 | O11 | X | −2.86 | −2.47 | W | MEF2A | 4205 | NM_005587 | M-009362-00 |
| PL-50009 | O13 | X | −1.72 | −2.04 | W | MEF2B | 4207 | 'NM_005919 | M-009342-00 |
| PL-50068 | C08 | X | −2.94 | −2.77 | W | MGC13168 | 84821 | NM_032735 | M-014977-00 |
| PL-50068 | N14 | X | −3.07 | −2.59 | W | MGC14126 | 84984 | NM_032898 | M-015039-00 |
| PL-50070 | P23 | X | −2.16 | −1.23 | W | MGC16372 | 92749 | NM_145038 | M-016558-00 |
| PL-50079 | O04 | X | −4.23 | −2.82 | W | MGC16597 | 339520 | XM_375500 | M-030964-00 |
| PL-50070 | KO2 | X | −2.66 | −1.94 | W | MGC17337 | 91283 | NM_080655 | M-015247-00 |
| PL-50081 | K21 | X | −2.40 | −2.20 | W | MGC21394 | 404203 | NM_205841 | M-031857-00 |
| PL-50074 | M16 | X | −2.23 | −2.69 | W | MGC23918 | 151903 | NM_144716 | M-015455-00 |
| PL-50072 | H08 | X | −2.51 | −3.29 | W | MGC23937 | 139596 | NM_145052 | M-016141-00 |
| PL-50005 | C13 | X | −2.91 | −2.23 | W | MGC26856 | 256710 | NM_152779 | M-016259-00 |
| PL-50074 | Al2 | X | −1.93 | −2.28 | W | MGC39633 | 153733 | NM_152549 | M-015448-00 |
| PL-50072 | L02 | X | −2.46 | −2.58 | W | MGC41945 | 138724 | NM_203299 | M-031891-00 |
| PL-50067 | J04 | X | −3.26 | −2.46 | W | MGC4238 | 84292 | NM_032332 | M-014860-00 |
| PL-50073 | D11 | X | −2.10 | −2.65 | W | MGC45714 | 147007 | NM_152464 | |
| PL-50076 | D04 | X | −1.77 | −2.91 | W | MGC50559 | 254013 | NM_173802 | M-018388-00 |
| PL-50080 | M06 | X | −1.69 | −2.85 | W | MGC52000 | 375260 | NM_198943 | M-031853-00 |
| PL-50063 | A09 | X | −3.04 | −2.88 | W | MICAL3 | 57553 | XM_032997 | M-024432-00 |
| PL-50063 | D21 | X | −4.46 | −2.44 | W | MIG12 | 58526 | NM_021242 | M-015884-00 |
| PL-50068 | F16 | X | −3.31 | −2.68 | W | MIRAB13 | 85377 | NM_033386 | M-015102-00 |
| PL-50014 | I19 | X | −2.67 | −3.05 | W | MMP24 | 10893.00 | NM_006690 | M-005963-01 |
| PL-50059 | K17 | X | −1.71 | −2.84 | W | M025 | 51719 | NM_016289 | M-015407-00 |
| PL-50054 | O16 | X | −2.84 | −2.14 | W | MORF4L1 | 10933 | NM_006791 | M-006379-00 |
| PL-50002 | E02 | X | −2.67 | −2.48 | W | MRC2 | 9902 | NM_006039 | M-020064-00 |
| PL-50059 | E21 | X | −1.55 | −2.18 | W | MRPL48 | 51642 | NM_016055 | M-017512-00 |
| PL-50059 | C10 | X | −1.16 | −3.52 | W | MRPS21 | 54460 | NM_018997 | M-013388-00 |
| PL-50007 | A04 | X | −3.23 | −1.63 | W | MT1A | 4489 | NM_005946 | M-012724-00 |
| PL-50071 | CO2 | X | −2.23 | −1.74 | W | MTFMT | 123263 | NM_139242 | M-009633-00 |
| PL-50013 | O21 | X | −3.05 | −2.44 | W | MTMR9 | 66036 | NM_015458 | M-019244-01 |
| PL-50010 | O05 | X | −3.21 | −2.46 | W | MTRF1L | 54516 | NM_019041 | M-015386-00 |
| PL-50007 | K07 | X | −1.21 | −2.88 | W | MYH1 | 4619 | NM_005963 | M-013486-00 |
| PL-50057 | N09 | X | −2.73 | −1.89 | W | MYLIP | 29116 | NM_013262 | M-006976-00 |

TABLE 1-continued

| Stock_ID | Row | Type | Z score_A | Z score_B | Screen + | Gene Symbol | Entrez Gene ID | Accession # | Catalog # |
|---|---|---|---|---|---|---|---|---|---|
| PL-50061 | J06 | X | −1.58 | −2.08 | W | MYO5C | 55930 | NM_018728 | M-031960-00 |
| PL-50051 | B13 | X | −3.48 | −1.64 | W | MYST3 | 7994 | NM_006766 | M-019849-00 |
| PL-50049 | E19 | X | −1.80 | −2.48 | W | NAP1L4 | 4676 | NM_005969 | M-012183-00 |
| PL-50051 | D06 | X | −0.40 | −2.39 | W | NAPG | 8774 | NM_003826 | M-011529-00 |
| PL-50011 | C16 | X | −2.28 | −2.15 | W | NCB5OR | 51167 | NM_016230 | M-009347-00 |
| PL-50049 | G07 | X | −3.23 | −2.49 | W | NCF4 | 4689 | NM_000631 | M-011128-00 |
| PL-50023 | B18 | X | −2.59 | −1.76 | W | NCOA5 | 57727 | NM_020967 | M-013157-00 |
| PL-50023 | B10 | X | −2.36 | −4.21 | W | NDEL1 | 81565 | NM_030808 | M-018571-00 |
| PL-50049 | K07 | X | −2.82 | −2.10 | W | NDUFB9 | 4715 | NM_005005 | M-019899-00 |
| PL-50049 | K11 | X | −2.38 | −2.61 | W | NDUFC1 | 4717 | NM_002494 | M-019601-00 |
| PL-50013 | B04 | X | −2.95 | −2.65 | W | NDUFS1 | 4719 | NM_005006 | M-019069-00 |
| PL-50049 | K19 | X | −1.20 | −3.23 | W | NDUFS6 | 4726 | NM_004553 | M-019817-00 |
| PL-50054 | K17 | X | −2.42 | −1.80 | W | NET-5 | 10867 | NM_006675 | M-012293-00 |
| PL-50072 | O07 | X | −2.53 | −2.48 | W | NEU4 | 129807 | NM_080741 | M-013263-00 |
| PL-50009 | I06 | X | −3.19 | −2.49 | W | NFATC2 | 4773 | NM_012340 | M-003606-01 |
| PL-50009 | E20 | X | −2.89 | −1.53 | W | NFKB2 | 4791 | NM_002502 | M-003918-00 |
| PL-50052 | G09 | X | −2.89 | −2.46 | W | NFS1 | 9054 | NM_021100 | M-011564-00 |
| PL-50049 | M17 | X | −3.01 | −2.15 | W | NHLH2 | 4808 | NM_005599 | M-020020-00 |
| PL-50063 | I16 | X | −2.01 | −2.62 | W | NOPE | 57722 | NM_020962 | M-014170-00 |
| PL-50051 | L08 | X | −2.19 | −2.30 | W | NPFF | 8620 | NM_003717 | M-011502-00 |
| PL-50005 | G09 | X | −2.39 | −2.05 | W | NPY2R | 4887 | NM_000910 | M-005673-01 |
| PL-50005 | G11 | X | −1.74 | −2.32 | W | NPY5R | 4889 | NM_006174 | M-005674-01 |
| PL-50054 | N13 | X | −1.63 | −2.71 | W | NRM | 11270 | NM_007243 | M-012779-00 |
| PL-50007 | O12 | X | −2.70 | −3.03 | W | NUCB1 | 4924 | NM_006184 | M-015822-00 |
| PL-50062 | D13 | X | −1.82 | −2.48 | W | NUP107 | 57122 | NM_020401 | M-020440-00 |
| PL-50061 | D21 | X | −2.28 | −1.73 | W | NUP133 | 55746 | NM_018230 | M-013322-00 |
| PL-50061 | H02 | X | −2.48 | −3.27 | W | NXF2 | 56001 | NM_017809 | M-010445-00 |
| PL-50061 | H06 | X | −1.54 | −3.06 | W | NXF5 | 55998 | NM_032946 | M-013599-00 |
| PL-50019 | P20 | X | −4.00 | −2.02 | W | NXT1 | 29107 | NM_013248 | M-017194-00 |
| PL-50069 | A23 | X | −1.88 | −2.00 | W | NYD-SP28 | 85478 | NM_033124 | M-015072-00 |
| PL-50023 | G16 | X | −2.24 | −3.32 | W | OFD1 | 8481 | NM_003611 | M-009300-01 |
| PL-50005 | G23 | X | −1.96 | −2.04 | W | OPN3 | 23596 | NM_014322 | M-005681-01 |
| PL-50089 | P07 | X | −1.47 | −2.83 | W | OR3A4 | 390756 | NM_001005334 | M-032453-00 |
| PL-50089 | L07 | X | −1.44 | −2.78 | W | OR4A5 | 81318 | NM_001005272 | M-032433-00 |
| PL-50089 | J20 | X | −2.50 | −2.48 | W | OR5B2 | 390190 | NM_001005566 | M-032494-00 |
| PL-50089 | L05 | X | −1.83 | −3.72 | W | OR5M11 | 219487 | NM_001005245 | M-032432-00 |
| PL-50089 | PO4 | X | −3.78 | −2.12 | W | OR6C74 | 254783 | NM_001005490 | M-032472-00 |
| PL-50056 | E19 | X | −2.02 | −1.91 | W | ORC3L | 23595 | NM_012381 | M-003285-01 |
| PL-50023 | E16 | X | −2.49 | −4.24 | W | OTOR | 56914 | NM_020157 | M-017390-00 |
| PL-50059 | K11 | X | −4.17 | −2.07 | W | PADI3 | 51702 | NM_016233 | M-021051-00 |
| PL-50069 | E06 | X | −1.66 | −2.78 | W | PAGE-5 | 90737 | NM_130467 | M-017468-00 |
| PL-50056 | L02 | X | −2.88 | −1.42 | W | PAI-RBP1 | 26135 | NM_015640 | M-020528-00 |
| PL-50060 | M10 | X | −3.27 | −1.51 | W | PAKIIP1 | 55003 | NM_017906 | M-020912-00 |
| PL-50076 | L05 | X | −2.26 | −1.72 | W | PAQR10 | 221938 | NM_198403 | M-008052-00 |
| PL-50009 | A18 | X | −3.07 | −2.42 | W | PAWR | 5074 | NM_002583 | M-004434-00 |
| PL-50049 | K02 | X | −3.58 | −2.13 | W | PCBP1 | 5093 | NM_006196 | M-012243-01 |
| PL-50062 | B07 | X | −3.19 | −2.38 | W | PCNP | 57092 | NM_020357 | M-020263-00 |
| PL-50007 | C20 | X | −2.34 | −1.95 | W | PCOLCE | 5118 | NM_002593 | M-011747-00 |
| PL-50023 | B07 | X | −2.40 | −2.28 | W | PDE6A | 5145 | NM_000440 | M-007651-00 |
| PL-50063 | B04 | X | −2.10 | −2.62 | W | PDF | 64146 | NM_022341 | M-003851-00 |
| PL-50011 | F21 | X | −2.31 | −1.75 | W | PDHA2 | 5161 | NM_005390 | M-023925-00 |
| PL-50016 | A19 | X | −2.67 | −2.94 | W | PDP2 | 57546.00 | NM_020786 | M-022572-00 |
| PL-50070 | L02 | X | −3.12 | −2.13 | W | PERLD1 | 93210 | NM_033419 | M-017912-00 |
| PL-50061 | E12 | X | −2.26 | −2.28 | W | PEX26 | 55670 | NM_017929 | M-019128-00 |
| PL-50002 | J23 | X | −2.09 | −2.44 | W | PFKFB3 | 5209 | NM_004566 | M-006763-00 |
| PL-50073 | N08 | X | −2.07 | −2.21 | W | PHF13 | 148479 | NM_153812 | |
| PL-50068 | C23 | X | −2.49 | −2.19 | W | PHYHIPL | 84457 | NM_032439 | M-014894-00 |
| PL-50078 | A23 | X | −2.16 | −2.00 | W | PIGW | 284098 | NM_178517 | M-021480-00 |
| PL-50002 | P07 | X | −1.58 | −3.31 | W | PIK3R3 | 8503 | NM_003629 | M-019546-00 |
| PL-50002 | P13 | X | −1.95 | −2.15 | W | PIK4CB | 5298 | NM_002651 | M-006777-02 |
| PL-50058 | H07 | X | −2.39 | −2.07 | W | PIPDX | 51268 | NM_016518 | M-010199-00 |
| PL-50075 | G16 | X | −2.79 | −2.75 | W | PKD1L1 | 168507 | NM_138295 | M-017434-00 |
| PL-50011 | L13 | X | −2.53 | −2.13 | W | PNLIP | 5406 | NM_000936 | M-008973-00 |
| PL-50011 | L15 | X | −2.42 | −2.27 | W | PNLIPRP1 | 5407 | NM_006229 | M-009145-00 |
| PL-50014 | G05 | X | −3.24 | −2.84 | W | PRDX3 | 10935.00 | NM_006793 | M-010355-00 |
| PL-50002 | L20 | X | −1.82 | −2.35 | W | PRKACA | 5566 | NM_002730 | M-004649-00 |
| PL-50018 | J11 | X | −2.05 | −1.97 | W | PROK1 | 84432 | NM_032414 | M-014883-00 |
| PL-50057 | A18 | X | −1.87 | −3.54 | W | PROL5 | 26952 | NM_012390 | M-020197-00 |
| PL-50002 | K13 | X | −2.45 | −1.79 | W | PRPS1L1 | 221823 | NM_175886 | M-006804-00 |
| PL-50050 | A09 | X | −2.02 | −3.81 | W | PSG3 | 5671 | NM_021016 | M-014137-00 |
| PL-50057 | P15 | X | −0.93 | −2.95 | W | PTD004 | 29789 | NM_013341 | M-015680-00 |
| PL-50058 | J11 | X | −2.32 | −2.24 | W | PTX1 | 51290 | NM_016570 | M-021151-00 |
| PL-50056 | G19 | X | −2.66 | −3.04 | W | RABGAP1 | 23637 | NM_012197 | M-012803-00 |
| PL-50013 | D11 | X | −2.20 | −1.93 | W | RABL2A | 11159 | NM_007082 | M-013620-00 |
| PL-50013 | F11 | X | −2.65 | −3.09 | W | RANBP2 | 5903 | NM_006267 | M-004746-01 |
| PL-50056 | A09 | X | −2.52 | −1.67 | W | RASD2 | 23551 | NM_014310 | M-009560-00 |
| PL-50070 | E02 | X | −1.96 | −2.22 | W | RASL1OB | 91608 | NM_033315 | M-008344-00 |

TABLE 1-continued

| Stock_ID | Row | Type | Z score_A | Z score_B | Screen + | Gene Symbol | Entrez Gene ID | Accession # | Catalog # |
|---|---|---|---|---|---|---|---|---|---|
| PL-50059 | E06 | X | −2.00 | −2.83 | W | RBM27 | 54439 | XM_291128 | M-024337-00 |
| PL-50007 | J19 | X | −2.21 | −2.60 | W | RBM5 | 10181 | NM_005778 | M-009220-01 |
| PL-50011 | P10 | X | −2.94 | −2.47 | W | RCE1 | 9986 | NM_005133 | M-006025-00 |
| PL-50073 | O02 | X | −2.85 | −1.93 | W | RDH12 | 145226 | NM_152443 | |
| PL-50011 | P08 | X | −2.92 | −1.42 | W | RDH5 | 5959 | NM_002905 | M-008220-01 |
| PL-50057 | P18 | X | −1.73 | −2.54 | W | REPIN1 | 29803 | NM_013400 | M-006978-00 |
| PL-50054 | C09 | X | −2.31 | −2.46 | W | RFPL3 | 10738 | NM_006604 | M-006934-00 |
| PL-50054 | P10 | X | −1.95 | −2.06 | W | RNF13 | 11342 | NM_007282 | M-006944-00 |
| PL-50018 | D17 | X | −2.24 | −2.52 | W | RORB | 6096 | NM_006914 | M-003441-01 |
| PL-50080 | K20 | X | −1.57 | −2.35 | W | RP26 | 375298 | NM_201548 | M-027336-00 |
| PL-50074 | D21 | X | −2.03 | −2.89 | W | RPIB9 | 154661 | NM_138290 | M-015403-00 |
| PL-50050 | O09 | X | −3.26 | −1.86 | W | RPL3L | 6123 | NM_005061 | M-012009-00 |
| PL-50003 | C19 | X | −2.44 | −1.89 | W | RPS6KA2 | 6196 | NM_021135 | M-004663-01 |
| PL-50005 | C20 | X | −2.04 | −3.11 | W | RRH | 10692 | NM_006583 | M-005723-01 |
| PL-50050 | E08 | X | −1.85 | −4.78 | W | SAA2 | 6289 | NM_030754 | M-016279-00 |
| PL-50005 | C18 | X | −2.99 | −2.50 | W | SALPR | 51289 | NM_016568 | M-004774-00 |
| PL-50050 | C18 | X | −2.18 | −2.16 | W | SATB1 | 6304 | NM_002971 | M-011771-00 |
| PL-50007 | P16 | X | −2.75 | −1.65 | W | SCA7 | 6314 | NM_000333 | M-011106-00 |
| PL-50016 | N15 | X | −2.88 | −1.93 | W | SCG3 | 29106.00 | NM_013243 | M-013710-00 |
| PL-50007 | N20 | X | −2.05 | −2.03 | W | SEC22L1 | 9554 | NM_004892 | M-011963-00 |
| PL-50064 | NO2 | X | −2.81 | −2.48 | W | SECISBP2 | 79048 | NM_024077 | M-015634-00 |
| PL-50011 | L20 | X | −2.73 | −2.88 | W | SENP1 | 29843 | NM_014554 | M-006357-00 |
| PL-50062 | P17 | X | −1.38 | −2.19 | W | SENP7 | 57337 | NM_020654 | M-006035-00 |
| PL-50071 | C04 | X | −2.84 | −1.66 | W | SENP8 | 123228 | NM_145204 | M-004071-00 |
| PL-50055 | B08 | X | −1.54 | −2.91 | W | SEZ6L | 23544 | NM_021115 | M-008081-00 |
| PL-50063 | G20 | X | −3.18 | −2.00 | W | SF4 | 57794 | NM_172231 | M-017511-00 |
| PL-50007 | L12 | X | −2.30 | −2.29 | W | SFRS7 | 6432 | NM_006276 | M-015909-00 |
| PL-50062 | G16 | X | −1.99 | −3.46 | W | SHD | 56961 | NM_020209 | M-023905-00 |
| PL-50016 | P12 | X | −2.04 | −2.07 | W | SLAMF6 | 114836.00 | NM_052931 | M-013423-01 |
| PL-50062 | C18 | X | −2.38 | −1.44 | W | SLC12A9 | 56996 | NM_020246 | M-007390-00 |
| PL-50049 | M08 | X | −3.20 | −1.97 | W | SLC22A1LS | 5003 | NM_007105 | M-019642-00 |
| PL-50064 | J04 | X | −2.51 | −2.24 | W | SLC25A23 | 79085 | NM_024103 | M-007360-00 |
| PL-50076 | O17 | X | −2.62 | −2.27 | W | SLC36A1 | 206358 | NM_078483 | M-007550-00 |
| PL-50054 | L23 | X | −2.77 | −2.46 | W | SLC6A14 | 11254 | NM_007231 | M-007601-00 |
| PL-50019 | H08 | X | −2.11 | −1.95 | W | SLC6A2 | 6530 | NM_001043 | M-007602-00 |
| PL-50019 | H06 | X | −2.68 | −2.10 | W | SLC6A4 | 6532 | NM_001045 | M-007604-00 |
| PL-50003 | G19 | X | −1.94 | −2.19 | W | SMG1 | 23049 | NM_014006 | M-005033-00 |
| PL-50063 | D20 | X | −2.37 | −2.17 | W | SMOC2 | 64094 | NM_022138 | M-013886-00 |
| PL-50051 | D08 | X | −0.53 | −2.93 | W | SNAP23 | 8773 | NM_003825 | M-017545-00 |
| PL-50066 | N08 | X | −2.00 | −3.51 | W | SNX27 | 81609 | NM_030918 | M-017346-00 |
| PL-50009 | P21 | X | −2.18 | −2.36 | W | SP4 | 6671 | NM_003112 | M-006562-00 |
| PL-50057 | I08 | X | −2.55 | −1.44 | W | SPINK4 | 27290 | NM_014471 | M-020235-00 |
| PL-50050 | N12 | X | −2.03 | −2.92 | W | SPINT1 | 6692 | NM_003710 | M-004578-00 |
| PL-50055 | P09 | X | −2.01 | −2.06 | W | SR140 | 23350 | XM_031553 | M-023607-00 |
| PL-50050 | J16 | X | −1.80 | −3.15 | W | SSA2 | 6738 | NM_004600 | M-017733-00 |
| PL-50005 | C04 | X | −2.07 | −3.32 | W | SSTR2 | 6752 | NM_001050 | M-005728-01 |
| PL-50005 | A20 | X | −2.44 | −2.38 | W | SSTR4 | 6754 | NM_001052 | M-005730-02 |
| PL-50009 | P10 | X | −2.02 | −2.97 | W | SSX1 | 6756 | NM_005635 | M-019194-00 |
| PL-50439 | E21 | X | −2.83 | −2.58 | W | STAMBPLI | 57559 | NM_020799 | M-005783-01 |
| PL-50057 | E15 | X | −2.76 | −2.12 | W | STEAP | 26872 | NM_012449 | M-003713-00 |
| PL-50052 | G04 | X | −3.23 | −2.14 | W | STOML1 | 9399 | NM_004809 | M-009360-00 |
| PL-50058 | A05 | X | −1.40 | −2.62 | W | STOML2 | 30968 | NM_013442 | M-020518-00 |
| PL-50057 | M06 | X | −3.18 | −1.68 | W | SULT1C2 | 27233 | NM_006588 | M-010391-00 |
| PL-50050 | P19 | X | −2.48 | −1.21 | W | SUMO2 | 6613 | NM_006937 | M-016450-00 |
| PL-50050 | F02 | X | −2.15 | −2.47 | W | SYCP1 | 6847 | NM_003176 | M-019171-00 |
| PL-50007 | F02 | X | −1.95 | −2.02 | W | SYNCRIP | 10492 | NM_006372 | M-016218-00 |
| PL-50055 | A16 | X | −1.90 | −2.68 | W | SYNE2 | 23224 | NM_015180 | M-019259-00 |
| PL-50069 | B05 | X | −1.91 | −2.45 | W | SYTL4 | 94121 | NM_080737 | M-007111-00 |
| PL-50077 | G16 | X | −2.35 | −4.18 | W | TAB3 | 257397 | NM_152787 | |
| PL-50077 | E08 | X | −1.65 | −2.60 | W | TAS2R45 | 259291 | NM_176886 | |
| PL-50012 | G18 | X | −3.34 | −2.54 | W | TBCC | 6903 | NM_003192 | M-011401-00 |
| PL-50003 | O04 | X | −2.57 | −2.29 | W | TESK2 | 10420 | NM_007170 | M-005044-00 |
| PL-50062 | A07 | X | −3.15 | −2.06 | W | TEX13B | 56156 | NM_031273 | M-013485-00 |
| PL-50009 | B20 | X | −2.23 | −2.23 | W | TGIF2LY | 90627 | NM_139214 | M-017279-00 |
| PL-50050 | B02 | X | −1.78 | −2.85 | W | TGM3 | 7053 | NM_003245 | M-010088-00 |
| PL-50007 | B06 | X | −2.51 | −2.28 | W | TIMELESS | 8914 | NM_003920 | M-019488-00 |
| PL-50058 | F14 | X | −2.28 | −2.99 | W | TMEM14C | 51522 | NM_016462 | M-020269-00 |
| PL-50070 | C21 | X | −2.29 | −2.46 | W | TNFRSF13C | 115650 | NM_052945 | M-013424-00 |
| PL-50018 | A19 | X | −2.73 | −1.44 | W | TNFSFI3B | 10673 | NM_006573 | M-017586-00 |
| PL-50068 | B04 | X | −2.26 | −2.71 | W | TNKSIBPI | 85456 | NM_033396 | M-015106-00 |
| PL-50008 | A15 | X | −3.66 | −2.06 | W | TNXB | 7148 | NM_019105 | M-008106-00 |
| PL-50018 | C19 | X | −2.25 | −2.22 | W | TOLLIP | 54472 | NM_019009 | M-016930-00 |
| PL-50064 | I10 | X | −2.96 | −2.82 | W | TORC3 | 64784 | NM_022769 | M-014210-00 |
| PL-50015 | O08 | X | −2.51 | −1.97 | W | TRIM22 | 10346.00 | NM_006074 | M-006927-01 |
| PL-50015 | F23 | X | −2.38 | −2.30 | W | TRIM33 | 51592.00 | NM_015906 | M-005392-02 |
| PL-50053 | I20 | X | −2.24 | −3.53 | W | TSPAN-1 | 10103 | NM_005727 | M-003719-00 |
| PL-50012 | J09 | X | −2.74 | −1.51 | W | TULP1 | 7287 | NM_003322 | M-011413-00 |

TABLE 1-continued

| Stock_ID | Row | Type | Z score_A | Z score_B | Screen + | Gene Symbol | Entrez Gene ID | Accession # | Catalog # |
|---|---|---|---|---|---|---|---|---|---|
| PL-50062 | C20 | X | −2.31 | −2.28 | W | TULP4 | 56995 | NM_020245 | M-013785-00 |
| PL-50066 | N17 | X | −2.02 | −2.71 | W | TXNDC | 81542 | NM_030755 | M-010675-00 |
| PL-50012 | J17 | X | −2.09 | −2.45 | W | TYMS | 7298 | NM_001071 | M-004717-01 |
| PL-50050 | N20 | X | −4.03 | −1.70 | W | UAP1 | 6675 | NM_003115 | M-017160-00 |
| PL-50012 | L13 | X | −2.86 | −2.62 | W | UBE2L6 | 9246 | NM_004223 | M-008569-00 |
| PL-50058 | B08 | X | −1.72 | −2.24 | W | UFM1 | 51569 | NM_016617 | M-021005-00 |
| PL-50071 | B19 | X | −1.54 | −2.68 | W | UNQ2446 | 123904 | NM_198443 | M-027207-00 |
| PL-50080 | C20 | X | −4.44 | −2.16 | W | UNQ2492 | 377841 | NM_198585 | M-027275-00 |
| PL-50078 | M23 | X | −2.63 | −1.54 | W | UNQ3033 | 284415 | NM_198481 | M-027236-00 |
| PL-50080 | D14 | X | −2.57 | −2.61 | W | UNQ9370 | 400454 | NM_207447 | M-032131-00 |
| PL-50064 | F15 | X | −2.44 | −2.66 | W | UPF3B | 65109 | NM_023010 | M-012871-00 |
| PL-50070 | M13 | X | −2.79 | −1.27 | W | VEST1 | 116328 | NM_052958 | M-015175-00 |
| PL-50076 | N14 | X | −2.58 | −2.97 | W | VGLL2 | 245806 | NM_153453 | M-015963-00 |
| PL-50005 | H07 | X | −2.62 | −3.09 | W | VN1R4 | 317703 | NM_173857 | M-017651-00 |
| PL-50019 | F05 | X | −2.18 | −2.02 | W | VPS13A | 23230 | NM_015186 | M-012878-00 |
| PL-50061 | B02 | X | −2.23 | −1.62 | W | VPS35 | 55737 | NM_018206 | M-010894-00 |
| PL-50064 | C18 | X | −2.66 | −2.10 | W | WARP | 64856 | NM_022834 | M-016331-00 |
| PL-50072 | B08 | X | −2.36 | −2.10 | W | WFDC3 | 140686 | NM_181522 | M-013334-00 |
| PL-50016 | F06 | X | −3.36 | −4.06 | W | WNT7B | 7477.00 | NM_058238 | M-003722-02 |
| PL-50063 | B10 | X | −3.24 | −2.28 | W | XYLT2 | 64132 | NM_022167 | M-013040-00 |
| PL-50003 | E06 | X | −3.18 | −2.63 | W | ZAK | 51776 | NM_133646 | M-005068-00 |
| PL-50063 | K05 | X | −1.49 | −2.73 | W | ZBTB2 | 57621 | NM_020861 | M-014129-00 |
| PL-50021 | B08 | X | −2.06 | −2.17 | W | ZBTB7 | 51341 | NM_015898 | M-020818-00 |
| PL-500610 | O10 | X | −1.65 | −2.48 | W | ZCCHC8 | 55596 | NM_017612 | M-021026-00 |
| PL-50072 | B18 | X | −1.71 | −2.12 | W | ZFP28 | 140612 | NM_020828 | M-014089-00 |
| PL-50010 | C23 | X | −2.43 | −2.86 | W | ZFP67 | 51043 | NM_015872 | M-020934-00 |
| PL-50059 | G23 | X | −2.13 | −1.92 | W | ZFR | 51663 | NM_016107 | M-019266-00 |
| PL-50051 | I10 | X | −1.86 | −4.52 | W | ZNF192 | 7745 | NM_006298 | M-020154-00 |
| PL-50058 | A11 | X | −2.88 | −2.74 | W | ZNF295 | 49854 | NM_020727 | M-013945-00 |
| PL-50055 | M17 | X | −2.52 | −1.51 | W | ZNF297B | 23099 | NM_014007 | M-020320-00 |
| PL-50062 | P19 | X | −3.24 | −2.42 | W | ZNF304 | 57343 | NM_020657 | M-020719-00 |
| PL-50056 | M18 | X | −2.34 | −2.31 | W | ZNF324 | 25799 | NM_014347 | M-006964-00 |
| PL-50061 | B09 | X | −1.88 | −2.35 | W | ZNF334 | 55713 | NM_018102 | M-017955-00 |
| PL-50057 | D02 | X | −2.35 | −2.62 | W | ZNF354C | 30832 | NM_014594 | M-014199-00 |
| PL-50068 | A18 | X | −2.28 | −2.49 | W | ZNF496 | 84838 | NM_032752 | M-014983-00 |
| PL-50070 | C15 | X | −2.56 | −3.03 | W | ZNF501 | 115560 | NM_145044 | M-007118-00 |
| PL-50068 | B07 | X | −3.37 | −2.84 | W | ZNF503 | 84858 | NM_032772 | M-015846-00 |
| PL-50057 | G12 | X | −1.43 | −2.54 | W | ZNF544 | 27300 | NM_014480 | M-020223-00 |
| PL-50073 | P08 | X | −2.79 | −2.65 | W | ZNF570 | 148268 | NM_144694 | |
| PL-50078 | K23 | X | −2.22 | −1.70 | W | ZNF615 | 284370 | NM_198480 | M-032239-00 |
| PL-50057 | B18 | X | −1.29 | −5.41 | W | ZNRD1 | 30834 | NM_014596 | M-017359-00 |
| PL-50001 | A05 | X | 2.49 | 1.61 | *W | AAK1 | 22848 | NM_014911 | M-005300-00 |
| PL-50001 | F04 | X | 2.28 | 2.34 | *W | GSK3A | 2931 | NM_019884 | M-003009-01 |
| PL-50004 | I14 | X | 2.20 | 1.88 | *W | FLJ10060 | 55065 | NM_017986 | M-010712-00 |
| PL-50005 | B15 | X | 2.18 | 2.38 | *W | TAS2R16 | 50833 | NM_016945 | M-013103-00 |
| PL-50005 | F21 | X | 2.02 | 2.31 | *W | VN1R1 | 57191 | NM_020633 | M-013177-00 |
| PL-50008 | A12 | X | 2.19 | 1.82 | *W | BHLHB2 | 8553 | NM_003670 | M-010318-00 |
| PL-50010 | A12 | X | 2.15 | 1.98 | *W | B4GALT7 | 11285 | NM_007255 | M-012387-00 |
| PL-50010 | J15 | X | 2.19 | 2.10 | *W | CTPS | 1503 | NM_001905 | M-006644-00 |
| PL-50013 | F18 | X | 2.13 | 1.81 | *W | ATP2A3 | 489 | NM_005173 | M-006114-01 |
| PL-50016 | A10 | X | 2.61 | 2.25 | *W | KCNH7 | 90134.00 | NM_033272 | M-006237-01 |
| PL-50016 | J16 | X | 2.24 | 1.89 | *W | TRADD | 8717.00 | NM_003789 | M-004452-00 |
| PL-50019 | M11 | X | 2.37 | 2.46 | *W | CDC10 | 989 | NM_001788 | M-011607-00 |
| PL-50019 | I08 | X | 2.22 | 2.02 | *W | PKP1 | 5317 | NM_000299 | M-012545-00 |
| PL-50019 | G10 | X | 2.30 | 1.86 | *W | RPS5 | 6193 | NM_001009 | M-010498-01 |
| PL-50019 | L06 | X | 2.05 | 1.96 | *W | SLC22Al2 | 116085 | NM_144585 | M-007446-01 |
| PL-50020 | C14 | X | 1.95 | 2.54 | *W | ACYP1 | 97 | XM_352906 | M-009937-00 |
| PL-50020 | L12 | X | 2.05 | 1.76 | *W | BOL2L1 | 598 | NM_138578 | M-003458-00 |
| PL-50020 | C05 | X | 2.29 | 1.14 | *W | CACNA1D | 776 | NM_000720 | M-006124-01 |
| PL-50021 | G12 | X | 2.27 | 1.23 | *W | CYB5 | 1528 | NM_001914 | M-019621-00 |
| PL-50022 | G19 | X | 2.14 | 2.75 | *W | FLJ25952 | 253832 | NM_153251 | M-016758-00 |
| PL-50022 | K11 | X | 2.08 | 1.67 | *W | GAA | 2548 | NM_000152 | M-008881-00 |
| PL-50022 | K13 | X | 2.20 | 2.98 | *W | GAB3 | 139716 | NM_080612 | M-015239-00 |
| PL-50022 | M13 | X | 1.86 | 2.83 | *W | GATA6 | 2627 | NM_005257 | M-008351-01 |
| PL-50023 | E05 | X | 2.44 | 1.66 | *W | HNRPA1 | 3178 | NM_031157 | M-008221-01 |
| PL-50024 | G11 | X | 2.34 | 2.76 | *W | RPS16 | 6217 | NM_001020 | M-013627-00 |
| PL-50024 | N06 | X | 3.90 | 3.36 | *W | XPO1 | 7514 | NM_003400 | M-003030-01 |
| PL-50047 | D11 | X | 2.55 | 2.13 | *W | AP2M1 | 1173 | NM_004068 | M-008170-00 |
| PL-50047 | O13 | X | 3.41 | 2.59 | *W | ATP2B1 | 490 | NM_001682 | M-006115-00 |
| PL-50047 | B15 | X | 2.22 | 1.89 | *W | CEACAM3 | 1084 | NM_001815 | M-019510-00 |
| PL-50048 | P21 | X | 2.81 | 2.50 | *W | FADS3 | 3995 | NM_021727 | M-008483-00 |
| PL-50048 | K19 | X | 2.52 | 1.91 | *W | GGTL3 | 2686 | NM_052830 | M-005886-00 |
| PL-50048 | C10 | X | 2.29 | 2.46 | *W | HNRPL | 3191 | NM_001533 | M-011293-00 |
| PL-50049 | B11 | X | 2.20 | 2.20 | *W | POLR2I | 5438 | NM_006233 | M-012248-00 |
| PL-50050 | M10 | X | 2.37 | 2.17 | *W | RPL28 | 6158 | NM_000991 | M-011145-00 |
| PL-50050 | K08 | X | 2.01 | 1.96 | *W | RPLP2 | 6181 | NM_001004 | M-004314-00 |
| PL-50050 | I18 | X | 2.12 | 1.46 | *W | RPS3A | 6189 | NM_001006 | M-013603-00 |

TABLE 1-continued

| Stock_ID | Row | Type | Z score_A | Z score_B | Screen + | Gene Symbol | Entrez Gene ID | Accession # | Catalog # |
|---|---|---|---|---|---|---|---|---|---|
| PL-50053 | C13 | X | 2.35 | 2.10 | *W | PLEKHM1 | 9842 | NM_014798 | M-023203-00 |
| PL-50055 | B10 | X | 2.03 | 2.04 | *W | RBM9 | 23543 | NM_014309 | M-020616-00 |
| PL-50060 | N02 | X | 2.09 | 1.47 | *W | FLJ10774 | 55226 | NM_024662 | M-014402-00 |
| PL-50061 | B15 | X | 1.98 | 2.01 | *W | FLJ10534 | 55720 | NM_018128 | M-017111-00 |
| PL-50064 | B04 | X | 2.31 | 1.97 | *W | VIK | 79027 | NM_024061 | M-012894-00 |
| PL-50065 | I02 | X | 2.24 | 1.89 | *W | FLJ22222 | 79701 | NM_024648 | |
| PL-50065 | B16 | X | 2.69 | 1.76 | *W | POF1B | 79983 | NM_024921 | |
| PL-50066 | N10 | X | 1.71 | 2.25 | *W | FIP1L1 | 81608 | NM_030917 | M-014670-00 |
| PL-50066 | I11 | X | 2.35 | 1.19 | *W | FLJ22173 | 80111 | NM_025041 | M-014563-00 |
| PL-50066 | P07 | X | 2.55 | 2.66 | *W | STMN4 | 81551 | NM_030795 | M-016810-00 |
| PL-50066 | E04 | X | 2.46 | 1.37 | *W | ULBP1 | 80329 | NM_025218 | M-014611-00 |
| PL-50067 | H12 | X | 2.15 | 2.13 | *W | C6ORF125 | 84300 | NM_032340 | M-021290-00 |
| PL-50067 | C10 | X | 2.15 | 2.00 | *W | KFZP5640052 | 84060 | NM_032120 | M-014780-00 |
| PL-50068 | I14 | X | 2.06 | 1.83 | *W | KRTAP1-5 | 83895 | NM_031957 | M-013515-00 |
| PL-50069 | B09 | X | 2.16 | 2.15 | *W | ARHGAPI2 | 94134 | NM_018287 | M-008729-00 |
| PL-50073 | F08 | X | 2.07 | 2.01 | *W | FLJ33084 | 149483 | NM_152500 | |
| PL-50076 | O11 | X | 2.22 | 2.00 | *W | KIAA2018 | 205717 | XM_291062 | M-023709-00 |
| PL-50076 | I18 | X | 2.04 | 2.03 | *W | SPAS1 | 219938 | NM_174927 | M-017842-00 |
| PL-50076 | D09 | X | 1.68 | 2.01 | *W | TDRD6 | 221400 | XM_166443 | M-025108-00 |
| PL-50078 | A18 | X | 1.96 | 2.05 | *W | FLJ46536 | 285180 | NM_198483 | M-027237-00 |
| PL-50080 | G07 | X | 2.01 | 1.75 | *W | GLTDCI | 360203 | NM_182974 | M-019460-00 |
| PL-50083 | K07 | X | 1.90 | 2.53 | *W | LOC219612 | 0 | XM_168585 | M-025428-00 |
| PL-50085 | H09 | X | 2.13 | 1.86 | *W | LOC402280 | 0 | XM_377946 | M-028792-00 |
| PL-50085 | H10 | X | 1.79 | 2.08 | *W | LOC402489 | 0 | XM_379819 | M-029023-00 |
| PL-50086 | H15 | X | 2.05 | 2.08 | *W | LOC389777 | 0 | XM_374300 | M-029575-00 |
| PL-50086 | H20 | X | 2.17 | 2.28 | *W | LOC401638 | 0 | XM_377109 | M-029788-00 |
| PL-50088 | H17 | X | 1.43 | 2.56 | *W | LOC390937 | 0 | XM_372730 | |
| PL-50088 | H13 | X | 2.23 | 1.75 | *W | LOC401915 | 0 | XM_377529 | |
| PL-50439 | A09 | X | 1.74 | 2.27 | *W | COPS5 | 10987 | NM_006837 | M-005814-01 |
| PL-50439 | I21 | X | 2.55 | 2.65 | *W | UBE2J2 | 118424 | NM_058167 | M-008614-00 |
| PL-50439 | D19 | X | 2.18 | 2.60 | *W | USP35 | 57558 | XM_290527 | M-006083-01 |

TABLE 2

| GeneSymbol | EntrezGeneID | Genbank Acc. No. | NFAT Score |
|---|---|---|---|
| AB026190 | 27252 | NM_014458 | W |
| ABCC13 | 150000 | NM_138726 | M |
| ABLIM2 | 84448 | NM_032432 | W |
| ACLY | 47 | NM_001096 | W |
| ACTB | 60 | NM_001101 | M |
| ACY1L2 | 135293 | XM_072402 | W |
| ADAM10 | 102 | NM_001110 | M |
| ADAMTS5 | 11096 | NM_007038 | S |
| ADCY4 | 196883 | NM_139247 | W |
| ADK | 132 | NM_001123 | W |
| ADRA2B | 151 | NM_000682 | W |
| AFG3L1 | 172 | NM_001132 | M |
| AGK | 55750 | NM_018238 | W |
| AKAP11 | 11215 | NM_016248 | W |
| AKR1CL1 | 340811 | XM_291723 | W |
| AKR1CL2 | 83592 | NM_031436 | M |
| ALCAM | 214 | NM_001627 | M |
| ALS2CR13 | 150864 | NM_173511 | W |
| ALS2CR15 | 130026 | NM_138468 | M |
| AMH | 268 | NM_000479 | W |
| AMIGO2 | 347902 | NM_181847 | W |
| ANC_2H01 | 51193 | NM_016331 | M |
| ANKFX1 | 51479 | NM_016376 | W |
| ANKK1 | 255239 | NM_178510 | W |
| ANKMX2 | 57037 | NM_020319 | W |
| ANKRD9 | 122416 | NM_152326 | M |
| AP1S3 | 130340 | NM_178814 | W |
| AP3B2 | 8120 | NM_004644 | W |
| APG16L | 55054 | NM_017974 | W |
| APH-1A | 51107 | NM_016022 | M |
| APOBEC1 | 339 | NM_001644 | W |
| APOL4 | 80832 | NM_030643 | M |
| APXL | 357 | NM_001649 | W |
| AQR | 9716 | NM_014691 | W |
| ARCN1 | 372 | NM_001655 | S |
| ARHGAP15 | 55843 | NM_018460 | W |
| ARHGAP17 | 55114 | NM_018054 | W |
| ARHGDIA | 396 | NM_004309 | W |
| ARL10C | 55207 | NM_018184 | W |
| ARL11 | 115761 | NM_138450 | M |
| ARL5C | 390790 | XM_372668 | M |
| ARMC2 | 84071 | NM_032131 | W |
| ARPP-21 | 10777 | NM_016300 | W |
| ARS2 | 51593 | NM_015908 | W |
| ASB10 | 136371 | NM_080871 | W |
| ASB4 | 51666 | NM_016116 | S |
| ASMTL | 8623 | NM_004192 | W |
| ASTL | 431705 | NM_001002036 | W |
| ATP10D | 57205 | NM_020453 | W |
| ATP5L2 | 267020 | NM_198822 | M |
| ATP5S | 27109 | NM_015684 | W |
| ATP6V0D1 | 9114 | NM_004691 | M |
| ATP6V1D | 51382 | NM_015994 | M |
| AZ2 | 64343 | NM_022461 | W |
| BACE1 | 23621 | NM_012104 | W |
| BATF | 10538 | NM_006399 | M |
| BBX | 56987 | NM_020235 | W |
| BC-2 | 27243 | NM_014453 | W |
| BCL2L12 | 83596 | NM_052842 | M |
| BEST3 | 84821 | NM_032735 | W |
| BEXL1 | 56271 | XM_043653 | W |
| BFSP1 | 631 | NM_001195 | W |
| BG1 | 23205 | NM_015162 | S |
| BGN | 633 | NM_001711 | M |
| BIG1 | 10565 | NM_006421 | S |
| BIN3 | 55909 | NM_018688 | W |
| BMP15 | 9210 | NM_005448 | W |
| BMP4 | 652 | NM_001202 | S |
| BMPER | 168667 | NM_133468 | W |
| BMSC-UBP | 84993 | NM_032907 | S |
| BRD8 | 10902 | NM_006696 | W |
| BRP44L | 51660 | NM_016098 | M |
| BRUNOL6 | 60677 | NM_052840 | W |
| BSCL2 | 26580 | NM_032667 | W |
| BTBD11 | 121551 | NM_152322 | M |
| BTN3A3 | 10384 | NM_006994 | W |

TABLE 2-continued

| GeneSymbol | EntrezGeneID | Genbank Acc. No. | NFAT Score |
|---|---|---|---|
| C10ORF53 | 282966 | NM_182554 | M |
| C10ORF56 | 219654 | NM_153367 | M |
| C10ORF59 | 55328 | NM_018363 | W |
| C10ORF81 | 79949 | NM_024889 | M |
| C10ORF94 | 93426 | NM_130784 | W |
| C11ORF17 | 56672 | NM_020642 | W |
| C13ORF10 | 64062 | NM_022118 | W |
| C13ORF12 | 51371 | NM_015932 | M |
| C14ORF11 | 55837 | NM_018453 | M |
| C14ORF126 | 112487 | NM_080664 | W |
| C14ORF147 | 171546 | NM_138288 | W |
| C14ORF43 | 91748 | NM_194278 | W |
| C14ORF73 | 91828 | XM_040910 | W |
| C14ORF8 | 122664 | NM_173846 | W |
| C14ORF92 | 9878 | XM_375045 | W |
| C15ORF24 | 56851 | NM_020154 | S |
| C16ORF23 | 79006 | NM_024042 | W |
| C18ORF34 | 374864 | NM_198995 | W |
| C19ORF13 | 26065 | NM_015578 | S |
| C19ORF24 | 55009 | NM_017914 | W |
| C1ORF123 | 54987 | NM_017887 | M |
| C20ORF104 | 51230 | NM_016436 | S |
| C20ORF96 | 140680 | NM_153269 | M |
| C21ORF107 | 54014 | NM_018963 | W |
| C21ORF45 | 54069 | NM_018944 | W |
| C21ORF49 | 54067 | NM_001006116 | S |
| C21ORF6 | 10069 | NM_016940 | W |
| C21ORF84 | 114038 | NM_153752 | W |
| C3ORF6 | 152137 | NM_174908 | M |
| C4ORF8 | 8603 | NM_003704 | W |
| C5ORF11 | 167410 | NM_153234 | W |
| C6ORF115 | 58527 | XM_371848 | M |
| C6ORF191 | 253582 | XM_173166 | S |
| C6ORF51 | 112495 | NM_138408 | W |
| C6ORF57 | 135154 | NM_145267 | W |
| C6ORF59 | 79992 | NM_024929 | W |
| C6ORF84 | 22832 | XM_376518 | S |
| C8ORF4 | 56892 | NM_020130 | W |
| C9ORF11 | 54586 | XM_035953 | M |
| C9ORF138 | 158297 | NM_153707 | M |
| C9ORF150 | 286343 | NM_203403 | W |
| C9ORF71 | 169693 | XM_376874 | M |
| C9ORF72 | 203228 | NM_018325 | S |
| C9ORF79 | 286234 | NM_178828 | M |
| C9ORF84 | 158401 | NM_173521 | W |
| CABLES2 | 81928 | NM_031215 | W |
| CACNA1A | 773 | NM_000068 | W |
| CACNG4 | 27092 | NM_014405 | W |
| CADPS | 8618 | NM_003716 | W |
| CARD12 | 58484 | NM_021209 | W |
| CASC1 | 55259 | NM_018272 | S |
| CAV3 | 859 | NM_001234 | W |
| CBLL1 | 79872 | NM_024814 | S |
| CBLN2 | 147381 | NM_182511 | W |
| CBX6 | 23466 | NM_014292 | W |
| CCDC125 | 202243 | NM_176816 | M |
| CCK | 885 | NM_000729 | M |
| CCL11 | 6356 | NM_002986 | M |
| CCNB2 | 9133 | NM_004701 | S |
| CCNK | 8812 | NM_003858 | M |
| CCR6 | 1235 | NM_004367 | W |
| CCRN4L | 25819 | NM_012118 | M |
| CD151 | 977 | NM_004357 | W |
| CD1E | 913 | NM_030893 | W |
| CD209L | 10332 | NM_014257 | M |
| CD3G | 917 | NM_000073 | W |
| CD5 | 921 | NM_014207 | W |
| CD74 | 972 | NM_004355 | W |
| CDC27 | 996 | NM_001256 | S |
| CDC2L5 | 8621 | NM_003718 | M |
| CDC42EP5 | 148170 | NM_145057 | W |
| CDH9 | 1007 | NM_016279 | W |
| CENTG1 | 116986 | NM_014770 | W |
| CFL2 | 1073 | NM_021914 | W |
| CGI-04 | 51067 | NM_015936 | S |
| CHCHD5 | 84269 | NM_032309 | W |
| CHD4 | 1108 | NM_001273 | W |
| CHERP | 10523 | NM_006387 | W |
| CHFR | 55743 | NM_018223 | W |
| CHRM3 | 1131 | NM_000740 | W |
| CHRNA4 | 1137 | NM_000744 | W |
| CIRBP | 1153 | NM_001280 | M |
| CKN1 | 1161 | NM_000082 | W |
| CLCN4 | 1183 | NM_001830 | W |
| CLDN22 | 53842 | XM_210581 | S |
| CLPS | 1208 | NM_001832 | M |
| CLUL1 | 27098 | NM_014410 | W |
| CMAS | 55907 | NM_018686 | M |
| CMRF-35H | 11314 | NM_007261 | W |
| CNTN3 | 5067 | XM_039627 | M |
| COMT | 1312 | NM_000754 | W |
| COPA | 1314 | NM_004371 | S |
| COPB1 | 1315 | NM_016451 | S |
| COPB2 | 9276 | NM_004766 | S |
| COPE | 11316 | NM_007263 | S |
| COPG | 22820 | NM_016128 | S |
| COPZ1 | 22818 | NM_016057 | S |
| COX8A | 1351 | NM_004074 | W |
| CPEB4 | 80315 | NM_030627 | S |
| CPT2 | 1376 | NM_000098 | M |
| CRBN | 51185 | NM_016302 | W |
| CRHR2 | 1395 | NM_001883 | W |
| CRLF3 | 51379 | NM_015986 | M |
| CRSP2 | 9282 | NM_004229 | W |
| CRSP3 | 9439 | NM_004830 | W |
| CRSP6 | 9440 | NM_004268 | W |
| CRSP9 | 9443 | NM_004270 | M |
| CRXBA2 | 1412 | NM_005209 | W |
| CRXBB | 1414 | NM_001887 | W |
| CRXBB3 | 1417 | NM_004076 | W |
| CRXGC | 1420 | NM_020989 | W |
| CSAD | 51380 | NM_015989 | W |
| CSE1L | 1434 | NM_001316 | S |
| CST7 | 8530 | NM_003650 | W |
| CYLC1 | 1538 | XM_088636 | W |
| CYP1A1 | 1543 | NM_000499 | W |
| CYP2S1 | 29785 | NM_030622 | S |
| CYP3A5 | 1577 | NM_000777 | W |
| CYT19 | 57412 | NM_020682 | S |
| D2S448 | 7837 | XM_056455 | W |
| D4ST1 | 113189 | NM_130468 | S |
| DAAM1 | 23002 | NM_014992 | W |
| DACH1 | 1602 | NM_004392 | M |
| DBI | 1622 | NM_020548 | W |
| DC2 | 58505 | NM_021227 | W |
| DDX46 | 9879 | NM_014829 | W |
| DDX53 | 168400 | NM_182699 | M |
| DGCR6L | 85359 | NM_033257 | M |
| DHPS | 1725 | NM_001930 | W |
| DHRS4 | 10901 | NM_021004 | M |
| DHRS4L2 | 317749 | NM_198083 | M |
| DHRS9 | 10170 | NM_005771 | M |
| DIABLO | 56616 | NM_019887 | S |
| DIPA | 11007 | NM_006848 | S |
| DISP2 | 85455 | NM_033510 | M |
| DJ383J4.3 | 91687 | XM_371328 | M |
| DKFZP434B1231 | 91156 | NM_178275 | M |
| DKFZP547E1010 | 26097 | NM_015607 | M |
| DKFZP564D1378 | 84064 | NM_032124 | M |
| DKFZP566D1346 | 81573 | NM_030816 | M |
| DKFZP686P0288 | 285190 | NM_182588 | W |
| DKFZP761B1514 | 84248 | NM_032288 | W |
| DLAT | 1737 | NM_001931 | W |
| DNAJC5G | 285126 | NM_173650 | M |
| DNM1L | 10059 | NM_005690 | W |
| DONSON | 29980 | NM_145794 | M |
| DRPLA | 1822 | NM_001940 | M |
| DSEL | 92126 | NM_032160 | M |
| DSG4 | 147409 | NM_177986 | M |
| DUSP12 | 11266 | NM_007240 | M |
| DUSP16 | 80824 | NM_030640 | W |
| DUSP18 | 150290 | NM_152511 | W |
| DUX1 | 26584 | NM_012146 | W |
| DUX5 | 26581 | NM_012149 | W |
| DVL3 | 1857 | NM_004423 | W |
| E(X)2 | 56943 | NM_020189 | W |

TABLE 2-continued

| GeneSymbol | EntrezGeneID | Genbank Acc. No. | NFAT Score |
|---|---|---|---|
| E2IG2 | 51287 | NM_016565 | W |
| EBPL | 84650 | NM_032565 | W |
| EG1 | 80306 | NM_025205 | S |
| EGLN3 | 112399 | NM_022073 | M |
| EHD2 | 30846 | NM_014601 | M |
| ELMOD1 | 55531 | NM_018712 | S |
| ELXS | 25909 | NM_015446 | S |
| EML4 | 27436 | NM_019063 | M |
| EPB41L5 | 57669 | NM_020909 | W |
| EPO | 2056 | NM_000799 | M |
| EPSTI1 | 94240 | NM_033255 | M |
| ERBB4 | 2066 | NM_005235 | M |
| EREG | 2069 | NM_001432 | W |
| ERK8 | 225689 | NM_139021 | W |
| ESRRBL1 | 55081 | NM_018010 | W |
| EVI5 | 7813 | NM_005665 | W |
| F11R | 50848 | NM_016946 | M |
| FAM108C1 | 58489 | XM_051862 | S |
| FAM14A | 83982 | NM_032036 | W |
| FAM171A2 | 284069 | XM_208993 | S |
| FAM23B | 0 | XM_291726 | W |
| FAM31C | 79958 | NM_024898 | M |
| FAM38A | 9780 | NM_014745 | W |
| FAM57B | 83723 | NM_031478 | W |
| FAS | 355 | NM_000043 | S |
| FASTKD5 | 60493 | NM_021826 | M |
| FBXL20 | 84961 | NM_032875 | W |
| FBXL3P | 26223 | NM_012159 | W |
| FBXO11 | 80204 | NM_012167 | M |
| FBXO22 | 26263 | NM_012170 | W |
| FBXO46 | 23403 | XM_371179 | W |
| FBXO5 | 26271 | NM_012177 | S |
| FCGR3A | 2214 | NM_000569 | W |
| FCHSD2 | 9873 | NM_014824 | M |
| FGF14 | 2259 | NM_004115 | W |
| FGF7 | 2252 | NM_002009 | W |
| FGFR2 | 2263 | NM_000141 | W |
| FGFR4 | 2264 | NM_002011 | M |
| FKBP1C | 135521 | XM_059776 | W |
| FLJ10159 | 55084 | NM_018013 | W |
| FLJ10352 | 55125 | NM_018069 | W |
| FLJ10613 | 54552 | NM_019067 | W |
| FLJ10759 | 55223 | NM_018207 | M |
| FLJ10826 | 55239 | NM_018233 | M |
| FLJ11126 | 55308 | NM_018332 | W |
| FLJ11127 | 54491 | NM_019018 | M |
| FLJ11193 | 55322 | NM_018356 | W |
| FLJ12517 | 65094 | NM_023007 | W |
| FLJ14299 | 80139 | NM_025069 | S |
| FLJ20152 | 54463 | NM_019000 | W |
| FLJ20257 | 56257 | NM_019606 | M |
| FLJ20280 | 54876 | NM_017741 | M |
| FLJ20291 | 54883 | NM_017748 | M |
| FLJ20321 | 54897 | NM_017766 | M |
| FLJ20485 | 54517 | NM_019042 | W |
| FLJ20509 | 54956 | NM_017851 | W |
| FLJ20519 | 54964 | NM_017860 | W |
| FLJ20534 | 54969 | NM_017867 | S |
| FLJ20618 | 55000 | NM_017903 | M |
| FLJ20793/TMX3 | 54495 | NM_019022 | S |
| FLJ20972 | 80098 | NM_025030 | W |
| FLJ21415 | 79794 | NM_024738 | S |
| FLJ21687 | 79917 | NM_024859 | M |
| FLJ21986 | 79974 | NM_024913 | M |
| FLJ22531 | 79703 | NM_024650 | M |
| FLJ22688 | 80199 | NM_025129 | W |
| FLJ23554 | 79864 | NM_024806 | W |
| FLJ25286 | 153443 | NM_152546 | W |
| FLJ25555 | 124930 | NM_152345 | M |
| FLJ30656 | 124801 | NM_152344 | S |
| FLJ32356 | 144717 | NM_144671 | W |
| FLJ32421 | 148362 | NM_144695 | W |
| FLJ32569 | 148811 | NM_152491 | W |
| FLJ32682 | 220081 | NM_182542 | W |
| FLJ32734 | 146849 | NM_144681 | W |
| FLJ32743 | 220136 | NM_145020 | M |
| FLJ33516 | 139221 | NM_152423 | M |
| FLJ33814 | 150275 | NM_173510 | W |
| FLJ33817 | 124997 | NM_152348 | M |
| FLJ34690 | 284034 | NM_182567 | W |
| FLJ35757 | 162333 | NM_152598 | W |
| FLJ35838 | 163479 | NM_173532 | W |
| FLJ35843 | 160762 | NM_152591 | W |
| FLJ35961 | 127294 | NM_152372 | W |
| FLJ36070 | 284358 | NM_182574 | S |
| FLJ36754/P18SRP | 285672 | NM_173829 | S |
| FLJ36878 | 284114 | NM_178518 | W |
| FLJ38984 | 285097 | NM_178530 | W |
| FLJ38984 | 127703 | NM_152374 | W |
| FLJ39117 | 126638 | XM_371312 | W |
| FLJ39155 | 133584 | NM_152403 | W |
| FLJ40160 | 128209 | NM_173484 | W |
| FLJ40172 | 285051 | NM_173649 | M |
| FLJ40311 | 124535 | XM_064190 | S |
| FLJ42953 | 400892 | NM_207474 | W |
| FLJ42957 | 400077 | NM_207436 | W |
| FLJ43965 | 389026 | NM_207406 | W |
| FLJ44290 | 375347 | NM_198564 | M |
| FLJ44313 | 400658 | NM_207460 | M |
| FLJ45121 | 400556 | NM_207451 | W |
| FLJ45803 | 399948 | NM_207429 | W |
| FLJ46354 | 374977 | NM_198547 | W |
| FLJ46365 | 401459 | NM_207504 | S |
| FLJ46481 | 389197 | NM_207405 | W |
| FOXB1 | 27023 | NM_012182 | W |
| FOXK2 | 3607 | NM_004514 | S |
| FOXP2 | 93986 | NM_014491 | W |
| FOXP4 | 116113 | NM_138457 | W |
| FRMPD1 | 22844 | NM_014907 | M |
| FRRS1 | 0 | XM_372784 | W |
| FSHPRH1 | 2491 | NM_006733 | W |
| FSIP1 | 161835 | NM_152597 | S |
| FTH1 | 2495 | NM_002032 | W |
| FXC1 | 26515 | NM_012192 | W |
| FXYD2 | 486 | NM_001680 | M |
| FYN | 2534 | NM_002037 | W |
| GABRB1 | 2560 | NM_000812 | W |
| GAF1 | 26056 | NM_015470 | S |
| GART | 2618 | NM_000819 | W |
| GBP1 | 2633 | NM_002053 | W |
| GBP5 | 115362 | NM_052942 | M |
| GCAT | 23464 | NM_014291 | M |
| GDNF | 2668 | NM_000514 | W |
| GGA1 | 26088 | NM_001001560 | M |
| GGA3 | 23163 | NM_014001 | M |
| GJB3 | 2707 | NM_024009 | W |
| GL004 | 56947 | NM_020194 | W |
| GLMN | 11146 | NM_053274 | M |
| GLT1D1 | 144423 | NM_144669 | M |
| GMFG | 9535 | NM_004877 | W |
| GNAQ | 2776 | NM_002072 | W |
| GOLGA6 | 55889 | NM_018652 | W |
| GORASP1 | 64689 | NM_031899 | W |
| GOSR2 | 9570 | NM_004287 | S |
| GOT1 | 2805 | NM_002079 | W |
| GPD1 | 2819 | NM_005276 | M |
| GPD1L | 23171 | NM_015141 | S |
| GPHA2 | 170589 | NM_130769 | M |
| GPKOW | 27238 | NM_015698 | W |
| GPM6B | 2824 | NM_005278 | W |
| GPR101 | 83550 | NM_054021 | W |
| GPR114 | 221188 | NM_153837 | W |
| GPR14 | 2837 | NM_018949 | M |
| GPR23 | 2846 | NM_005296 | M |
| GPR50 | 9248 | NM_004224 | W |
| GPR56 | 9289 | NM_005682 | W |
| GPR73L1 | 128674 | NM_144733 | W |
| GRB7 | 2886 | NM_005310 | W |
| GRID1 | 2894 | XM_043613 | W |
| GRID2 | 2895 | NM_001510 | W |
| GRK4 | 2868 | NM_005307 | M |
| GRK7 | 131890 | NM_139209 | W |
| GRSP1 | 23150 | XM_114303 | S |
| GSR | 2936 | NM_000637 | M |
| GSTM2 | 2946 | NM_000848 | M |
| GTPBP1 | 9567 | NM_004286 | W |

TABLE 2-continued

| GeneSymbol | EntrezGeneID | Genbank Acc. No. | NFAT Score |
|---|---|---|---|
| GUCA1B | 2979 | NM_002098 | S |
| H2AFZ | 3015 | NM_002106 | W |
| H6PD | 9563 | NM_004285 | W |
| HBB | 3043 | NM_000518 | S |
| HBE1 | 3046 | NM_005330 | W |
| HBXIP | 10542 | NM_006402 | W |
| HCFC1 | 3054 | NM_005334 | W |
| HD | 3064 | NM_002111 | W |
| HDAC3 | 8841 | NM_003883 | W |
| HEMGN | 55363 | NM_018437 | W |
| HERV-FRD | 405754 | NM_207582 | W |
| HES2 | 54626 | XM_375684 | S |
| HIST1H1B | 3009 | NM_005322 | W |
| HIST1H2AL | 8332 | NM_003511 | W |
| HIST1H3B | 8358 | NM_003537 | W |
| HIST1H4A | 8359 | NM_003538 | W |
| HMG4L | 128872 | NM_178467 | M |
| HMP19 | 51617 | NM_015980 | M |
| HOXA7 | 3204 | NM_006896 | W |
| HOXB8 | 3218 | NM_024016 | W |
| HOXC8 | 3224 | NM_022658 | W |
| HOXD4 | 3233 | NM_014621 | M |
| HRASLS2 | 54979 | NM_017878 | W |
| HS747E2A | 25770 | NM_015370 | W |
| HSCARG | 57407 | NM_020677 | W |
| HSD11B2 | 3291 | NM_000196 | M |
| HSPB9 | 94086 | NM_033194 | W |
| HTR1A | 3350 | NM_000524 | W |
| HUNK | 30811 | NM_014586 | W |
| HXAL2 | 8692 | NM_003773 | W |
| HXAL4 | 23553 | NM_012269 | M |
| IDH3G | 3421 | NM_004135 | W |
| IFRG15 | 64163 | NM_022347 | W |
| IGF1R | 3480 | NM_000875 | S |
| IGSF8 | 93185 | NM_052868 | W |
| IL10RB | 3588 | NM_000628 | W |
| IL15RA | 3601 | NM_002189 | W |
| IL17 | 3605 | NM_002190 | W |
| IL17F | 112744 | NM_052872 | W |
| IL1F9 | 56300 | NM_019618 | W |
| IL1RAPL1 | 11141 | NM_014271 | M |
| IL1RL1 | 9173 | NM_003856 | W |
| IL20RA | 53832 | NM_014432 | M |
| IL22 | 50616 | NM_020525 | W |
| IL8RB | 3579 | NM_001557 | W |
| IL9 | 3578 | NM_000590 | M |
| INM01 | 157695 | NM_175075 | S |
| INSIG1 | 3638 | NM_005542 | W |
| INSM1 | 3642 | NM_002196 | W |
| INTERSEX | 55588 | XM_290829 | W |
| IRF7 | 3665 | NM_001572 | W |
| IRX1 | 79192 | XM_380171 | W |
| ITIH5 | 80760 | NM_030569 | M |
| ITSN2 | 50618 | NM_006277 | W |
| JARID1D | 8284 | NM_004653 | M |
| JIK | 51347 | NM_016281 | M |
| JM1 | 28952 | NM_014008 | W |
| JM11 | 90060 | NM_033626 | W |
| JMJD2B | 23030 | NM_015015 | M |
| JPH2 | 57158 | NM_020433 | M |
| JUB | 84962 | NM_198086 | W |
| KALRN | 8997 | NM_003947 | W |
| KBTBD7 | 84078 | NM_032138 | W |
| KCNC4 | 3749 | NM_004978 | W |
| KCNH4 | 23415 | NM_012285 | W |
| KCNIP2 | 30819 | NM_014591 | M |
| KCNJ3 | 3760 | NM_002239 | W |
| KCNK9 | 51305 | NM_016601 | M |
| KCNN4 | 3783 | NM_002250 | S |
| KCTD14 | 65987 | NM_023930 | W |
| KDR | 3791 | NM_002253 | W |
| KEAP1 | 9817 | NM_012289 | W |
| KIAA0217 | 23185 | XM_040265 | W |
| KIAA0284 | 283638 | XM_208766 | S |
| KIAA0303 | 23227 | XM_291141 | M |
| KIAA0527 | 26032 | XM_171054 | M |
| KIAA0540 | 23218 | XM_291064 | M |
| KIAA0542 | 9814 | XM_038520 | W |
| KIAA0701 | 23074 | XM_045423 | S |
| KIAA0841 | 23354 | XM_049237 | M |
| KIAA0980 | 22981 | NM_025176 | W |
| KIAA1012 | 22878 | NM_014939 | M |
| KIAA1068 | 23386 | NM_015332 | W |
| KIAA1189 | 57471 | XM_371576 | W |
| KIAA1194 | 57472 | NM_015455 | W |
| KIAA1280 | 55841 | NM_015691 | M |
| KIAA1361 | 57551 | XM_290796 | W |
| KIAA1510 | 57642 | NM_020882 | M |
| KIAA1549 | 57670 | XM_371956 | W |
| KIAA1573 | 57685 | NM_020925 | W |
| KIAA1726 | 85463 | XM_370654 | S |
| KIAA1862 | 84626 | XM_044212 | M |
| KIAA1971 | 123720 | XM_058720 | S |
| KIAA1987 | 170951 | XM_375298 | W |
| KIF11 | 3832 | NM_004523 | W |
| KIF13B | 23303 | NM_015254 | M |
| KIR2DL4 | 3805 | NM_002255 | W |
| KLHL11 | 55175 | NM_018143 | M |
| KLRC3 | 3823 | NM_002261 | M |
| KPNB1 | 3837 | NM_002265 | S |
| KRTAP21-2 | 337978 | NM_181617 | M |
| KRTAP4-5 | 85289 | NM_033188 | M |
| KRTAP9-4 | 85280 | NM_033191 | W |
| KRTHA5 | 3886 | NM_002280 | M |
| L1TD1 | 54596 | NM_019079 | M |
| LACE1 | 246269 | NM_145315 | W |
| LAP1B | 26092 | NM_015602 | M |
| LAP3 | 51056 | NM_015907 | W |
| LASP1 | 3927 | NM_006148 | W |
| LCN10 | 414332 | NM_001001712 | W |
| LEPRE1 | 64175 | NM_022356 | W |
| LGI2 | 55203 | NM_018176 | W |
| LIM | 10611 | NM_006457 | W |
| LIMCH1 | 22998 | XML_044461 | M |
| LMAN1L | 79748 | NM_021819 | S |
| LMF2 | 91289 | NM_033200 | W |
| LMNB1 | 4001 | NM_005573 | S |
| LMO7 | 4008 | NM_005358 | W |
| LMTK3 | 114783 | XM_055866 | W |
| LNX2 | 222484 | NM_153371 | W |
| LOC113828 | 113828 | NM_138435 | W |
| LOC116064 | 116064 | XM_057296 | M |
| LOC116068 | 116068 | XM_371760 | W |
| LOC120376 | 120376 | XM_071712 | W |
| LOC124402 | 124402 | NM_145253 | W |
| LOC125893 | 125893 | XM_064856 | W |
| LOC126520 | 126520 | XM_059051 | W |
| LOC131873 | 131873 | XM_067585 | M |
| LOC134145 | 134145 | NM_199133 | W |
| LOC144097 | 144097 | NM_138471 | W |
| LOC145414 | 0 | XM_085138 | W |
| LOC146443 | 146443 | XM_378558 | W |
| LOC146713 | 146713 | XM_378712 | W |
| LOC146795 | 146795 | XM_378701 | S |
| LOC146909 | 146909 | XM_085634 | M |
| LOC149643 | 0 | XM_086616 | W |
| LOC151484 | 151484 | XM_379159 | W |
| LOC152877 | 0 | XM_094066 | W |
| LOC153328 | 153328 | NM_145282 | W |
| LOC153441 | 153441 | XM_087671 | M |
| LOC154222 | 154222 | XM_379456 | W |
| LOC154907 | 0 | XM_088072 | W |
| LOC155036 | 155036 | XM_376722 | W |
| LOC158796 | 0 | XM_088677 | W |
| LOC159090 | 159090 | NM_145284 | W |
| LOC162427 | 162427 | NM_178126 | W |
| LOC163223 | 163223 | NM_001001411 | M |
| LOC164153 | 164153 | NM_203412 | M |
| LOC195977 | 195977 | XM_113625 | S |
| LOC196394 | 196394 | NM_207337 | M |
| LOC200493 | 0 | XM_115715 | W |
| LOC200933 | 200933 | XM_117294 | M |
| LOC201475 | 201475 | XM_113967 | S |
| LOC202051 | 202051 | XM_114430 | W |
| LOC205251 | 205251 | NM_174925 | W |
| LOC254808 | 254808 | XM_374069 | M |

TABLE 2-continued

| GeneSymbol | EntrezGeneID | Genbank Acc. No. | NFAT Score |
|---|---|---|---|
| LOC254897 | 0 | XM_170950 | W |
| LOC254938 | 254938 | XM_173120 | M |
| LOC256085 | 256085 | XM_172389 | W |
| LOC283152 | 283152 | XM_378314 | W |
| LOC283677 | 283677 | XM_208778 | M |
| LOC283914 | 283914 | XM_378589 | M |
| LOC283989 | 283989 | NM_207346 | W |
| LOC284058 | 284058 | NM_015443 | W |
| LOC284361 | 284361 | NM_175063 | W |
| LOC284371 | 284371 | XM_209155 | M |
| LOC284390 | 284390 | XM_371138 | W |
| LOC284661 | 284661 | XM_378832 | W |
| LOC284739 | 284739 | NM_207349 | W |
| LOC284825 | 284825 | XM_375935 | W |
| LOC285194 | 285194 | XM_379207 | W |
| LOC285248 | 0 | XM_211816 | W |
| LOC285636 | 285636 | NM_175921 | M |
| LOC285671 | 285671 | NM_178532 | M |
| LOC286076 | 286076 | XM_209889 | S |
| LOC338734 | 0 | XM_290547 | W |
| LOC338750 | 338750 | XM_291974 | M |
| LOC338756 | 0 | XM_291989 | W |
| LOC338829 | 338829 | XM_292122 | M |
| LOC339951 | 339951 | XM_293656 | M |
| LOC340109 | 340109 | XM_379322 | W |
| LOC340318 | 340318 | XM_290401 | M |
| LOC340591 | 340591 | XM_291346 | M |
| LOC340765 | 340765 | XM_291704 | M |
| LOC341356 | 0 | XM_292023 | W |
| LOC343578 | 343578 | XM_293123 | S |
| LOC345643 | 345643 | XM_293918 | S |
| LOC345651 | 0 | XM_293924 | W |
| LOC345711 | 345711 | XM_293937 | M |
| LOC347454 | 347454 | XM_293380 | S |
| LOC375133 | 375133 | NM_199345 | W |
| LOC375295 | 375295 | XM_374020 | M |
| LOC386597 | 386597 | XM_379073 | W |
| LOC387761 | 387761 | XM_373495 | S |
| LOC387784 | 0 | XM_373506 | W |
| LOC387810 | 0 | XM_373513 | W |
| LOC387825 | 0 | XM_370668 | W |
| LOC387845 | 0 | XM_370684 | W |
| LOC387914 | 0 | XM_370718 | W |
| LOC388298 | 0 | XM_370992 | W |
| LOC388381 | 388381 | XM_371053 | M |
| LOC388418 | 388418 | XM_373748 | M |
| LOC388432 | 0 | XM_371086 | W |
| LOC388469 | 388469 | XM_371111 | M |
| LOC388585 | 0 | XM_371215 | W |
| LOC388697 | 0 | XM_373868 | W |
| LOC388807 | 388807 | XM_373922 | M |
| LOC388847 | 388847 | XM_371424 | M |
| LOC389000 | 0 | XM_371534 | W |
| LOC389067 | 0 | XM_374021 | W |
| LOC389070 | 0 | XM_374022 | W |
| LOC389102 | 0 | XM_371623 | W |
| LOC389107 | 389107 | XM_371626 | M |
| LOC389153 | 0 | XM_374053 | W |
| LOC389224 | 389224 | XM_374086 | S |
| LOC389273 | 0 | XM_374115 | W |
| LOC389319 | 389319 | XM_374134 | M |
| LOC389370 | 0 | XM_374162 | W |
| LOC389386 | 0 | XM_371818 | W |
| LOC389416 | 0 | XM_371837 | W |
| LOC389541 | 0 | XM_371939 | W |
| LOC389705 | 389705 | XM_372076 | M |
| LOC389727 | 0 | XM_372092 | W |
| LOC389753 | 0 | XM_372112 | W |
| LOC389950 | 0 | XM_372307 | W |
| LOC390377 | 0 | XM_372486 | W |
| LOC390530 | 390530 | XM_372543 | M |
| LOC390734 | 390734 | XM_372640 | M |
| LOC391209 | 0 | XM_372840 | W |
| LOC391426 | 391426 | XM_372950 | M |
| LOC392549 | 392549 | XM_373373 | M |
| LOC392702 | 0 | XM_374730 | W |
| LOC392726 | 0 | XM_374734 | W |
| LOC392791 | 0 | XM_374752 | W |
| LOC399786 | 0 | XM_378236 | W |
| LOC399920 | 0 | XM_378300 | W |
| LOC399959 | 399959 | XM_378316 | M |
| LOC399968 | 399968 | XM_374945 | M |
| LOC400047 | 400047 | XM_378363 | S |
| LOC400092 | 0 | XM_378398 | W |
| LOC400479 | 0 | XM_375282 | W |
| LOC400619 | 0 | XM_378703 | W |
| LOC400622 | 400622 | XM_375491 | M |
| LOC400687 | 400687 | XM_375602 | S |
| LOC400688 | 400688 | XM_375603 | M |
| LOC400740 | 0 | XM_378840 | W |
| LOC400877 | 400877 | XM_379025 | M |
| LOC400939 | 400939 | XM_379072 | S |
| LOC401155 | 401155 | XM_379276 | S |
| LOC401169 | 0 | XM_379306 | W |
| LOC401175 | 0 | XM_379317 | W |
| LOC401286 | 0 | XM_376555 | W |
| LOC401293 | 401293 | XM_376558 | M |
| LOC401314 | 0 | XM_376586 | W |
| LOC401316 | 0 | XM_376587 | W |
| LOC401317 | 0 | XM_379479 | W |
| LOC401321 | 0 | XM_379483 | W |
| LOC401322 | 401322 | XM_376591 | M |
| LOC401518 | 0 | XM_379638 | W |
| LOC401548 | 0 | XM_376902 | W |
| LOC401552 | 0 | XM_379668 | W |
| LOC401624 | 401624 | XM_377073 | M |
| LOC401720 | 401720 | XM_377265 | M |
| LOC401778 | 401778 | XM_377343 | M |
| LOC402148 | 0 | XM_377818 | W |
| LOC402251 | 402251 | XM_377933 | M |
| LOC402382 | 402382 | XM_378090 | S |
| LOC402477 | 0 | XM_379803 | W |
| L0C402515 | 0 | XM_380112 | W |
| LOC402521 | 0 | XM_379848 | W |
| LOC402537 | 0 | XM_380120 | W |
| LOC402556 | 0 | XM_379877 | W |
| LOC402560 | 0 | XM_380127 | W |
| LOC402586 | 0 | XM_380138 | W |
| LOC402587 | 0 | XM_380139 | W |
| LOC402625 | 0 | XM_379975 | W |
| LOC402641 | 0 | XM_379995 | W |
| LOC404785 | 404785 | NM_207513 | W |
| LOC51054 | 51054 | NM_015899 | W |
| LOC51066 | 51066 | NM_015931 | W |
| LOC51333 | 51333 | NM_016643 | W |
| LOC51693 | 51693 | NM_016209 | W |
| LOC57168 | 57168 | NM_020437 | M |
| LOC88523 | 88523 | NM_033111 | S |
| LOC90120 | 90120 | XM_379680 | M |
| LOC92689 | 92689 | NM_138389 | W |
| LOC96597 | 96597 | XM_378655 | W |
| LOR | 4014 | NM_000427 | W |
| LPO | 4025 | NM_006151 | W |
| LTBP3 | 4054 | NM_021070 | W |
| LU | 4059 | NM_005581 | W |
| LXNX1 | 66004 | NM_177477 | M |
| LXZL1 | 84569 | NM_032517 | M |
| LY64 | 4064 | NM_005582 | W |
| M96 | 22823 | NM_007358 | W |
| MAD2L2 | 10459 | NM_006341 | W |
| MAGEL2 | 54551 | NM_019066 | W |
| MAP4 | 4134 | NM_002375 | M |
| MAPBPIP | 28956 | NM_014017 | S |
| MAPK13 | 5603 | NM_002754 | W |
| MAPRE2 | 10982 | NM_014268 | W |
| MASP1 | 5648 | NM_001879 | W |
| MBP | 4155 | NM_002385 | M |
| MBTPS2 | 51360 | NM_015884 | W |
| MC4R | 4160 | NM_005912 | W |
| MCC | 4163 | NM_002387 | W |
| MCRS1 | 10445 | NM_006337 | W |
| MDGA1 | 266727 | NM_153487 | W |
| MDH1B | 130752 | XM_059468 | W |
| MDS1 | 4197 | NM_004991 | S |
| MED19 | 219541 | NM_153450 | M |
| MEF2A | 4205 | NM_005587 | W |

TABLE 2-continued

| GeneSymbol | EntrezGeneID | Genbank Acc. No. | NFAT Score |
|---|---|---|---|
| MEF2B | 4207 | NM_005919 | W |
| MET | 4233 | NM_000245 | M |
| MFSD11 | 79157 | NM_024311 | W |
| MFSD3 | 113655 | NM_138431 | S |
| MGAT4B | 11282 | NM_014275 | M |
| MGC11266 | 79172 | NM_024322 | M |
| MGC14126 | 84984 | NM_032898 | W |
| MGC15882 | 84970 | NM_032884 | M |
| MGC16279 | 85002 | NM_032916 | M |
| MGC16372 | 92749 | NM_145038 | W |
| MGC16491 | 115572 | NM_052943 | M |
| MGC16597 | 339230 | XM_375500 | W |
| MGC17337 | 91283 | NM_080655 | W |
| MGC21394 | 404203 | NM_205841 | W |
| MGC23918 | 151903 | NM_144716 | W |
| MGC23937 | 139596 | NM_145052 | W |
| MGC26856 | 256710 | NM_152779 | W |
| MGC2941 | 79142 | NM_024297 | M |
| MGC33584 | 285971 | NM_173680 | M |
| MGC33887 | 201134 | NM_145036 | W |
| MGC39633 | 153733 | NM_152549 | W |
| MGC39696 | 255193 | NM_152771 | M |
| MGC41945 | 138724 | NM_203299 | W |
| MGC4238 | 84292 | NM_032332 | W |
| MGC4734 | 138065 | NM_145051 | M |
| MGC50559 | 254013 | NM_173802 | W |
| MGC52000 | 375260 | NM_198943 | W |
| MGC87042 | 256227 | NM_207342 | M |
| MICAL3 | 57553 | XM_032997 | W |
| MIG12 | 58526 | NM_021242 | W |
| MIRAB13 | 85377 | NM_033386 | W |
| MLL | 4297 | NM_005933 | M |
| MLL4 | 9757 | NM_014727 | M |
| MLR2 | 84458 | XM_050988 | M |
| MLSTD1 | 55711 | NM_018099 | M |
| MMP24 | 10893 | NM_006690 | W |
| MO25 | 51719 | NM_016289 | W |
| MORF4L1 | 10933 | NM_006791 | W |
| MRC2 | 9902 | NM_006039 | W |
| MRPL48 | 51642 | NM_016055 | W |
| MRPS21 | 54460 | NM_018997 | W |
| MRPS6 | 64968 | NM_032476 | M |
| MRS2L | 57380 | NM_020662 | M |
| MSL3L1 | 10943 | NM_078628 | S |
| MT1A | 4489 | NM_005946 | W |
| MTFMT | 123263 | NM_139242 | W |
| MTMR6 | 9107 | NM_004685 | S |
| MTMR9 | 66036 | NM_015458 | W |
| MTRF1L | 54516 | NM_019041 | W |
| MYADM | 91663 | NM_138373 | M |
| MYBL2 | 4605 | NM_002466 | M |
| MYC | 4609 | NM_002467 | M |
| MYH1 | 4619 | NM_005963 | W |
| MYLIP | 29116 | NM_013262 | W |
| MYO5C | 55930 | NM_018728 | W |
| MYO9A | 4649 | NM_006901 | M |
| MYST3 | 7994 | NM_006766 | W |
| NAP1L4 | 4676 | NM_005969 | W |
| NAPA | 8775 | NM_003827 | M |
| NAPG | 8774 | NM_003826 | W |
| NBPF10 | 388776 | XM_371384 | M |
| NCB5OR | 51167 | NM_016230 | W |
| NCBP2 | 22916 | NM_007362 | M |
| NCF4 | 4689 | NM_000631 | W |
| NCOA5 | 57727 | NM_020967 | W |
| NDEL1 | 81565 | NM_030808 | W |
| NDRG1 | 10397 | NM_006096 | M |
| NDUFA5 | 4698 | NM_005000 | M |
| NDUFB9 | 4715 | NM_005005 | W |
| NDUFC1 | 4717 | NM_002494 | W |
| NDUFS1 | 4719 | NM_005006 | W |
| NDUFS6 | 4726 | NM_004553 | W |
| NEBL | 10529 | NM_006393 | M |
| NET-5 | 10867 | NM_006675 | W |
| NEU4 | 129807 | NM_080741 | W |
| NEURL | 9148 | NM_004210 | S |
| NFATC2 | 4773 | NM_012340 | W |
| NFKB2 | 4791 | NM_002502 | W |
| NFS1 | 9054 | NM_021100 | W |
| NHLH2 | 4808 | NM_005599 | W |
| NIPA | 51530 | NM_016478 | S |
| NIPA2 | 81614 | NM_030922 | S |
| NOLC1 | 9221 | NM_004741 | M |
| NOPE | 57722 | NM_020962 | W |
| NPEPPS | 9520 | NM_006310 | M |
| NPFF | 8620 | NM_003717 | W |
| NPY2R | 4887 | NM_000910 | W |
| NPY5R | 4889 | NM_006174 | W |
| NRAS | 4893 | NM_002524 | M |
| NRM | 11270 | NM_007243 | W |
| NUCB1 | 4924 | NM_006184 | W |
| NUP107 | 57122 | NM_020401 | W |
| NUP133 | 55746 | NM_018230 | W |
| NUP160 | 23279 | XM_113678 | S |
| NUP205 | 23165 | XM_058073 | M |
| NUP54 | 53371 | NM_017426 | M |
| NUP62 | 23636 | NM_012346 | S |
| NUP93 | 9688 | NM_014669 | M |
| NUPL1 | 9818 | NM_014089 | M |
| NXD-TSP1 | 84654 | NM_032567 | M |
| NXF2 | 56001 | NM_017809 | W |
| NXF5 | 55998 | NM_032946 | W |
| NXT1 | 29107 | NM_013248 | W |
| NYD-SP28 | 85478 | NM_033124 | W |
| OFD1 | 8481 | NM_003611 | W |
| OKL38 | 29948 | NM_013370 | M |
| OPN3 | 23596 | NM_014322 | W |
| OR2A2 | 442361 | NM_001005480 | M |
| OR2B3 | 442184 | NM_001005226 | S |
| OR3A4 | 390756 | NM_001005334 | W |
| OR4A5 | 81318 | NM_001005272 | W |
| OR4K15 | 81127 | NM_001005486 | M |
| OR5B2 | 390190 | NM_001005566 | W |
| OR5K4 | 403278 | NM_001005517 | S |
| OR5M11 | 219487 | NM_001005245 | W |
| OR6C74 | 254783 | NM_001005490 | W |
| Orai1 | 84876 | NM_032790 | M |
| ORC3L | 23595 | NM_012381 | W |
| OSM | 5008 | NM_020530 | M |
| OSTM1 | 28962 | NM_014028 | S |
| OTOR | 56914 | NM_020157 | W |
| P4HA2 | 8974 | NM_004199 | S |
| PADI3 | 51702 | NM_016233 | W |
| PAGE-5 | 90737 | NM_130467 | W |
| PAI-RBP1 | 26135 | NM_015640 | W |
| PAK1IP1 | 55003 | NM_017906 | W |
| PAQR10 | 221938 | NM_198403 | W |
| PASD1 | 139135 | NM_173493 | M |
| PAWR | 5074 | NM_002583 | W |
| PAX2 | 5076 | NM_000278 | M |
| PCBP1 | 5093 | NM_006196 | W |
| PCDH11X | 83259 | NM_032971 | M |
| PCDH11X | 27328 | NM_014522 | S |
| PCDHB13 | 56123 | NM_018933 | M |
| PCDHGB7 | 56099 | NM_018927 | S |
| PCNP | 57092 | NM_020357 | W |
| PCOLCE | 5118 | NM_002593 | W |
| PCOLN3 | 5119 | NM_002768 | S |
| PDCD1LG2 | 80380 | NM_025239 | S |
| PDE6A | 5145 | NM_000440 | W |
| PDF | 64146 | NM_022341 | W |
| PDHA2 | 5161 | NM_005390 | W |
| PDP2 | 57546 | NM_020786 | W |
| PELO | 53918 | NM_015946 | S |
| PEPP3 | 22874 | NM_014935 | M |
| PERLD1 | 93210 | NM_033419 | W |
| PEX11A | 8800 | NM_003847 | S |
| PEX11G | 92960 | NM_080662 | M |
| PEX26 | 55670 | NM_017929 | W |
| PEX3 | 8504 | NM_003630 | M |
| PFKFB3 | 5209 | NM_004566 | W |
| PHF13 | 148479 | NM_153812 | W |
| PHF17 | 79960 | NM_024900 | M |
| PHF2 | 5253 | NM_005392 | M |
| PHYHIPL | 84457 | NM_032439 | W |
| PIGW | 284098 | NM_178517 | W |

TABLE 2-continued

| GeneSymbol | EntrezGeneID | Genbank Acc. No. | NFAT Score |
|---|---|---|---|
| PIK3CB | 5291 | NM_006219 | S |
| PIK3R2 | 5296 | NM_005027 | S |
| PIK3R3 | 8503 | NM_003629 | W |
| PIK4CA | 5297 | NM_002650 | M |
| PIK4CB | 5298 | NM_002651 | W |
| PILRA | 29992 | NM_013439 | S |
| PIPOX | 51268 | NM_016518 | W |
| PIPPIN | 27254 | NM_014460 | S |
| PJA1 | 64219 | NM_022368 | M |
| PKD1L1 | 168507 | NM_138295 | W |
| PLA2G4D | 283748 | NM_178034 | M |
| PLAC8 | 51316 | NM_016619 | M |
| PMCA4 | 493 | NM_001684 | W |
| PMCH | 5367 | NM_002674 | M |
| PNLIP | 5406 | NM_000936 | W |
| PNLIPRP1 | 5407 | NM_006229 | W |
| PNUTL2 | 5414 | NM_004574 | S |
| POLG | 5428 | NM_002693 | M |
| POLH | 5429 | NM_006502 | M |
| PON3 | 5446 | NM_000940 | W |
| PPP1R13B | 23368 | NM_015316 | M |
| PPP1R9B | 84687 | NM_032595 | M |
| PPP3CA | 5530 | NM_000944 | S |
| PPP3R1 | 5534 | NM_000945 | M |
| PRDX3 | 10935 | NM_006793 | W |
| PRKACA | 5566 | NM_002730 | W |
| PRKWNK2 | 65268 | NM_006648 | M |
| PROK1 | 84432 | NM_032414 | W |
| PROL5 | 26952 | NM_012390 | W |
| PRPS1L1 | 221823 | NM_175886 | W |
| PRPSAP2 | 5636 | NM_002767 | S |
| PRRT1 | 80863 | NM_030651 | M |
| PRSS1 | 5644 | NM_002769 | M |
| PSG3 | 5671 | NM_021016 | W |
| PTD004 | 29789 | NM_013341 | W |
| PTD008 | 51398 | NM_016145 | M |
| PTPN13 | 5783 | NM_006264 | M |
| PTRH1 | 138428 | XM_059972 | W |
| PTX1 | 51290 | NM_016570 | W |
| PXGO1 | 26108 | NM_015617 | M |
| PXK | 54899 | NM_017771 | M |
| QP-C | 27089 | NM_014402 | S |
| RABGAP1 | 23637 | NM_012197 | W |
| RABGGTB | 5876 | NM_004582 | S |
| RABL2A | 11159 | NM_007082 | W |
| RAD9B | 144715 | NM_152442 | S |
| RAI14 | 26064 | NM_015577 | S |
| RAN | 5901 | NM_006325 | S |
| RANBP2 | 5903 | NM_006267 | W |
| RANBP2L1 | 84220 | NM_005054 | M |
| RAP1GA1 | 5909 | NM_002885 | M |
| RASD2 | 23551 | NM_014310 | W |
| RASL10B | 91608 | NM_033315 | W |
| RBM27 | 54439 | XM_291128 | W |
| RBM5 | 10181 | NM_005778 | W |
| RCE1 | 9986 | NM_005133 | W |
| RCOR1 | 23186 | NM_015156 | W |
| RDH12 | 145226 | NM_152443 | W |
| RDH5 | 5959 | NM_002905 | W |
| REPIN1 | 29803 | NM_013400 | W |
| REV3L | 5980 | NM_002912 | M |
| RFPL3 | 10738 | NM_006604 | W |
| RGS7 | 6000 | NM_002924 | M |
| RIOK3 | 8780 | NM_003831 | M |
| RKHD2 | 51320 | NM_016626 | W |
| RLN3 | 117579 | NM_080864 | W |
| RNF13 | 11342 | NM_007282 | W |
| RNF159 | 84333 | NM_032373 | M |
| RNF185 | 91445 | NM_152267 | M |
| RNF32 | 140545 | NM_030936 | M |
| RNPEPL1 | 57140 | NM_018226 | M |
| RORB | 6096 | NM_006914 | W |
| RP26 | 375298 | NM_201548 | W |
| RPGR | 6103 | NM_000328 | S |
| RPIB9 | 154661 | NM_138290 | W |
| RPL3L | 6123 | NM_005061 | W |
| RPS6KA2 | 6196 | NM_021135 | W |
| RRAS2 | 22800 | NM_012250 | M |
| RRH | 10692 | NM_006583 | W |
| RRM2 | 6241 | NM_001034 | M |
| RX1 | 11017 | NM_006857 | S |
| SAA2 | 6289 | NM_030754 | W |
| SALPR | 51289 | NM_016568 | W |
| SAST | 22983 | NM_014975 | M |
| SATB1 | 6304 | NM_002971 | W |
| SCA7 | 6314 | NM_000333 | W |
| SCFD1 | 23256 | NM_016106 | M |
| SCG3 | 29106 | NM_013243 | W |
| SCML1 | 6322 | NM_006746 | M |
| SEC13L1 | 6396 | NM_030673 | S |
| SEC22L1 | 9554 | NM_004892 | W |
| SECISBP2 | 79048 | NM_024077 | W |
| SELENBP1 | 8991 | NM_003944 | S |
| SENP1 | 29843 | NM_014554 | W |
| SENP6 | 26054 | NM_015571 | S |
| SENP7 | 57337 | NM_020654 | W |
| SENP8 | 123228 | NM_145204 | W |
| SERPINA12 | 145264 | NM_173850 | M |
| SERPINA9 | 327657 | NM_175739 | M |
| SERPINB1 | 1992 | NM_030666 | M |
| SERPINE1 | 5054 | NM_000602 | M |
| SEZ6L | 23544 | NM_021115 | W |
| SF4 | 57794 | NM_172231 | W |
| SFPQ | 6421 | NM_005066 | M |
| SFRS2 | 6427 | NM_003016 | M |
| SFRS3 | 6428 | NM_003017 | S |
| SFRS7 | 6432 | NM_006276 | W |
| SFT2D1 | 113402 | NM_145169 | S |
| SFXN5 | 94097 | NM_144579 | M |
| SHD | 56961 | NM_020209 | W |
| SIAHBP1 | 22827 | NM_014281 | M |
| SIGLEC8 | 27181 | NM_014442 | S |
| SIRT7 | 51547 | NM_016538 | S |
| SKIP | 51763 | NM_016532 | S |
| SLAMF6 | 114836 | NM_052931 | W |
| SLC12A9 | 56996 | NM_020246 | W |
| SLC22A1LS | 5003 | NM_007105 | W |
| SLC25A23 | 79085 | NM_024103 | W |
| SLC25A3 | 5250 | NM_002635 | M |
| SLC30A5 | 64924 | NM_022902 | S |
| SLC36A1 | 206358 | NM_078483 | W |
| SLC38A6 | 145389 | NM_153811 | M |
| SLC41A3 | 54946 | NM_017836 | M |
| SLC6A14 | 11254 | NM_007231 | W |
| SLC6A2 | 6530 | NM_001043 | W |
| SLC6A4 | 6532 | NM_001045 | W |
| SLCO2B1 | 11309 | NM_007256 | S |
| SMAD2 | 4087 | NM_005901 | M |
| SMARCD3 | 6604 | NM_003078 | M |
| SMC5L1 | 23137 | NM_015110 | M |
| SMG1 | 23049 | NM_014006 | W |
| SMOC2 | 64094 | NM_022138 | W |
| SNAP23 | 8773 | NM_003825 | W |
| SNRP70 | 6625 | NM_003089 | M |
| SNRPC | 6631 | NM_003093 | S |
| SNX27 | 81609 | NM_030918 | W |
| SOX8 | 30812 | NM_014587 | S |
| SP4 | 6671 | NM_003112 | W |
| SPINK4 | 27290 | NM_014471 | W |
| SPINT1 | 6692 | NM_003710 | W |
| SPTLC2 | 9517 | NM_004863 | S |
| SR140 | 23350 | XM_031553 | W |
| SREBF1 | 6720 | NM_004176 | M |
| SRP46 | 10929 | NM_032102 | M |
| SSA2 | 6738 | NM_004600 | W |
| SSTR2 | 6752 | NM_001050 | W |
| SSTR4 | 6754 | NM_001052 | W |
| SSX1 | 6756 | NM_005635 | W |
| STAM | 8027 | NM_003473 | M |
| STAMBPL1 | 57559 | NM_020799 | W |
| STEAP | 26872 | NM_012449 | W |
| STIM1 | 6786 | NM_003156 | S |
| STIM2 | 57620 | NM_020860 | W |
| STOML1 | 9399 | NM_004809 | W |
| STOML2 | 30968 | NM_013442 | W |
| STX18 | 53407 | NM_016930 | M |

TABLE 2-continued

| GeneSymbol | EntrezGeneID | Genbank Acc. No. | NFAT Score |
| --- | --- | --- | --- |
| STXBP2 | 6813 | NM_006949 | M |
| SULT1C2 | 27233 | NM_006588 | W |
| SUMO2 | 6613 | NM_006937 | W |
| SV2C | 22987 | XM_043493 | S |
| SYCP1 | 6847 | NM_003176 | W |
| SYNCRIP | 10492 | NM_006372 | W |
| SYNE2 | 23224 | NM_015180 | W |
| SYT15 | 83849 | NM_181519 | S |
| SYTL4 | 94121 | NM_080737 | W |
| T2BP | 92610 | NM_052864 | M |
| TAB3 | 257397 | NM_152787 | W |
| TAS2R45 | 259291 | NM_176886 | W |
| TBCC | 6903 | NM_003192 | W |
| TBK1 | 29110 | NM_013254 | M |
| TCEB2 | 6923 | NM_007108 | S |
| TDRKH | 11022 | NM_006862 | M |
| TESK2 | 10420 | NM_007170 | W |
| TEX13B | 56156 | NM_031273 | W |
| TEX14 | 56155 | NM_031272 | M |
| TFCP2L3 | 79977 | NM_024915 | M |
| TFPI2 | 7980 | NM_006528 | S |
| TGIF2LX | 90655 | NM_139214 | W |
| TGM3 | 7053 | NM_003245 | W |
| THG-1 | 81628 | NM_030935 | M |
| TIMELESS | 8914 | NM_003920 | W |
| TIPARP | 25976 | NM_015508 | M |
| TLR6 | 10333 | NM_006068 | M |
| TMEM11 | 8834 | NM_003876 | W |
| TMEM110 | 375346 | NM_198563 | S |
| TMEM14C | 51522 | NM_016462 | W |
| TMEM187 | 8269 | NM_003492 | W |
| TMEM199 | 147007 | NM_152464 | W |
| TMEM43 | 79188 | NM_024334 | S |
| TMEM63B | 55362 | XM_371822 | W |
| TMP21 | 10972 | NM_006827 | M |
| TNFRSF13C | 115650 | NM_052945 | W |
| TNFRSF18 | 8784 | NM_004195 | M |
| TNFSF13B | 10673 | NM_006573 | W |
| TNIK | 23043 | XM_039796 | S |
| TNKS1BP1 | 85456 | NM_033396 | W |
| TNXB | 7148 | NM_019105 | W |
| TOE1 | 114034 | NM_025077 | M |
| TOLLIP | 54472 | NM_019009 | W |
| TOR1AIP2 | 163590 | NM_145034 | W |
| TORC3 | 64784 | NM_022769 | W |
| TPTE | 7179 | NM_013315 | M |
| TRAPPC1 | 58485 | NM_021210 | M |
| TRIM22 | 10346 | NM_006074 | W |
| TRIM3 | 10612 | NM_006458 | M |
| TRIM33 | 51592 | NM_015906 | W |
| TRIM59 | 286827 | NM_173084 | M |
| TRNT1 | 51095 | NM_016000 | M |
| TROAP | 10024 | NM_005480 | S |
| TSPAN-1 | 10103 | NM_005727 | W |
| TULP1 | 7287 | NM_003322 | W |
| TULP4 | 56995 | NM_020245 | W |
| TXK | 7294 | NM_003328 | M |
| TXMS | 7298 | NM_001071 | W |
| TXNDC | 81542 | NM_030755 | W |
| TXNDC15 | 79770 | NM_024715 | S |
| TXNRD2 | 10587 | NM_006440 | W |
| UAP1 | 6675 | NM_003115 | W |
| UBAP1 | 51271 | NM_016525 | M |
| UBC | 316 | NM_021009 | M |
| UBE2L6 | 9246 | NM_004223 | W |
| UEV3 | 55293 | NM_018314 | S |
| UFM1 | 51569 | NM_016617 | W |
| UHSKERB | 57830 | NM_021046 | S |
| UMPS | 7372 | NM_000373 | M |
| UNQ2446 | 123904 | NM_198443 | W |
| UNQ2492 | 377841 | NM_198585 | W |
| UNQ3033 | 284415 | NM_198481 | W |
| UNQ9370 | 400454 | NM_207447 | W |
| UPF3B | 65109 | NM_023010 | W |
| USP13 | 8975 | NM_003940 | M |
| VAX2 | 25806 | NM_012476 | W |
| VCX2 | 51480 | NM_016378 | W |
| VEST1 | 116328 | NM_052958 | W |
| VGF | 7425 | NM_003378 | M |
| VGLL2 | 245806 | NM_153453 | W |
| VMP | 140767 | NM_080723 | S |
| VN1R4 | 317703 | NM_173857 | W |
| VPS13A | 23230 | NM_015186 | W |
| VPS28 | 51160 | NM_016208 | M |
| VPS35 | 55737 | NM_018206 | W |
| WARP | 64856 | NM_022834 | W |
| WFDC3 | 140686 | NM_181522 | W |
| WNT7B | 7477 | NM_058238 | W |
| WRNIP1 | 56897 | NM_020135 | S |
| XKR5 | 389610 | NM_207411 | M |
| XKRX2 | 353515 | NM_001002906 | M |
| XKRY | 9082 | NM_004677 | S |
| XPO7 | 23039 | NM_015024 | M |
| XYLT2 | 64132 | NM_022167 | W |
| YIPF3 | 25844 | NM_015388 | M |
| ZADH1 | 145482 | NM_152444 | W |
| ZAK | 51776 | NM_133646 | W |
| ZBTB2 | 57621 | NM_020861 | W |
| ZBTB7 | 51341 | NM_015898 | W |
| ZCCHC8 | 55596 | NM_017612 | W |
| ZDHHC2 | 51201 | NM_016353 | M |
| ZFP28 | 140612 | NM_020828 | W |
| ZFP67 | 51043 | NM_015872 | W |
| ZFR | 51663 | NM_016107 | W |
| ZNF143 | 7702 | NM_003442 | M |
| ZNF148 | 7707 | NM_021964 | S |
| ZNF157 | 7712 | NM_003446 | M |
| ZNF192 | 7745 | NM_006298 | W |
| ZNF267 | 10308 | NM_003414 | M |
| ZNF289 | 84364 | NM_032389 | S |
| ZNF295 | 49854 | NM_020727 | W |
| ZNF297B | 23099 | NM_014007 | W |
| ZNF304 | 57343 | NM_020657 | W |
| ZNF324 | 25799 | NM_014347 | W |
| ZNF334 | 55713 | NM_018102 | W |
| ZNF342 | 162979 | NM_145288 | S |
| ZNF354C | 30832 | NM_014594 | W |
| ZNF496 | 84838 | NM_032752 | W |
| ZNF501 | 115560 | NM_145044 | W |
| ZNF503 | 84858 | NM_032772 | W |
| ZNF512 | 84450 | NM_032434 | M |
| ZNF544 | 27300 | NM_014480 | W |
| ZNF568 | 374900 | NM_198539 | M |
| ZNF570 | 148268 | NM_144694 | W |
| ZNF615 | 284370 | NM_198480 | W |
| ZNF706 | 51123 | NM_016096 | M |
| ZNFN1A4 | 64375 | NM_022465 | M |
| ZNRD1 | 30834 | NM_014596 | W |
| ZSWIM1 | 90204 | NM_080603 | M |
| ZYX | 7791 | NM_003461 | M |
| ZZEF1 | 23140 | NM_015113 | S |
| ZZZ3 | 26009 | NM_015534 | M |

TABLE 3

| GeneSymbol | EntrezGeneID | Genbank Acc. No. | NFAT Score | Calcium Hit |
| --- | --- | --- | --- | --- |
| ABCC13 | 150000 | NM_138726 | M | |
| ACSBG1 | 23205 | NM_015162 | S | X |
| ACTB | 60 | NM_001101 | M | X |
| ADAMTS5 | 11096 | NM_007038 | M | |
| AFG3L1 | 172 | NM_001132 | M | X |
| AKR1CL2 | 83592 | NM_031436 | M | |
| ALCAM | 214 | NM_001627 | M | X |
| ANKRD58 | 347454 | XM_293380 | S | |
| ANKRD9 | 122416 | NM_152326 | M | |
| ANTXRL | 195977 | XM_113625 | S | |
| APH1A | 51107 | NM_016022 | M | |
| APOL4 | 80832 | NM_030643 | M | |
| ARCN1 | 372 | NM_001655 | S | |
| ARL5C | 390790 | XM_372668 | M | X |

TABLE 3-continued

| GeneSymbol | EntrezGeneID | Genbank Acc. No. | NFAT Score | Calcium Hit |
|---|---|---|---|---|
| AS3MT | 57412 | NM_020682 | S | |
| ASB4 | 51666 | NM_016116 | S | |
| ASPHD2 | 57168 | NM_020437 | M | |
| ATN1 | 1822 | NM_001940 | M | X |
| ATP5L2 | 267020 | NM_198822 | M | X |
| ATP6V0D1 | 9114 | NM_004691 | M | X |
| ATP6V1D | 51382 | NM_015994 | M | |
| BCDIN3 | 56257 | NM_019606 | M | |
| BGN | 633 | NM_001711 | M | |
| BMP4 | 652 | NM_001202 | S | |
| BREA2 | 286076 | XM_209889 | S | |
| BRP44L | 51660 | NM_016098 | M | |
| C10orf53 | 282966 | NM_182554 | M | |
| C10orf56 | 219654 | NM_153367 | M | |
| C12orf49 | 79794 | NM_024738 | S | |
| C19orf34 | 255193 | NM_152771 | M | |
| C19orf56 | 51398 | NM_016145 | M | |
| C1orf123 | 54987 | NM_017887 | M | X |
| C1orf77 | 26097 | NM_015607 | M | |
| C20orf95 | 343578 | XM_293123 | S | |
| C20orf96 | 140680 | NM_153269 | M | X |
| C21orf49 | 54067 | NM_001006116 | S | |
| C4orf27 | 54969 | NM_017867 | S | |
| C4orf30 | 54876 | NM_017741 | M | |
| C5orf14 | 79770 | NM_024715 | S | |
| C6orf115 | 58527 | XM_371848 | M | |
| C6orf191 | 253582 | XM_173166 | S | X |
| C8orf42 | 157695 | NM_175075 | S | X |
| C9orf11 | 54586 | XM_035953 | M | |
| C9orf138 | 158297 | NM_153707 | M | |
| C9orf71 | 169693 | XM_376874 | M | |
| C9orf72 | 203228 | NM_018325 | S | |
| CA5BL | 340591 | XM_291346 | M | |
| CASC1 | 55259 | NM_018272 | S | |
| CBLL1 | 79872 | NM_024814 | M | |
| CCDC11 | 220136 | NM_145020 | M | |
| CCDC125 | 202243 | NM_176816 | M | X |
| CCDC46 | 201134 | NM_145036 | M | |
| CCDC49 | 54883 | NM_017748 | M | |
| CCDC50 | 152137 | NM_174908 | M | |
| CCDC85B | 11007 | NM_006848 | S | |
| CCK | 885 | NM_000729 | M | |
| CCL11 | 6356 | NM_002986 | M | |
| CCNB2 | 9133 | NM_004701 | S | X |
| CCNK | 8812 | NM_003858 | M | |
| CDC27 | 996 | NM_001256 | S | |
| CDC2L5 | 8621 | NM_003718 | M | |
| CENPO | 79172 | NM_024322 | M | |
| CHMP1A | 5119 | NM_002768 | S | |
| CHST14 | 113189 | NM_130468 | S | |
| CIRBP | 1153 | NM_001280 | M | |
| CLDN22 | 53842 | XM_210581 | S | |
| CLEC4M | 10332 | NM_014257 | M | |
| CLPS | 1208 | NM_001832 | M | |
| CMAS | 55907 | NM_018686 | M | |
| CNTN3 | 5067 | XM_039627 | M | X |
| COL20A1 | 57642 | NM_020882 | M | |
| COPA | 1314 | NM_004371 | S | X |
| COPB1 | 1315 | NM_016451 | S | X |
| COPB2 | 9276 | NM_004766 | S | X |
| COPE | 11316 | NM_007263 | S | X |
| COPG | 22820 | NM_016128 | S | X |
| COPZ1 | 22818 | NM_016057 | S | X |
| CPEB4 | 80315 | NM_030627 | S | X |
| CPT2 | 1376 | NM_000098 | M | X |
| CRLF3 | 51379 | NM_015986 | M | |
| CYP2S1 | 29785 | NM_030622 | S | |
| DDX53 | 168400 | NM_182699 | M | |
| DENND1C | 79958 | NM_024898 | M | |
| DGCR6L | 85359 | NM_033257 | M | |
| DHRS4 | 10901 | NM_021004 | M | |
| DHRS4L2 | 317749 | NM_198083 | M | |
| DHRS9 | 10170 | NM_005771 | M | |
| DIABLO | 56616 | NM_019887 | S | |
| DISP2 | 85455 | NM_033510 | M | |
| DKFZP686A01247 | 22998 | XM_044461 | M | X |
| DNAJC5G | 285126 | NM_173650 | M | X |
| DONSON | 29980 | NM_145794 | M | |
| DSEL | 92126 | NM_032160 | M | |
| DSG4 | 147409 | NM_177986 | M | |
| DUSP12 | 11266 | NM_007240 | M | |
| EHD2 | 30846 | NM_014601 | M | |
| ELMOD1 | 55531 | NM_018712 | S | X |
| EPO | 2056 | NM_000799 | M | |
| ERBB4 | 2066 | NM_005235 | M | |
| F11R | 50848 | NM_016946 | M | |
| FAM105A | 54491 | NM_019018 | M | |
| FAM108C1 | 58489 | XM_051862 | S | X |
| FAM46B | 115572 | NM_052943 | M | |
| FAS | 355 | NM_000043 | S | X |
| FASTKD5 | 60493 | NM_021826 | M | X |
| FBXO11 | 80204 | NM_012167 | M | |
| FBXO45 | 200933 | XM_117294 | M | |
| FBXO5 | 26271 | NM_012177 | S | X |
| FLJ21986 | 79974 | NM_024913 | M | X |
| FLJ30698 | 400687 | XM_375602 | S | X |
| FLJ36070 | 284358 | NM_182574 | S | |
| FLJ40172 | 285051 | NM_173649 | M | |
| FLJ41047 | 399968 | XM_374945 | M | |
| FLJ44290 | 375347 | NM_198564 | M | |
| FLJ44313 | 400658 | NM_207460 | M | |
| FLJ45121 | 400556 | NM_207451 | M | |
| FLJ46365 | 401459 | NM_207504 | S | |
| FRMD4B | 23150 | XM_114303 | S | |
| FRMPD1 | 22844 | NM_014907 | M | X |
| FSIP1 | 161835 | NM_152597 | S | |
| FXYD2 | 486 | NM_001680 | M | |
| GBP5 | 115362 | NM_052942 | M | |
| GGA1 | 26088 | NM_001001560 | M | |
| GGA3 | 23163 | NM_014001 | M | X |
| GLMN | 11146 | NM_053274 | M | |
| GLT1D1 | 144423 | NM_144669 | M | X |
| GOSR2 | 9570 | NM_004287 | S | X |
| GPD1 | 2819 | NM_005276 | M | X |
| GPD1L | 23171 | NM_015141 | S | X |
| GPR23 | 2846 | NM_005296 | M | X |
| GRK4 | 2868 | NM_005307 | W | |
| GSR | 2936 | NM_000637 | M | |
| GSTM2 | 2946 | NM_000848 | M | X |
| GUCA1B | 2979 | NM_002098 | S | |
| HBB | 3043 | NM_000518 | S | |
| HDHD2 | 84064 | NM_032124 | M | |
| HSD11B2 | 3291 | NM_000196 | M | |
| HYAL4 | 23553 | NM_012269 | M | |
| ICA1L | 130026 | NM_138468 | M | |
| IGF1R | 3480 | NM_145574, NM_000875 | S | |
| IL20RA | 53832 | NM_014432 | M | |
| IL9 | 3578 | NM_000590 | M | X |
| ITIH5 | 80760 | NM_030569 | M | |
| JPH2 | 57158 | NM_020433 | M | X |
| KCNIP2 | 30819 | NM_014591 | M | X |
| KCNK9 | 51305 | NM_016601 | M | |
| KCNN4 | 3783 | NM_002250 | S | X |
| KIAA0284 | 283638 | XM_208766 | S | X |
| KIF13B | 23303 | NM_015254 | M | |
| KLHL11 | 55175 | NM_018143 | M | |
| KLRC3 | 3823 | NM_002261 | M | |
| KRBA1 | 84626 | XM_044212 | M | |
| KRT35 | 3886 | NM_002280 | M | X |
| KRTAP21-2 | 337978 | NM_181617 | M | X |
| KRTAP5-8 | 57830 | NM_021046 | S | X |
| L1TD1 | 54596 | NM_019079 | M | X |
| LASP1 | 3927 | NM_006148 | W | |
| LMAN1L | 79748 | NM_021819 | S | X |
| LMNB1 | 4001 | NM_005573 | S | X |
| LOC131873 | 131873 | XM_067585 | M | |
| LOC146795 | 146795 | XM_378701 | S | |
| LOC153441 | 153441 | XM_087671 | M | |
| LOC254938 | 254938 | XM_173120 | M | |
| LOC283914 | 283914 | XM_378589 | M | X |
| LOC284371 | 284371 | XM_209155 | M | |

TABLE 3-continued

| GeneSymbol | EntrezGeneID | Genbank Acc. No. | NFAT Score | Calcium Hit |
|---|---|---|---|---|
| LOC285636 | 285636 | NM_175921 | M | |
| LOC338750 | 338750 | XM_291974 | M | |
| LOC338829 | 338829 | XM_292122 | M | X |
| LOC340318 | 340318 | XM_290401 | M | |
| LOC340765 | 340765 | XM_291704 | M | |
| LOC345643 | 345643 | XM_293918 | S | |
| LOC345711 | 345711 | XM_293937 | M | X |
| LOC375295 | 375295 | XM_374020 | M | |
| LOC387761 | 387761 | XM_373495 | S | |
| LOC388381 | 388381 | XM_371053 | M | X |
| LOC388418 | 388418 | XM_373748 | M | |
| LOC388469 | 388469 | XM_371111 | M | X |
| LOC388776 | 388776 | XM_371384 | M | |
| LOC388807 | 388807 | XM_373922 | M | X |
| LOC389107 | 389107 | XM_371626 | M | X |
| LOC389224 | 389224 | XM_374086 | S | |
| LOC389319 | 389319 | XM_374134 | M | X |
| LOC390734 | 390734 | XM_372640 | M | |
| LOC391426 | 391426 | XM_372950 | M | X |
| LOC392549 | 392549 | XM_373373 | M | X |
| LOC399959 | 399959 | XM_378316 | M | |
| LOC400622 | 400622 | XM_375491 | M | |
| LOC400688 | 400688 | XM_375603 | M | |
| LOC400877 | 400877 | XM_379025 | M | X |
| LOC400939 | 400939 | XM_379072 | S | X |
| LOC401155 | 401155 | XM_379276 | S | X |
| LOC401293 | 401293 | XM_376558 | M | |
| LOC401322 | 401322 | XM_376591 | M | X |
| LOC401624 | 401624 | XM_377073 | M | X |
| LOC401720 | 401720 | XM_377265 | M | |
| LOC401778 | 401778 | XM_377343 | M | X |
| LOC402251 | 402251 | XM_377933 | M | |
| LOC402382 | 402382 | XM_378090 | S | |
| LOC90120 | 90120 | XM_379680 | M | |
| LRRC58 | 116064 | XM_057296 | M | |
| LSM12 | 124801 | NM_152344 | S | |
| LSM14A | 26065 | NM_015578 | S | |
| LYNX1 | 66004 | NM_177477 | M | X |
| LYZL1 | 84569 | NM_032517 | M | X |
| MAP4 | 4134 | NM_002375 | M | |
| MAPBPIP | 28956 | NM_014017 | S | |
| MAST4 | 23227 | XM_291141 | M | |
| MBP | 4155 | NM_002385 | M | |
| MED19 | 219541 | NM_153450 | M | X |
| MED28 | 80306 | NM_025205 | S | |
| MGAT4B | 11282 | NM_014275 | M | |
| MGC34829 | 284069 | XM_208993 | S | X |
| MGC87042 | 256227 | NM_207342 | M | |
| MICAL3 | 57553 | XM_032997 | W | |
| MLSTD1 | 55711 | NM_018099 | M | |
| MRPS6 | 64968 | NM_032476 | M | |
| MRS2L | 57380 | NM_020662 | M | X |
| MTMR6 | 9107 | NM_004685 | S | |
| MYADM | 91663 | NM_138373 | M | |
| MYO9A | 4649 | NM_006901 | M | X |
| NAPA | 8775 | NM_003827 | M | X |
| NAPG | 8774 | NM_003826 | | |
| NDRG1 | 10397 | NM_006096 | M | |
| NDUFA5 | 4698 | NM_005000 | M | X |
| NEBL | 10529 | NM_006393 | W | |
| NEURL | 9148 | NM_004210 | S | |
| NIPA2 | 81614 | NM_030922 | S | X |
| NRAS | 4893 | NM_002524 | M | |
| NRSN1 | 140767 | NM_080723 | S | |
| OR2A2 | 442361 | NM_001005480 | M | |
| OR2B3 | 442184 | NM_001005226 | S | |
| OR4K15 | 81127 | NM_001005486 | M | |
| OR5K4 | 403278 | NM_001005517 | S | |
| OSM | 5008 | NM_020530 | M | |
| OSTM1 | 28962 | NM_014028 | S | X |
| P4HA2 | 8974 | NM_004199 | S | |
| PASD1 | 139135 | NM_173493 | M | X |
| PCDH11X | 27328 | NM_014522 | S | |
| PCDH11Y | 83259 | NM_032971 | M | |
| PCDHB13 | 56123 | NM_018933 | M | |
| PCDHGB7 | 56099 | NM_018927 | S | |
| PDCD1LG2 | 80380 | NM_025239 | S | |
| PELO | 53918 | NM_015946 | S | |
| PEX11A | 8800 | NM_003847 | S | |
| PEX3 | 8504 | NM_003630 | M | |
| PHF23 | 79142 | NM_024297 | M | |
| PIK3R2 | 5296 | NM_005027 | S | |
| PIK4CA | 5297 | NM_002650 | M | X |
| PILRA | 29992 | NM_013439 | S | X |
| PJA1 | 64219 | NM_022368 | M | X |
| PLA2G4D | 283748 | NM_178034 | M | |
| PLEKHA6 | 22874 | NM_014935 | M | |
| PMCH | 5367 | NM_002674 | M | |
| POLG | 5428 | NM_002693 | M | |
| POMP | 51371 | NM_015932 | M | |
| PPP1R9B | 84687 | NM_032595 | M | |
| PPP3CA | 5530 | NM_000944 | S | |
| PPP3R1 | 5534 | NM_000945 | M | |
| PRRT1 | 80863 | NM_030651 | M | X |
| PRSS1 | 5644 | NM_002769 | M | X |
| PTPN13 | 5783 | NM_006264 | M | |
| RAB11FIP5 | 26056 | NM_015470 | S | |
| RAB12 | 201475 | XM_113967 | S | |
| RABGGTB | 5876 | NM_004582 | S | |
| RAD9B | 144715 | NM_152442 | S | X |
| RAI14 | 26064 | NM_015577 | S | |
| RAP1GAP | 5909 | NM_002885 | M | |
| REV3L | 5980 | NM_002912 | M | |
| RGS7 | 6000 | NM_002924 | M | |
| RIOK3 | 8780 | NM_003831 | M | |
| RLN3 | 117579 | NM_080864 | M | |
| RNF180 | 285671 | NM_178532 | M | |
| RNF185 | 91445 | NM_152267 | M | X |
| RNF32 | 140545 | NM_030936 | M | |
| RNPEPL1 | 57140 | NM_018226 | M | X |
| RP11-298P3.3 | 88523 | NM_033111 | S | |
| RPGR | 6103 | NM_000328 | S | X |
| RY1 | 11017 | NM_006857 | S | |
| SEC13 | 6396 | NM_030673 | S | |
| SELENBP1 | 8991 | NM_003944 | S | |
| SENP6 | 26054 | NM_015571 | S | |
| SEPT4 | 5414 | NM_004574 | S | X |
| SERPINA12 | 145264 | NM_173850 | M | |
| SERPINA9 | 327657 | NM_175739 | M | |
| SERPINB1 | 1992 | NM_030666 | M | |
| SERPINE1 | 5054 | NM_000602 | M | |
| SFXN5 | 94097 | NM_144579 | M | X |
| SIGLEC8 | 27181 | NM_014442 | S | |
| SLC25A3 | 5250 | NM_002635 | M | |
| SLC30A5 | 64924 | NM_022902 | S | |
| SLC38A6 | 145389 | NM_153811 | M | |
| SLC41A3 | 54946 | NM_017836 | M | X |
| SPTLC2 | 9517 | NM_004863 | S | X |
| STAM | 8027 | NM_003473 | M | X |
| STIM1 | 6786 | NM_003156 | S | X |
| STIM2 | 57620 | NM_020860 | M | X |
| STX18 | 53407 | NM_016930 | M | |
| STXBP2 | 6813 | NM_006949 | M | X |
| SUSD5 | 26032 | XM_171054 | M | |
| SV2C | 22987 | XM_043493 | S | |
| SYT15 | 83849 | NM_181519 | S | |
| TBK1 | 29110 | NM_013254 | M | |
| TDRKH | 11022 | NM_006862 | M | |
| TEX14 | 56155 | NM_031272 | M | |
| TFPI2 | 7980 | NM_006528 | S | |
| TIFA | 92610 | NM_052864 | M | |
| TLR6 | 10333 | NM_006068 | M | |
| TMED10 | 10972 | NM_006827 | M | X |
| TMEM110 | 375346 | NM_198563 | S | X |
| TMEM142A | 84876 | NM_032790 | M | X |
| TMEM43 | 79188 | NM_024334 | S | |
| TNFRSF18 | 8784 | NM_004195 | M | X |
| TNIK | 23043 | XM_039796 | S | |
| TOLLIP | 54472 | NM_019009 | W | |
| TOR1AIP1 | 26092 | NM_015602 | M | |
| TPTE | 7179 | NM_013315 | M | |
| TRIM59 | 286827 | NM_173084 | M | X |

TABLE 3-continued

| GeneSymbol | EntrezGeneID | Genbank Acc. No. | NFAT Score | Calcium Hit |
|---|---|---|---|---|
| TRNT1 | 51095 | NM_016000 | M | |
| TROAP | 10024 | NM_005480 | S | |
| TUG1 | 55000 | NM_017903 | M | |
| TXNDC10 | 54495 | NM_019022 | S | |
| UBAP1 | 51271 | NM_016525 | M | |
| UBC | 7316 | NM_021009 | M | X |
| UBL4B | 164153 | NM_203412 | M | |
| UBL7 | 84993 | NM_032907 | S | |
| UEVLD | 55293 | NM_018314 | S | X |
| UQCRQ | 27089 | NM_014402 | S | |
| USP13 | 8975 | NM_003940 | M | |
| VGF | 7425 | NM_003378 | M | |
| VPS28 | 51160 | NM_016208 | M | |
| WDR81 | 124997 | NM_152348 | M | |
| WHDC1 | 123720 | XM_058720 | S | |
| WNK2 | 65268 | NM_006648 | M | |
| XKR5 | 389610 | NM_207411 | M | X |
| XKRY | 9082 | NM_004677 | S | |
| XKRY2 | 353515 | NM_001002906 | M | |
| YARS2 | 51067 | NM_015936 | S | |
| ZC3H12C | 85463 | XM_370654 | S | |
| ZDHHC2 | 51201 | NM_016353 | M | |
| ZNF289 | 84364 | NM_032389 | S | X |
| ZNF706 | 51123 | NM_016096 | M | X |
| ZYX | 7791 | NM_003461 | M | |
| ZZEF1 | 23140 | NM_015113 | S | X |
| ZZZ3 | 26009 | NM_015534 | M | |

What is claimed is:

1. A method of modulating NFAT activity in a subject in need thereof, the method comprising administering a therapeutically effective amount of a pharmaceutical composition comprising an agent that inhibits the activity of a UEV3 protein and/or the expression of UEV3 gene.

2. The method of claim 1, wherein the subject is suffering from a cell proliferation disease or disorder.

3. The method of claim 2, wherein the cell proliferation disease or disorder is a neoplastic cell proliferation disorder.

4. The method of claim 2, wherein the neoplastic cell proliferation disorder is a therapy resistant cancer, a metastasis or malignant cancer.

5. The method of claim 1, wherein the subject is suffering from a cardiovascular disorder.

6. The method of claim 5, wherein the cardiovascular disorder is cardiac hypertrophy, restenosis, atherosclerosis, or angiogenesis.

7. The method of claim 1, wherein the subject is suffering from a bone disease associated with excessive osteoclast formation and the excessive activity needs to be suppressed.

8. The method of claim 1, wherein the subject is suffering from an angiogenic disease or disorder.

9. The method of claim 8, wherein the angiogenesis disorder is associated with VEGF-induced and IL-1 induced gene expression.

10. The method of claim 8, wherein the angiogenesis disorder is selected from a group consisting of cancer, age-related macular degeneration, diabetic retinopathy; rheumatoid arthritis; Alzheimer's disease; obesity and endometriosis.

11. The method of claim 1, wherein the agent is nucleic acid inhibitor which inhibits gene expression.

12. The method of claim 11, wherein the nucleic acid inhibitor is an siRNA or shRNA.

13. A method of modulating store-operated $Ca^{2+}$ entry into a cell, the method comprising administering a therapeutically effective amount of a pharmaceutical composition comprising an agent that inhibits the activity of a UEV3 protein and/or the expression of UEV3.

14. The method of claim 13, wherein the agent is a nucleic acid inhibitor which inhibits gene expression.

15. A method of treating and/or preventing hyperactivity or inappropriate immune response in a subject in need thereof, the method comprising administering a therapeutically effective amount of a pharmaceutical composition comprising an agent that inhibits the activity of a UEV3 protein and/or the expression of UEV3 gene.

16. The method of claim 15, wherein the hyperactivity or inappropriate immune response in a subject is associated with acute and chronic immune diseases selected from a group consisting of asthma, allergic rhinitis, allergic conjunctivitis, atopic dermatitis, rheumatoid arthritis, insulin-dependent diabetes, inflammatory bowel disease, autoimmune thyroiditis, hemolytic anemia, multiple sclerosis, transplant graft rejections and graft-versus-host disease.

17. The method of claim 15, wherein the agent is a nucleic acid inhibitor which inhibits gene expression.

18. The method of claim 17, wherein the nucleic acid inhibitor is an siRNA or shRNA.

\* \* \* \* \*